United States Patent
Weiss et al.

(10) Patent No.: US 11,896,645 B2
(45) Date of Patent: Feb. 13, 2024

(54) COMPOUNDS FOR USE IN THE TREATMENT OF TELOMERE RELATED DISEASES AND/OR TELOMERE RELATED MEDICAL CONDITIONS

(71) Applicant: UNIVERSITY OF THE WITWATERSRAND, JOHANNESBURG, Johannesburg (ZA)

(72) Inventors: Stefan Franz Thomas Weiss, Johannesburg (ZA); Boitelo Theresiah Letsolo, Johannesburg (ZA); Kerrilyn Naidoo, Durban (ZA); Tyrone Chad Otgaar, Roodepoort (ZA)

(73) Assignee: UNIVERSITY OF THE WITWATERSRAND, JOHANNESBURG, Johannesburg (ZA)

( * ) Notice: Subject to any disclaimer, the term of this patent is extended or adjusted under 35 U.S.C. 154(b) by 262 days.

(21) Appl. No.: 17/177,614

(22) Filed: Feb. 17, 2021

(65) Prior Publication Data
US 2021/0169974 A1  Jun. 10, 2021

Related U.S. Application Data

(62) Division of application No. 15/773,453, filed as application No. PCT/IB2016/056686 on Nov. 7, 2016, now abandoned.

(30) Foreign Application Priority Data

Nov. 5, 2015 (GB) ..................... 1519557

(51) Int. Cl.
| | |
|---|---|
| A61K 38/17 | (2006.01) |
| C12N 15/113 | (2010.01) |
| C07K 14/705 | (2006.01) |
| A61P 17/06 | (2006.01) |
| A61P 21/00 | (2006.01) |
| A61P 9/10 | (2006.01) |
| A61P 39/00 | (2006.01) |
| A61P 3/10 | (2006.01) |
| A61P 35/04 | (2006.01) |
| A61P 19/10 | (2006.01) |
| A61K 39/395 | (2006.01) |
| C07K 16/28 | (2006.01) |

(52) U.S. Cl.
CPC .......... *A61K 38/177* (2013.01); *A61K 39/395* (2013.01); *A61P 3/10* (2018.01); *A61P 9/10* (2018.01); *A61P 17/06* (2018.01); *A61P 19/10* (2018.01); *A61P 21/00* (2018.01); *A61P 35/04* (2018.01); *A61P 39/00* (2018.01); *C07K 14/70546* (2013.01); *C07K 16/28* (2013.01); *C12N 15/113* (2013.01); *C12N 2310/14* (2013.01)

(58) Field of Classification Search
None
See application file for complete search history.

(56) References Cited

U.S. PATENT DOCUMENTS

2014/0056932 A1  2/2014  Langlade-Demoyen et al.

OTHER PUBLICATIONS

Bernardes De Jesus et al. "Telomerase gene therapy in adult and old mice delays aging and increases longevity without increasing cancer." EMBO Mol Med. 2012;4(8):691-704.
Bodnar et al. "Extension of life-span by introduction of telomerase into normal human cells." Science. 1998;279(5349):349-52.
Cao et al. "Progerin and telomere dysfunction collaborate to trigger cellular senescence in normal human fibroblasts." J. Clin. Invest. 2011, 121: 2833-2844.
Capper et al., "The nature of telomere fusion and a definition of the critical telomere length in human cells." Genes Dev. 2007, 21: 2495-2508.
Cawthon, "Telomere measurement by quantitative PCR." Nucleic Acids Res. 2000, 30, 1-6.
Chetty et al. "Anti-LRP/LR specific antibody IgG1-iS18 impedes adhesion and invasion of liver cancer cells." PLoS One. 2014;9(5):e96268.
Chin et al., "P53 Deficiency Rescues the Adverse Effects of Telomere Loss and Cooperates With Telomere Dysfunction to Accelerate Carcinogenesis." Cell. 97, 527-538.
Cong & Shay, "Actions of human telomerase beyond telomeres." Cell Research 2008, 18(7):725-732.
Da Costa Bias et al. "Anti-LRP/LR specific antibody IgG1-iS18 and knock-down of LRP/LR by shRNAs rescue cells from Abeta42 induced cytotoxicity." Sci Rep. 2013;3:2702.
De Jesus et al. "Telomerase gene therapy in adult and old mice delays aging and increases longevity without increasing cancer." EMBO molecular medicine 2012. 4(8), 691-704.
De Lange, "Shelterin: the protein complex that shapes and safeguards human telomeres?" Genes Dev. 2005; 19(18):2100-10.

(Continued)

*Primary Examiner* — Ruixiang Li
(74) *Attorney, Agent, or Firm* — Casimir Jones SC; Lisa Mueller

(57) ABSTRACT

The invention relates to compounds for use in the treatment of telomere related diseases and/or telomere related medical conditions, particularly wherein said telomere related diseases and/or telomere related medical conditions are cancer and cellular ageing. Particularly, herein is disclosed 37 kDa/67 kDa laminin receptor precursor/high affinity laminin receptor (LRP/LR) and/or a fragment thereof for use in the treatment and/or prevention of cellular ageing.

6 Claims, 31 Drawing Sheets
Specification includes a Sequence Listing.

(56) References Cited

OTHER PUBLICATIONS

Dimri et al. "A biomarker that identifies senescent human cells in culture and in aging skin in vivo." Proc. Natl. Acad. Sci. 1995, U. S. A. 92: 9363-9367.

Gauczynski et al. "The 37-kDa/67-kDa laminin receptor acts as a receptor for infectious prions and is inhibited by polysulfated glycanes." J Infect Dis. 2006;194(5):702-9.

Gauczynski et al., "The 37-kDa/67-kDa laminin receptor acts as the cell-surface receptor for the cellular prion protein." Embo J. 2001; 20(21):5863-75.

Griffith et al. "Mammalian telomeres end in a large duplex loop." Cell 1999; 97(4):503-14.

Hayflick, "The limited in vitro lifetime of human diploid cell strains." Exp. Cell Res. 1965, 636: 614-636.

Hiyama et al. "Telomerase Activity in Human Breast Tumors." J. Natl. Cancer Inst. 1996, 88: 116-122.

Holt et al., "Regulation of telomerase activity in immortal cell lines." Mol Cell Biol. 1996;16(6):2932-9.

Hundt et al. "Identification of interaction domains of the prion protein with its 37-kDa/67-kDa laminin receptor." Embo J. 2001;20(21):5876-86.

Jovanovic et al. "Anti-LRP/LR specific antibodies and shRNAs impede amyloid beta shedding in Alzheimer's disease." Sci Rep. 2013; 3:2699.

Jovanovic et al. "High resolution imaging study of interactions between the 37 kDa/67 kDa laminin receptor and APP, beta-secretase and gamma-secretase in Alzheimer's disease." PLoS One. 2014;9(6):e100373.

Khumalo et al., "Knockdown of LRP/LR Induces Apoptosis in Breast and Oesophageal Cancer Cells." PloS one. 2015;10(10): e0139584.

Khumalo et al., "Adhesion and Invasion of Breast and Oesophageal Cancer Cells are Impeded by Anti-LRP/LR-Specific Antibody IgG1-iS18." PLoS One. 2013;8(6):e66297.

Khusal et al. "In vitro inhibition of angiogenesis by antibodies directed against the 37kDa/67kDa laminin receptor." PLoS One. 2013;8(3):e58888.

Kim et al. "Specific association of human telomerase activity with immortal cells and cancer." Science. 1994; 266(5193):2011-5.

Letsolo et al., "Fusion of short telomeres in human cells is characterized by extensive deletion and microhomology, and can result in complex rearrangements." Nucleic Acids Res. 2010;38(6):1841-52.

Leucht et al. "The 37 kDa/67 kDa laminin receptor is required for PrP(Sc) propagation in scrapie-infected neuronal cells." EMBO Rep. 2003;4(3):290-5.

Li et al. "Intrinsic resistance of tumorigenic breast cancer cells to chemotherapy." J Natl Cancer Inst. 2008;100(9):672-9.

Lin et al., "Telomere dysfunction and fusion during the progression of a human malignancy." Blood 2010, 44: 1899-1908.

Liu & Yung, "Mortalization of human promyelocytic leukemia HL-60 cells to be more susceptible to sodium butyrate-induced apoptosis and inhibition of telomerase activity by down-regulation of nucleophosmin/B23" Oncogene 1998. 17. 3055-3064.

Lopez-Otin et al., "The Hallmarks of Aging." Cell 2013. 153(6), 1194-1217.

Lu et al. "Telomerase expression and telomere length in breast cancer and their associations with adjuvant treatment and disease outcome." Breast Cancer Res. 2011;13(3):R56.

Mattern et al., "Dynamics of protein binding to telomeres in living cells: implications for telomere structure and function." Mol. Cell. Biol. 2004, 24: 5587-5594.

Mbazima et al., "Interactions between PrP(c) and other ligands with the 37-kDa/67-kDa laminin receptor." Front Biosci (Schol Ed). 2010; 15:1150-63.

Moodley & Weiss, "Downregulation of the non-integrin laminin receptor reduces cellular viability by inducing apoptosis in lung and cervical cancer cells." PLoS One. 2013; 8(3):e57409.

Nakamura & Cech, "Reversing Time: Origin of Telomerase." Cell. 92, 587-590.

Palm & De Lange, "How shelterin protects mammalian telomeres." Annu Rev Genet. 2008; 42:301-34.

Pospelova et al., "Pseudo-DNA damage response in senescent cells." Cell cycle 2009, 8(24), 4112-4118.

Schluth-Bolard et al., "Dynamics and plasticity of chromosome ends: consequences in human pathologies." Atlas Genet Cytogenet Oncol Haematol. 2010, 14(5): 501-524.

Sharma "Human telomerase acts as a hTR-independent reverse transcriptase in mitochondria." Nucleic Acids Res. 2012, 40, 712-725.

Shay & Wright, "Senescence and immortalization: role of telomeres and telomerase." Carcinogenesis. 2005; 26(5):867-74.

Shay & Wright, "Hallmarks of telomeres in ageing research." The Journal of pathology 2007, 211(2): 114-123.

Tomas-Loba et al. "Telomerase reverse transcriptase delays aging in cancer-resistant mice." Cell. 2008; 135(4):609-22.

Towbin et al., "Electrophoretic transfer of proteins from polyacrylamide gels to nitrocellulose sheets: Procedure and some applications." Proc. Natl. Acad. Sci. U. S. A. 1979, 76: 4350-4354.

Townsley et al., "Bone marrow failure and the telomeropathies." Blood. 2014, 124(18): 2775-2783.

Wright & Shay, "The two-stage mechanism controlling cellular senescence and immortalization." Exp Gerontol. 1992; 27(4):383-9.

|  |  | HEK293 | MDA_MB231 |
|---|---|---|---|
| LRP/LR | Surface | 75.26% | 99.17% |
|  | Intracellular | 72.22% | 98.82% |
| hTERT | Surface | 98.56% | 95.86% |
|  | Intracellular | 97.98% | 94.54% |

FIGURE 11e

SEQUENCE LISTING

```
<160> NUMBER OF SEQ ID NOS: 13

<210> SEQ ID NO 1
<211> LENGTH: 295
<212> TYPE: PRT
<213> ORGANISM: Homo sapiens

<400> SEQUENCE: 1

Met Ser Gly Ala Leu Asp Val Leu Gln Met Lys Glu Glu Asp Val Leu
1               5                   10                  15

Lys Phe Leu Ala Ala Gly Thr His Leu Gly Gly Thr Asn Leu Asp Phe
            20                  25                  30

Gln Met Glu Gln Tyr Ile Tyr Lys Arg Lys Ser Asp Gly Ile Tyr Ile
        35                  40                  45

Ile Asn Leu Lys Arg Thr Trp Glu Lys Leu Leu Leu Ala Ala Arg Ala
    50                  55                  60

Ile Val Ala Ile Glu Asn Pro Ala Asp Val Ser Val Ile Ser Ser Arg
65                  70                  75                  80

Asn Thr Gly Gln Arg Ala Val Leu Lys Phe Ala Ala Ala Thr Gly Ala
                85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
    130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Glu Lys Ala Val Thr Lys
    210                 215                 220
```

```
Glu Phe Gln Gly Glu Trp Thr Ala Pro Ala Pro Glu Phe Thr Ala
225                 230                 235                 240

Thr Gln Pro Glu Val Ala Asp Trp Ser Glu Gly Val Gln Val Pro Ser
            245                 250                 255

Val Pro Ile Gln Gln Phe Pro Thr Glu Asp Trp Ser Ala Gln Pro Ala
            260                 265                 270

Thr Glu Asp Trp Ser Ala Ala Pro Thr Ala Gln Ala Thr Glu Trp Val
            275                 280                 285

Gly Ala Thr Thr Asp Trp Ser
            290                 295

<210> SEQ ID NO 2
<211> LENGTH: 295
<212> TYPE: PRT
<213> ORGANISM: Mus musculus

<400> SEQUENCE: 2

Met Ser Gly Ala Leu Asp Val Leu Gln Met Lys Glu Glu Asp Val Leu
1               5                   10                  15

Lys Phe Leu Ala Ala Gly Thr His Leu Gly Gly Thr Asn Leu Asp Phe
            20                  25                  30

Gln Met Glu Gln Tyr Ile Tyr Lys Arg Lys Ser Asp Gly Ile Tyr Ile
        35                  40                  45

Ile Asn Leu Lys Arg Thr Trp Glu Lys Leu Leu Leu Ala Ala Arg Ala
    50                  55                  60

Ile Val Ala Ile Glu Asn Pro Ala Asp Val Ser Val Ile Ser Ser Arg
65                  70                  75                  80

Asn Thr Gly Gln Arg Ala Val Leu Lys Phe Ala Ala Ala Thr Gly Ala
                85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
    130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Glu Lys Ala Val Thr Lys
    210                 215                 220

Glu Glu Phe Gln Gly Glu Trp Thr Ala Pro Ala Pro Glu Phe Thr Ala
225                 230                 235                 240

Ala Gln Pro Glu Val Ala Asp Trp Ser Glu Gly Val Gln Val Pro Ser
            245                 250                 255

Val Pro Ile Gln Gln Phe Pro Thr Glu Asp Trp Ser Ala Gln Pro Ala
            260                 265                 270

Thr Glu Asp Trp Ser Ala Ala Pro Thr Ala Gln Ala Thr Glu Trp Val
            275                 280                 285

Gly Ala Thr Thr Glu Trp Ser
```

```
                    290                 295

<210> SEQ ID NO 3
<211> LENGTH: 8
<212> TYPE: PRT
<213> ORGANISM: Escherichia coli

<400> SEQUENCE: 3

Asp Tyr Lys Asp Asp Asp Asp Lys
1               5

<210> SEQ ID NO 4
<211> LENGTH: 194
<212> TYPE: PRT
<213> ORGANISM: Homo sapiens

<400> SEQUENCE: 4

Arg Phe Thr Pro Gly Thr Phe Thr Asn Gln Ile Gln Ala Ala Phe Arg
1               5                   10                  15

Glu Pro Arg Leu Leu Val Val Thr Asp Pro Arg Ala Asp His Gln Pro
            20                  25                  30

Leu Thr Glu Ala Ser Tyr Val Asn Leu Pro Thr Ile Ala Leu Cys Asn
        35                  40                  45

Thr Asp Ser Pro Leu Arg Tyr Val Asp Ile Ala Ile Pro Cys Asn Asn
    50                  55                  60

Lys Gly Ala His Ser Val Gly Leu Met Trp Met Leu Ala Arg Glu
65                  70                  75                  80

Val Leu Arg Met Arg Gly Thr Ile Ser Arg Glu His Pro Trp Glu Val
                85                  90                  95

Met Pro Asp Leu Tyr Phe Tyr Arg Asp Pro Glu Glu Ile Glu Lys Glu
            100                 105                 110

Glu Gln Ala Ala Ala Glu Lys Ala Val Thr Lys Glu Glu Phe Gln Gly
        115                 120                 125

Glu Trp Thr Ala Pro Ala Pro Glu Phe Thr Ala Thr Gln Pro Glu Val
    130                 135                 140

Ala Asp Trp Ser Glu Gly Val Gln Val Pro Ser Val Pro Ile Gln Gln
145                 150                 155                 160

Phe Pro Thr Glu Asp Trp Ser Ala Gln Pro Ala Thr Glu Asp Trp Ser
                165                 170                 175

Ala Ala Pro Thr Ala Gln Ala Thr Glu Trp Val Gly Ala Thr Thr Asp
            180                 185                 190

Trp Ser

<210> SEQ ID NO 5
<211> LENGTH: 194
<212> TYPE: PRT
<213> ORGANISM: Mus musculus

<400> SEQUENCE: 5

Arg Phe Thr Pro Gly Thr Phe Thr Asn Gln Ile Gln Ala Ala Phe Arg
1               5                   10                  15

Glu Pro Arg Leu Leu Val Val Thr Asp Pro Arg Ala Asp His Gln Pro
            20                  25                  30

Leu Thr Glu Ala Ser Tyr Val Asn Leu Pro Thr Ile Ala Leu Cys Asn
        35                  40                  45

Thr Asp Ser Pro Leu Arg Tyr Val Asp Ile Ala Ile Pro Cys Asn Asn
    50                  55                  60
```

```
Lys Gly Ala His Ser Val Gly Leu Met Trp Trp Met Leu Ala Arg Glu
 65                  70                  75                  80

Val Leu Arg Met Arg Gly Thr Ile Ser Arg Glu His Pro Trp Glu Val
                 85                  90                  95

Met Pro Asp Leu Tyr Phe Tyr Arg Asp Pro Glu Glu Ile Glu Lys Glu
            100                 105                 110

Glu Gln Ala Ala Ala Glu Lys Ala Val Thr Lys Glu Glu Phe Gln Gly
        115                 120                 125

Glu Trp Thr Ala Pro Ala Pro Glu Phe Thr Ala Ala Gln Pro Glu Val
    130                 135                 140

Ala Asp Trp Ser Glu Gly Val Gln Val Pro Ser Val Pro Ile Gln Gln
145                 150                 155                 160

Phe Pro Thr Glu Asp Trp Ser Ala Gln Pro Ala Thr Glu Asp Trp Ser
                165                 170                 175

Ala Ala Pro Thr Ala Gln Ala Thr Glu Trp Val Gly Ala Thr Thr Glu
            180                 185                 190

Trp Ser
```

<210> SEQ ID NO 6
<211> LENGTH: 20
<212> TYPE: DNA
<213> ORGANISM: Homo sapiens

<400> SEQUENCE: 6
acacaactgt gttcactagc                                                 20

<210> SEQ ID NO 7
<211> LENGTH: 20
<212> TYPE: DNA
<213> ORGANISM: Homo sapiens

<400> SEQUENCE: 7
caacttcatc cacgttcacc                                                 20

<210> SEQ ID NO 8
<211> LENGTH: 23
<212> TYPE: DNA
<213> ORGANISM: Homo sapiens

<400> SEQUENCE: 8
aggattctga tctctgaagg gtg                                             23

<210> SEQ ID NO 9
<211> LENGTH: 22
<212> TYPE: DNA
<213> ORGANISM: Homo sapiens

<400> SEQUENCE: 9
tctgcctgag gaaggacgta tg                                              22

<210> SEQ ID NO 10
<211> LENGTH: 39
<212> TYPE: DNA
<213> ORGANISM: Homo sapiens

<400> SEQUENCE: 10
tcccgactat ccctatccct atccctatcc ctatcccta                            39

<210> SEQ ID NO 11
<211> LENGTH: 39

```
<212> TYPE: DNA
<213> ORGANISM: Homo sapiens

<400> SEQUENCE: 11 ggtttttga gggtgagggt gaggggtgag ggtgagggt                    39

<210> SEQ ID NO 12
<211> LENGTH: 23
<212> TYPE: DNA
<213> ORGANISM: Homo sapiens

<400> SEQUENCE: 12
cagcaagtgg gaaggtgtaa tcc                                    23

<210> SEQ ID NO 13
<211> LENGTH: 25
<212> TYPE: DNA
<213> ORGANISM: Homo sapiens

<400> SEQUENCE: 13
cccattctat catcaacggg tacaa                                  25
```

COMPOUNDS FOR USE IN THE TREATMENT OF TELOMERE RELATED DISEASES AND/OR TELOMERE RELATED MEDICAL CONDITIONS

CROSS-REFERENCE TO RELATED APPLICATIONS

This application is a divisional of U.S. patent application Ser. No. 15/773,453, filed May 3, 2017, which is a national phase application under 35 U.S.C. § 371 of PCT International Application No. PCT/IB2016/056686, filed Nov. 7, 2016, which claims priority to Great Britain Application No. 1519557.1, filed Nov. 5, 2015, which are hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 10,365 Byte ASCII (Text) file named "36411-402-SQL_ST25.TXT," created on Feb. 17, 2021.

FIELD OF INVENTION

The field of this invention relates to compounds for use in the treatment of telomere related diseases and/or telomere related medical conditions. Particularly, this invention relates to compounds for use in the treatment of telomere related diseases and/or telomere related medical conditions, wherein the telomere related diseases and/or telomere related medical condition may be cellular ageing (cellular senescence) and/or cancer. The invention extends to pharmaceutical compositions comprising said compounds and a pharmaceutical carrier.

BACKGROUND

Telomerase is a ribonucleoprotein responsible for regulating proliferative potential and preventing senescence in tumorigenic, germline and immortalized cells (Kim et al., 1994). It is composed of two essential subunits, among others. In humans, these subunits include: hTERC, which contains a telomeric RNA template that the catalytic reverse transcriptase subunit hTERT reads (Nakamura and Cech, 1998). Together these subunits operate to extend telomeres in a 3'-5' direction (Nakamura and Cech, 1998). hTERT is the limiting factor for telomerase activity. This is due to its lower expression levels compared to hTERC, and thus, serves as the major regulator for telomerase activity. This said, telomerase fulfils its core function within the nucleus, where it elongates and maintains telomere length (Bodnar et al., 1998). This maintenance allows not only the continuation of normal cellular processes, but also improves the overall proliferative potential of cells (Bodnar et al., 1998).

Aside from telomere extension, telomerase/hTERT has extra-telomeric functions other than telomere maintenance. One such function is that hTERT may aid in regulating gene expression; especially genes of the Wnt and Myc pathway responsible for cell cycle initiation and proliferation (Cong and Shay, 2008). Furthermore, telomerase has been shown to play a role in mitochondrial protection against oxidative stress. This protective function is conveyed when cells are introduced to hypoxic stress, which causes the migration of nuclear hTERT to the mitochondria (Cong and Shay, 2008). Interestingly, aside from mitochondrial protection, hTERT may also play a role in mtDNA replication and repair (Sharma et al., 2012). Thus, the additional functions that hTERT/telomerase has been found to display, further highlight its vital presence in regulating and promoting cell viability.

The chromosomal ends that telomerase extends, known as telomeres, are composed of genomic TTAGGG repeats and associated protein structures (Harley and Villeponteau, 1995). These repeats and related proteins together "cap" linear eukaryotic chromosomes for protection. A few of these telomere-related proteins include TRF1, TRF 2 and POT1 (de Lange, 2005). These proteins interact with the telomeres and each other to form the "shelterin" complex. This complex facilitates the folding of telomeres to form a telomere loop (t-loop) to prevent telomere degradation (Griffith et al., 1999). This said, telomeres and their related proteins fulfil a vital function in protecting against genomic DNA damage. In addition, these telomeric structures also aid to distinguish between normal chromosomes and double stranded breaks (Harley and Villeponteau, 1995). This damage is caused by the imperfect replicating nature of DNA polymerase; that generates gaps during lagging strand synthesis (Harley et al., 1990). Additionally, DNA synthesis follows a unidirectional path (3' to 5'), resulting in DNA ends not being fully replicated, otherwise known as the "end replication problem" (Harley et al., 1990). Thus, telomeres as well as their extension prevent the loss of genetic information, ensuring genomic stability and in turn cell viability.

Telomeres are known to be involved in a number of diseases and/or medical conditions. The telomere related diseases and/or telomere related medical conditions may be, for example, at least one of, but not limited to, the following group: dyskeratosis congenital, cancer, cellular ageing (cellular senescence), idiopathic pulmonary fibrosis, Hoyeraal-Hreiderasson syndrome, Hutchinson-Gilford progeria, aplastic anemia and age-related diseases. Particularly relevant, owing to their great impact on the lives of humans, is cancer, cellular ageing (senescence) and age-related diseases. Age-related diseases may include osteoporosis, type II diabetes, atherosclerosis and cardiovascular disease.

There exists a need for new and inventive compounds, pharmaceutical compositions, and/or methods to treat and/or prevent telomere related diseases and/or telomere related medical conditions, particularly cancer and/or cellular ageing, and/or compounds for use in the treatment and/or prevention of telomere related diseases and/or telomere related medical conditions.

SUMMARY

Broadly, in accordance with this invention, there is provided a 37 kDa/67 kDa laminin receptor precursor/high affinity laminin receptor (LRP/LR) and/or a fragment thereof for use in the treatment and/or prevention of a telomere related disease and/or a telomere related medical condition, wherein LRP/LR and/or the fragment thereof being for administration to a subject in need thereof.

The use may be therapeutic and/or non-therapeutic. Non-therapeutic uses may include cosmetic uses. The telomere related disease and/or a telomere related medical condition may include ageing and/or cancer.

Therapeutic use may include use in the treatment and/or prevention of ageing and/or the impediment of cellular senescence and may include use wherein diseases and/or medical conditions relate to the irregular and/or abnormal and/or increased and/or early onset of cellular senescence in a human or animal including, but not limited to, the following group: dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease.

Non-therapeutic use may include use in the prevention and/or treatment and/or impeding of muscle degeneration, loss of bone mass, skin atrophy, hair loss, graying of hair and/or a loss of immune system efficacy.

LRP/LR may comprise a peptide/protein sequence listing as set forth in SEQ ID NO: 1 and/or SEQ ID NO: 2, or a fragment thereof as set forth in SEQ ID NO:4 and/or SEQ ID NO:5.

In accordance with a first aspect of the invention there is provided a 37 kDa/67 kDa laminin receptor precursor/high affinity laminin receptor (LRP/LR) and/or a fragment thereof for use in the impediment of cellular senescence, wherein LRP/LR and/or the fragment thereof being for administration to a subject in need thereof.

LRP/LR may comprise a peptide/protein sequence listing as set forth in SEQ ID NO: 1 or SEQ ID NO: 2, or a fragment thereof.

LRP/LR may comprise a peptide/protein sequence listing having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence listing as set forth in SEQ ID NO: 1 or SEQ ID NO: 2.

SEQ ID NO: 1 may be a peptide/protein sequence for human LRP/LR and may have the following sequence:

MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTATQPEVADWSE

GVQVPSVPIQQFPTEDWSAQPATEDWSAAPTAQATEWVGATTDWS

SEQ ID NO: 2 may be a peptide/protein sequence for mouse (*Mus musculus*) LRP/LR and may have the following sequence:

MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTAAQPEVADWSE

GVQVPSVPIQQFPTEDWSAQPATEDWSAAPTAQATEWVGATTEWS

It is to be understood that LRP/LR is highly conserved and homologs or fragments of SEQ ID NO: 1 and SEQ ID NO: 2, and/or homologs of the fragments may also utilized in order to exercise the invention described, illustrated and/or exemplified herein.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the protein sequence of LRP/LR may form part of a larger and/or longer protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide sequence that includes at least a sequence motif DYKDDDDK (SEQ ID NO: 3).

An example embodiment of a fragment of LRP/LR is exemplified as a protein/peptide having a sequence as set forth in SEQ ID NO: 4 corresponding to a fragment of SEQ ID NO:1 from amino acid residue 102 to amino acid residue 295 and/or SEQ ID NO:5 corresponding to a fragment of SEQ ID NO: 2 from amino acid residue 102 to amino acid residue 295.

SEQ ID NO:4 may be a peptide/protein sequence for a fragment of human LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

SEQ ID NO: 5 may be a peptide/protein sequence for a fragment of mouse LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGVQVPSVPIQQFPTEDWSAQ

PATEDWSAAPTAQATEWVGATTEWS

The impediment of senescence (cellular ageing) may be therapeutic and may treat and/or prevent at least one of, but not limited to, the following group of diseases: dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease. LRP/LR and/or a fragment thereof may be for use in the treatment of at least one of the following group of diseases; dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease. The use of LRP/LR and/or a fragment thereof may be therapeutic.

The impediment of senescence (cellular ageing) may be non-therapeutic and prevent and/or treat and/or impede muscle degeneration, loss of bone mass, skin atrophy, hair loss, graying of hair and/or a loss of immune system efficacy. The impediment of senescence (cellular ageing) may be cosmetic. The use of LRP/LR and/or a fragment thereof may be non-therapeutic and/or cosmetic.

There is provided for the peptide/protein having a sequence listing as set forth in SEQ ID NO: 4 and/or SEQ ID NO: 5 for use in the treatment of dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease.

Typically, in use the LRP/LR and/or a fragment thereof increases levels of hTERT and/or increases telomerase activity and/or increases telomere length and/or decreases senescent markers in at least one cell of the subject, therein impeding and/or treating and/or preventing cellular senescence (cellular ageing) of the at least one cell.

The subject may be a human, animal, reptile, avian, amphibian or plant. Typically, the subject may be a human and/or animal, preferably human.

The LRP/LR and/or a fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous.

In accordance with a second aspect of the invention there is provided a pharmaceutical composition comprising 37 kDa/67 kDa laminin receptor precursor/high affinity laminin receptor (LRP/LR) and/or a fragment thereof and a carrier, the pharmaceutical composition for use in the impediment of cellular senescence, wherein the pharmaceutical composition being for administration to a subject in need thereof.

LRP/LR may comprise a peptide/protein sequence listing as set forth in SEQ ID NO: 1 or SEQ ID NO: 2, or a fragment thereof.

LRP/LR may comprise a peptide/protein sequence listing having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence listing as set forth in SEQ ID NO: 1 or SEQ ID NO: 2.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the peptide/protein sequence of LRP/LR may form part of a larger and/or longer peptide/protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide sequence that includes at least a sequence motif DYKDDDDK (SEQ ID NO: 3).

An example embodiment of a fragment of the peptide/protein sequence listing is exemplified as SEQ ID NO: 4 corresponding to a fragment of SEQ ID NO:1 from 102 to 295 and/or SEQ ID NO:5 corresponding to a fragment of SEQ ID NO: 2 from 102 to 295.

SEQ ID NO:4 may be a peptide/protein sequence for a fragment of human LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

SEQ ID NO: 5 may be a peptide/protein sequence for a fragment of mouse LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGVQVPSVPIQQFPTEDWSAQ

PATEDWSAAPTAQATEWVGATTEWS

The impediment of senescence (cellular ageing) may be therapeutic and may treat and/or prevent at least one of, but not limited to, the following group of diseases: dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease. The use of LRP/LR and/or fragment thereof may be therapeutic.

The impediment of senescence (cellular ageing) may be non-therapeutic and prevent and/or treat and/or impede muscle degeneration, loss of bone mass, skin atrophy, hair loss, graying of hair and/or a loss of immune system efficacy. The impediment of senescence (cellular ageing) may be cosmetic. The use of LRP/LR and/or a fragment thereof may be non-therapeutic and/or cosmetic.

In use the pharmaceutical composition increases levels of hTERT and/or increases telomerase activity and/or increases telomere length and/or decreases senescent markers in at least one cell of the subject, therein impeding and/or treating and/or preventing senescence (cellular ageing) of the at least one cell.

The subject may be a human, animal, reptile, avian, amphibian or plant. Typically, the subject may be a human and/or animal, preferably human.

The pharmaceutical composition may be adapted for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous.

In accordance with a third aspect of the invention there is provided a method of increasing levels of hTERT and/or increasing telomerase activity and/or increasing telomere length and/or decreasing senescent markers in a cell of a human, animal or plant subject, the method comprising the following steps:
  (i) transfecting the cell to produce 37 kDa/67 kDa laminin receptor precursor/high affinity laminin receptor (LRP/LR) and/or a fragment thereof therein increasing cellular levels of LRP/LR and/or fragments thereof; or (ii) providing the cell with LRP/LR and/or fragments thereof to increase cellular levels of LRP/LR and/or fragments thereof,
wherein the increased levels of hTERT and/or increased telomerase activity and/or increased telomere length and/or decreased levels of senescent markers impedes and/or treats and/or prevents senescence (cellular ageing) of the cell in the subject.

LRP/LR may comprise a peptide/protein sequence listing as set forth in SEQ ID NO: 1 or SEQ ID NO: 2, or a fragment thereof.

LRP/LR may comprise a peptide/protein sequence listing having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence listing as set forth in SEQ ID NO: 1 or SEQ ID NO: 2.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the peptide/protein sequence of LRP/LR may form part of a larger and/or longer peptide/protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide/protein sequence that includes at least a sequence motif DYKDDDDK (SEQ ID NO:3).

It is to be understood that the step of transfecting the cell to produce 37 kDa/67 kDa laminin receptor precursor/high affinity laminin receptor (LRP/LR) and/or a fragment may take place via known procedures in the art, including introduction into the cell of a transfecting agent. The step of transfecting the cell may upregulate LRP/LR.

An example embodiment of a fragment of the peptide/ protein sequence listing is exemplified as SEQ ID NO: 4 corresponding to a fragment of SEQ ID NO:1 from 102 to 295 and/or SEQ ID NO:5 corresponding to a fragment of SEQ ID NO: 2 from 102 to 295.

SEQ ID NO: 4 may be a peptide/protein sequence for a fragment of human LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

SEQ ID NO: 5 may be a peptide/protein sequence for a fragment of mouse LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

-continued

AVTKEEFQGEWTAPAPEFTAAQPEVADWSEGVQVPSVPIQQFPTEDWSAQ

PATEDWSAAPTAQATEWVGATTEWS.

The method may be therapeutic. The impediment of cellular senescence (cellular ageing) may treat and/or prevent at least one of, but not limited to, the following group of diseases: dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease.

The method may be non-therapeutic and the impediment of senescence (cellular ageing) may be non-therapeutic and prevent and/or treat and/or impede muscle degeneration, loss of bone mass, skin atrophy, hair loss, graying of hair and/or a loss of immune system efficacy. The impediment of senescence (cellular ageing) may be cosmetic.

In use the LRP/LR and/or a fragment thereof increases levels of hTERT and/or increases telomerase activity and/or increases telomere length and/or decreases senescent markers in at least one cell of the subject, therein treating and/or preventing cellular senescence (cellular ageing) of the at least one cell.

The subject may be a human, animal, reptile, avian, amphibian or plant. Typically, the subject may be a human and/or animal, preferably human.

The LRP/LR and/or a fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous. Alternatively and/or additionally, the transfecting agent may be formulated into a pharmaceutical composition, wherein the pharmaceutical composition may further include a pharmaceutical carrier for parenteral or non-parenteral administration to the subject.

In accordance with a fourth aspect of the invention there is provided a method of treating and/or preventing and/or impeding cellular senescence, the method comprising the step of administering to a subject in need thereof 37 kDa/67 kDa laminin receptor precursor/high affinity laminin receptor (LRP/LR) and/or a fragment thereof, such that in use the LRP/LR and/or the fragment thereof increases levels of hTERT and/or increases telomerase activity and/or increases telomere length and/or decreases senescent markers in at least one cell of the subject, therein impeding and/or treating and/or preventing cellular senescence (cellular ageing) of the at least one cell.

LRP/LR may comprise a peptide/protein sequence listing as set forth in SEQ ID NO: 1 or SEQ ID NO: 2, or a fragment thereof.

LRP/LR may comprise a peptide/protein sequence listing having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence listing as set forth in SEQ ID NO: 1 or SEQ ID NO: 2.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the peptide/protein sequence of LRP/LR may form part of a larger and/or longer peptide/protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide/protein sequence that includes at least a sequence motif DYKDDDDK (SEQ ID NO: 3).

An example embodiment of a fragment of the peptide/protein sequence listing is exemplified as SEQ ID NO: 4 corresponding to a fragment of SEQ ID NO: 1 from 102 to 295 and/or SEQ ID NO:5 corresponding to a fragment of SEQ ID NO: 2 from 102 to 295.

SEQ ID NO: 4 may be a peptide/protein sequence for a fragment human LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

SEQ ID NO: 5 may be a peptide/protein sequence for a fragment of mouse LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGVQVPSVPIQQFPTEDWSAQ

PATEDWSAAPTAQATEWVGATTEWS

The method may be therapeutic. The impediment of cellular senescence (cellular ageing) may treat and/or prevent at least one of, but not limited to, the following group of diseases: dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease.

The method may be non-therapeutic and the impediment of senescence (cellular ageing) may be non-therapeutic and prevent and/or treat and/or impede of muscle degeneration, loss of bone mass, skin atrophy, hair loss, graying of hair and/or a loss of immune system efficacy. The impediment of senescence (cellular ageing) may be cosmetic.

The subject may be a human, animal, reptile, avian, amphibian or plant. Typically, the subject may be a human and/or animal, preferably human.

The LRP/LR and/or a fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous.

In all of the first to the fourth aspects of this invention senescent markers may be, but not limited to, the following group: β-galactosidase, progerin and H2AX foci.

In accordance with a fifth aspect of the invention there is provided an anti-37 kDa/67 kDa laminin receptor precursor/high affinity laminin receptor (anti-LRP/LR) specific antibody or fragment thereof for use in the treatment of cancer, wherein the anti-LRP/LR antibody being for administration to a subject in need thereof, and wherein binding of anti-LRP/LR specific antibody to a surface epitope of 37 kDa/67 kDa laminin receptor precursor/laminin receptor (LRP/LR) prevents interaction between LRP/LR and any one of hTERT and telomerase, which in turn decreases cellular levels of hTERT and/or decreases telomerase activity and/or decreases telomere length and in so doing prevents metastasis, promotes angiogenesis, and induces apoptosis, therein treating cancer.

LRP/LR may comprise a peptide/protein sequence listing as set forth in SEQ ID NO: 1 or SEQ ID NO: 2, or a fragment thereof. An example embodiment of a fragment of the peptide/protein sequence listing is exemplified as SEQ ID NO: 4 corresponding to a fragment of SEQ ID NO:1 from 102 to 295 and/or SEQ ID NO:5 corresponding to a fragment of SEQ ID NO: 2 from 102 to 295.

LRP/LR may comprise a peptide/protein sequence listing having at least 80% homology to the sequences as set forth in SEQ ID NO: 1 or SEQ ID NO: 2, or a fragment thereof.

The anti-LRP/LR specific antibody or fragment thereof may be at least one of, but not limited to, the following group: a F(ab')2 fragment, a Fab fragment scFv, a bi-specific scFv, a tri-specific scFv, a single chain or tandem diabody, a single domain antibody (dAb), a minibody and a molecular recognition unit (MRU).

The anti-LRP/LR specific antibody may be IgG1-iS18.

The subject may be a human, animal, reptile, avian, amphibian or plant. Typically, the subject may be a human and/or animal, preferably human.

The anti-LRP/LR specific antibody or fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous.

In accordance with a sixth aspect of the invention there is provided siRNA directed against 37 kDa/67 kDa laminin receptor precursor/high affinity laminin receptor (LRP/LR) or fragment thereof for use in the treatment of cancer, wherein the siRNA being for administration to a subject in need thereof for transfection in the subject to knockdown LRP/LR expression in the subject, and wherein knockdown of LRP/LR expression decreases cellular levels of hTERT and/or decreases telomerase activity and/or decreases telomere length and in so doing prevents metastasis, promotes angiogenesis, and induces apoptosis, therein treating cancer.

There is further provided for 37 kDa/67 kDa laminin receptor precursor/high affinity laminin receptor (LRP/LR) and/or a fragment thereof for use in impediment of cellular senescence (cellular ageing), substantially as herein described, illustrated and/or exemplified with reference to any one of the examples and/or figures.

There is further provided for a pharmaceutical composition substantially as herein described, illustrated and/or exemplified with reference to any one of the examples and/or figures.

There is further provided for a method of increasing levels of hTERT and/or increasing telomerase activity and/or increasing telomere length in a cell of a human, animal or plant subject, the method substantially as herein described, illustrated and/or exemplified with reference to any one of the examples and/or figures.

There is further provided for a method of treating and/or preventing and/or impeding cellular senescence substantially as herein described, illustrated and/or exemplified with reference to any one of the examples and/or figures.

There is further provided for anti-37 kDa/67 kDa laminin receptor precursor/high affinity laminin receptor (anti-LRP/LR) specific antibody or fragment thereof for use in the treatment of cancer, substantially as herein described, illustrated and/or exemplified with reference to any one of the examples and/or figures.

There is further provided for siRNA directed against 37 kDa/67 kDa laminin receptor precursor/high affinity laminin receptor (LRP/LR) for use in the treatment of cancer, substantially as herein described, illustrated and/or exemplified with reference to any one of the examples and/or figures.

BRIEF DESCRIPTION OF THE DRAWINGS

Embodiments of the disclosure will be described below by way of example only and with reference to the accompanying drawings in which:

FIG. 11E show the results from 11A to 11D tabulated for ease of reference;

DETAILED DESCRIPTION OF THE INVENTION

Figure 1A:
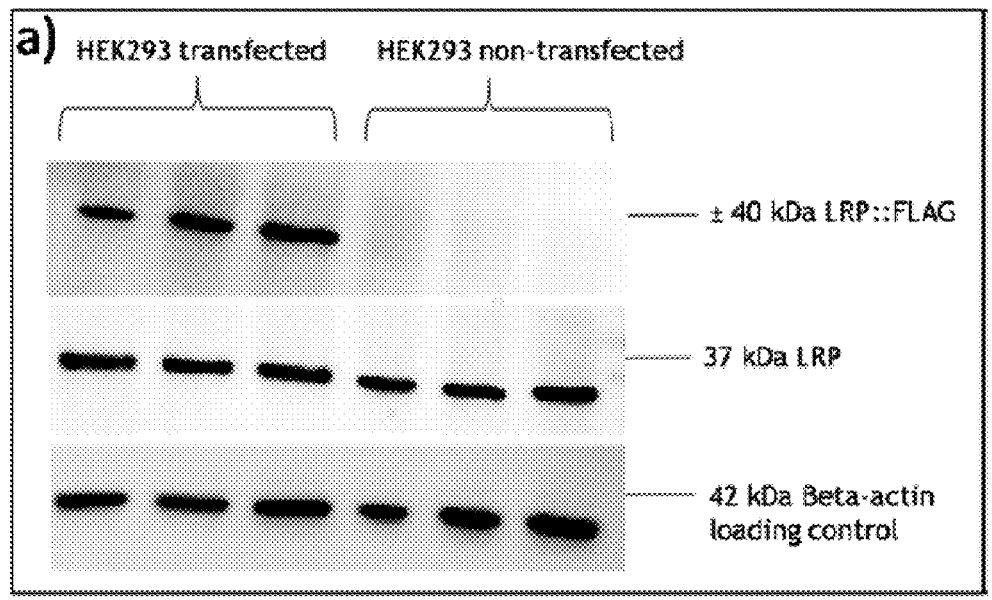
FIG. 1A shows overexpression of LRP::FLAG in HEK293 cells transfected with the pCIneo-LRP-FLAG plasmid.

In accordance with a first aspect of the invention there is provided a 37 kDa/67 kDa laminin receptor precursor/high affinity laminin receptor (LRP/LR) and/or a fragment thereof for use in the treatment and/or prevention of a telomere related disease and/or a telomere related medical condition, typically cellular senescence, wherein LRP/LR and/or the fragment thereof being for administration to a subject in need thereof. The LRP/LR may comprise a peptide/protein sequence listing as set forth in SEQ ID NO: 1 or SEQ ID NO: 2, or a fragment thereof, such as the fragment having a sequence listing as set forth in SEQ ID NO:4 and/or SEQ ID NO:5. Alternatively and/or additionally, the LRP/LR may comprise a peptide/protein sequence listing having at least 80% homology to the sequences as set forth in SEQ ID NO: 1 or SEQ ID NO: 2 or SEQ ID NO: 4 or SEQ ID NO:5, or a fragment thereof. Further still, the LRP/LR may comprise homologs or fragments thereof, and homologs of the fragments, wherein LRP/LR may comprise a peptide/protein sequence listing as set forth in SEQ ID NO: 1 or SEQ ID NO: 2 or SEQ ID NO: 4 or SEQ ID NO:5.

SEQ ID NO: 1 may be a peptide/protein sequence for human LRP/LR and may have the following sequence:

MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTATQPEVADWSE

GVQVPSVPIQQFPTEDWSAQPATEDWSAAPTAQATEWVGATTDWS

SEQ ID NO: 2 may be a peptide/protein sequence for mouse (*Mus musculus*) LRP/LR and may have the following sequence:

MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTAAQPEVADWSE

GVQVPSVPIQQFPTEDWSAQPATEDWSAAPTAQATEWVGATTEWS

It is to be understood that LRP/LR is highly conserved and homologs or fragments of SEQ ID NO: 1 and SEQ ID NO: 2, and/or homologs of the fragments may also utilized in order to exercise the invention described, illustrated and/or exemplified herein.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the peptide/protein sequence of LRP/LR may form part of a larger and/or longer protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide/protein sequence that includes at least a sequence motif DYKDDDDK (SEQ ID NO: 3). FLAG is used to aid in evaluation and/or quantification and/or interpretation of the experiments below in the Examples section. Although used in the Examples, it is not necessary in order to exercise the claimed invention. However, a person skilled in the art may want to include a tag such as FLAG.

An example embodiment of a fragment of LRP/LR is exemplified as a protein/peptide having a sequence as set forth in SEQ ID NO: 4 corresponding to a fragment of SEQ ID NO: 1 from amino acid residue 102 to amino acid residue 295 and/or SEQ ID NO:5 corresponding to a fragment of SEQ ID NO: 2 from amino acid residue 102 to amino acid residue 295.

SEQ ID NO: 4 may be a peptide/protein sequence for a fragment of human LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

SEQ ID NO: 5 may be a peptide/protein sequence for a fragment of mouse LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGVQVPSVPIQQFPTEDWSAQ

PATEDWSAAPTAQATEWVGATTEWS.

The impediment of cellular senescence (cellular ageing) may be therapeutic and may treat and/or prevent at least one of, but not limited to, the following group of diseases: dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease. The use of LRP/LR and/or a fragment thereof may be therapeutic. Typically, telomere related disease and/or telomere related medical condition may be cellular ageing of the subject, and in use the LRP/LR and/or a fragment thereof increases levels of hTERT and/or increases telomerase activity and/or increases telomere length and/or decrease senescence markers in at least one cell of the subject, therein treating and/or preventing ageing of the at least one cell.

The impediment of senescence (cellular ageing) may be non-therapeutic and prevent and/or treat and/or impede of muscle degeneration, loss of bone mass, skin atrophy, hair loss, graying of hair and/or a loss of immune system efficacy. The impediment of senescence (cellular ageing) may be cosmetic. The use of LRP/LR and/or a fragment thereof may be non-therapeutic and/or cosmetic.

The subject may be a human, animal, reptile, avian, amphibian or plant. Typically, the subject may be a human and/or animal, preferably human.

The LRP/LR and/or a fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous.

In accordance with a second aspect of the invention there is provided a pharmaceutical composition comprising 37 kDa/67 kDa laminin receptor precursor/high affinity laminin receptor (LRP/LR) and/or a fragment thereof and a carrier, the pharmaceutical composition for use in the impediment of cellular senescence, wherein the pharmaceutical composition being for administration to a subject in need thereof. Details as to LRP/LR, the type of telomere related disease and/or a telomere related medical condition, the subject and/or a pharmaceutical composition comprising LRP/LR, are as per above in the first aspect of the invention.

In accordance with a third aspect of the invention there is provided a method of increasing levels of hTERT and/or increasing telomerase activity and/or increasing telomere length in a cell of a human, animal or plant subject, the method comprising the following steps:
(i) transfecting the cell to produce 37 kDa/67 kDa laminin receptor precursor/high affinity laminin receptor (LRP/LR) and/or a fragment thereof therein increasing cellular levels of LRP/LR and/or fragments thereof; or
(ii) providing the cell with LRP/LR and/or fragments thereof to increase cellular levels of LRP/LR and/or fragments thereof,
wherein the increased levels of hTERT and/or increased telomerase activity and/or increased telomere length treats and/or prevents ageing of the cell in the subject.

As explained elsewhere the method may be therapeutic and/or non-therapeutic.

It is to be understood that the step of transfecting the cell to produce 37 kDa/67 kDa laminin receptor precursor/high affinity laminin receptor (LRP/LR) and/or a fragment may take place via known procedures in the art, including introduction into the cell of a transfecting agent. The step of transfecting the cell may upregulate LRP/LR. Details as to LRP/LR, the type of telomere related disease and/or a telomere related medical condition, the subject and/or a pharmaceutical composition comprising LRP/LR, are as per above in the first aspect of the invention.

In accordance with a fourth aspect of the invention there is provided a method of treating and/or preventing a telomere related disease and/or a telomere related medical condition, typically cellular senescence, the method comprising the step of administering to a subject in need thereof 37 kDa/67 kDa laminin receptor precursor/high affinity laminin receptor (LRP/LR) and/or a fragment thereof, such that in use the LRP/LR and/or the fragment thereof increases levels of hTERT and/or increases telomerase activity and/or increases telomere length in at least one cell of the subject, therein treating and/or preventing ageing of the at least one cell. Details as to LRP/LR, the type of telomere related disease and/or a telomere related medical condition, the subject and/or a pharmaceutical composition comprising LRP/LR, are as per above in the first aspect of the invention. As explained elsewhere the method may be therapeutic and/or non-therapeutic.

In accordance with a fifth aspect of the invention there is provided an anti-37 kDa/67 kDa laminin receptor precursor/high affinity laminin receptor (anti-LRP/LR) specific antibody or fragment thereof for use in the treatment of cancer, wherein the anti-LRP/LR antibody being for administration to a subject in need thereof, and wherein binding of anti-LRP/LR specific antibody to a surface epitope of 37 kDa/67 kDa laminin receptor precursor/laminin receptor (LRP/LR) prevents interaction between LRP/LR and any one of hTERT and telomerase, which in turn decreases cellular levels of hTERT and/or decreases telomerase activity and/or decreases telomere length and in so doing prevents metastasis, promotes angiogenesis, and induces apoptosis, therein treating cancer.

Details as to LRP/LR, the type of telomere related disease and/or a telomere related medical condition, the subject and/or a pharmaceutical composition comprising LRP/LR, are as per above in the first aspect of the invention.

The anti-LRP/LR specific antibody or fragment thereof may be at least one of, but not limited to, the following group: a F(ab')2 fragment, a Fab fragment scFv, a bi-specific scFv, a tri-specific scFv, a single chain or tandem diabody, a single domain antibody (dAb), a minibody and a molecular recognition unit (MRU). The anti-LRP/LR specific antibody may be IgG1-iS18.

In accordance with a sixth aspect of the invention there is provided siRNA directed against 37 kDa/67 kDa laminin receptor precursor/high affinity laminin receptor (LRP/LR) or fragment thereof for use in the treatment of cancer, wherein the siRNA being for administration to a subject in need thereof for transfection in the subject to knockdown LRP/LR expression in the subject, and wherein knockdown of LRP/LR expression decreases cellular levels of hTERT and/or decreases telomerase activity and/or decreases telomere length and in so doing prevents metastasis, promotes angiogenesis, and induces apoptosis, therein treating cancer. Details as to LRP/LR, the type of telomere related disease and/or a telomere related medical condition, the subject and/or a pharmaceutical composition comprising LRP/LR, are as per above in the first aspect of the invention.

Specific, but non-limiting embodiments of the invention will now be described. The various aspects of the invention as per the Summary above is repeated herein by reference thereto.

EXAMPLES

The Examples here below serve to further exemplify the invention and are non-limiting in their scope.

Example 1—Compounds for Use in the Impediment of Cellular Senescence

List of Abbreviations cDNA Complimentary Deoxyribonucleic Acid
DAPI 4',6-diamidino-2-phenylindole
DNA Deoxyribonucleic Acid
dNTP Deoxynucleotide Triphosphates
dsDNase Double Stranded Deoxyribonuclease
HEK293 Human Embryonic Kidney Cells
hTERT Human Telomerase Reverse Transcription
kDa Kilo Dalton
LRP/LR 37 kDa Laminin Receptor Precursor/67 kDa High affinity Laminin Receptor
DMEM Dulbecco's Modified Eagle's Medium
MRC 5 Human lung fibroblasts
mtDNA Mitochondrial Deoxyribonucleic Acid
PAGE Polyacrylamide Gel electrophoresis
PCR Polymerase Chain Reaction
POT1 Protection of telomeres Protein 1
qPCR Quantitative Polymerase Chain Reaction
Rb Retinoblastoma
RNA Ribonucleic Acid
RNase Ribonuclease
ROS Reactive Oxygen Species
SDS Sodium Dodecyl Sulphate
shRNA Small Hairpin RNA
siRNA Small Interfering RNA
TERC Telomerase RNA Component
t-loop Telomere-loop
TRF1 TTAGGG Repeat Binding Factor 1
TRF2 TTAGGG Repeat Binding Factor 2
X-Gal 5-bromo-4-chloro-3-indolyl-beta-D-galacto-pyranoside Experimental Procedure (Example 1)

Cell Culture:

Cell culture provides an in vitro model system that attempts to mimic the environmental conditions in which cells proliferate. This system allows for the investigation of the genetic, biochemical and biological processes of cells. Non-tumorigenic, Human embryonic kidney cells (HEK 293) were used due to their detectable levels of telomerase activity. HEK 293 cell lines were obtained from ATCC. Human lung fibroblasts (MRC 5) (Fox Chase Cancer Centre) were used as a cellular senescence model due to low or undetectable levels of TERT and limited replications before reaching senescence. All cell lines were cultured in 5% $CO_2$ at 37° C. to provide optimal proliferation conditions. The cell lines were maintained in Dulbecco's modified Eagle's medium (DMEM) high glucose (4.5 g/l) containing 4 mM L-Glutamine and, further supplemented with 10% foetal bovine serum (FBS) and 1% penicillin/streptomycin.

Cells were split when they reached an appropriate confluency. Prior to splits cells were washed with PBS, followed by incubating with 1 ml of trypsin at 37° C. for 10 minutes. Thereafter, 9 ml of media was added and cells split in a 1:20 ratio. The split cells had new media added to make up 10 ml again.

LRP/LR Mediated Upregulation by Transfection Using an LRP Flag Construct:

Transfections were performed to induce an overexpression of the LRP::FLAG protein (LRP as per SEQ ID NO: 2 and FLAG as per SEQ ID NO: 3), to elevate total levels of LRP/LR within the cell (Vana and Weiss, 2006). The procedure consisted of culturing cells until a 60% confluency was obtained. Transfection was undertaken using Lipofectamine 3000, and followed the manufacturer's protocol. This transfection procedure was utilised over others due to its high transfection efficiency and it has been utilised in a number of studies. Briefly, a mixture of 250 µl Optimem, 5 µl/ml of the flag construct (pCIneo-molLRP::FLAG), 56.1 µl p3000 and 56.1 µl of the Lipofectamine reagent were used. This was incubated at room temperature for 10-15 minutes, to allow the formation of lipophilic complexes around the DNA construct. Cells were treated with 250 µl of the Lipofectamine mix prior to incubating overnight. Thereafter, a media change was performed and cells were allowed to proliferate for two days. This was performed so that cells had sufficient time to produce the LRP::FLAG protein and selectable marker, before selective treatment commenced with genetocin. The cell lines were administered an initial treatment of 8000 ng/µl for one week, to ensure that only cells containing the plasmid remained. Thereafter, cells were treated throughout the experiment with 3000 ng/µl in order to ensure that a stable transfection and expression of the LRP::FLAG was maintained.

Bicinchoninic Acid™ (BCA) Protein Assay:

BCA assays, an essential prerequisite to western blotting were performed for the quantification of protein lysate samples to ensure equal protein concentrations were used. The procedure involved lysing cells with a lysis buffer, after which cell lysates were harvested. Thereafter, protein/cell lysate was incubated with a mixture of Bicinchoninic acid and copper sulphate. A standard curve was constructed using Bovine serum albumin (BSA) of a known concentration and constructing a serial dilution (1:10) from 100 mg/ml to 0 mg/ml. The standard curve was then used to extrapolate the total protein concentration of the cell lines. The assay worked by reducing $Cu^{2+}$ to $Cu^+$, which is caused by the peptide bonds present in the protein samples. This reaction resulted in a colorimetric change from the reduction of $Cu^+$. This was measured at 562 nm, and protein concentrations were calculated from the standard curve.

Western Blotting and SDS-PAGE:

Sodium Dodecyl sulphate polyacrylamide gel electrophoresis (SDS-PAGE) is a commonly used procedure to assess the approximate size of a particular protein (Towbin et al., 1979). Thereafter, the protein is transferred from the gel to a membrane for western blotting. Western blotting utilises specific antibodies to immunologically detect, identify and quantify protein levels (Towbin et al., 1979). The technique was used to confirm that cells were successfully transfected and expressing the LRP::FLAG protein, where LRP/LR was also assessed. Apart from confirming the presence of the LRP::FLAG, western blotting was also used for the relative quantification of hTERT levels as well as the senescent markers (for example β-galactosidase, progerin and/or HA2X foci).

The procedure was performed using 10 μg/ml of protein lysate for beta actin, LRP/LR and the LRP flag protein. As opposed to 50 μg/ml of protein used for progerin and hTERT detection, respectively. SDS PAGE was then used to separate the proteins according to size. Thereafter, separated proteins were transferred onto a polyvinylidene fluoride membrane. This was performed using a 1× transfer buffer and a semi-dry transferring apparatus that was run for 50 minutes at 350 mV. The membrane was then blocked in 3% BSA in 1×PBS Tween solution, for an hour to prevent non-specific binding of the antibodies. The membranes were then incubated with primary antibody overnight. Thereafter, three washes in PBS Tween were performed to remove unbound antibodies. The appropriate secondary antibody coupled with a horseradish peroxidase enzyme (HRP) was then incubated for an hour, followed by three washes. After the last wash, membranes were incubated with a chemiluminescent substrate (Thermo scientific), which the HRP enzyme reacted with to form a precipitate. This precipitate was then detected by radiation exposure. Experiments were performed in triplicates, with all antibodies and concentrations used in Table 1.

TABLE 1

List of primary and secondary antibodies with concentrations, for Western blotting; Co-immunoprecipitation and Confocal microscopy.

| Target Protein | Primary antibody | Secondary antibody | Experiment | Dilution factor for both antibodies |
|---|---|---|---|---|
| LRP/LR | Human anti-LRP/LR IgG-iS18 (Affimed) | anti-human IgG-HRP (Abcam 6858) | Western blotting; FLAG® Co-immunoprecipitation | 1:6500 |
| LRP/LR | Human anti-LRP/LR IgG-iS18 (Affimed) | anti-human IgG-FITC (Abcam 6854) | Confocal Microscopy | 1:100 |
| LRP::FLAG | Murine anti-FLAG (Sigma F-3165) | anti-murine IgG-HRP (Sigma A4416) | Western blotting; FLAG® Co-immunoprecipitation | 1:4000 |
| LRP::FLAG | Murine anti-FLAG (Sigma F-3165) | anti-murine IgG-FITC (Abcam 6785) | Confocal Microscopy | 1:100 |
| hTERT | Rabbit anti-hTERT (abcam 183105) | anti-rabbit IgG-HRP (Cell signalling 7074S) | Western blotting; FLAG® Co-immunoprecipitation | 1:1000 |
| hTERT | Rabbit anti-hTERT (Abcam 183105) | anti-rabbit IgG-APC (Abcam 72567) | Confocal Microscopy | 1:100 |
| β-actin | Murine anti-β-actin-peroxidase. (Sigma A3854) | — | Western blotting | 1:10 000 |
| Progerin | Murine anti-progerin (Abcam 13A) | anti-murine IgG-HRP (Sigma A4416) | Western blotting | 1:1000 |
| BAP FLAG fusion protein | Murine anti-FLAG (Sigma F-3165) | anti-murine IgG-HRP (Sigma A4416) | FLAG® Co-immunoprecipitation | 1:4000 |
| H2AX | Rabbit anti-Phospho-H2AFX (PSER 139) (Sigma SAB4300213) | Anti-rabbit IgG74S)-HRP (Cell signaling 70 | Western Blotting | 1:1000 |

Confocal Microscopy:

Confocal microscopy, an advanced form of immunofluorescent microscopy allows the visualization of a protein's localization within cells. Additionally, this method is also used to illustrate the co-localization of two proteins. This particular procedure was utilized to determine the extent of co-localization between LRP/LR and hTERT. These proteins were assessed intracellularly, for both non-transfected and transfected HEK293 and MRC 5 cells. Firstly, cells were seeded onto coverslips and cultured until a 70% cell confluency was reached. The cells were then fixed in a solution of 4% paraformaldehyde for 20 minutes, followed by three washes in PBS. In order to observe intracellular localization of the proteins, cells were permeabilized in a solution of Triton X in PBS for 15 minutes. Thereafter, one wash was performed with PBS followed by a blocking step. This was to prevent non-specific binding of the antibody using 1 ml of 0.05% BSA in PBS and, incubated for 10 minutes. Thereafter, coverslips were incubated overnight with the primary antibodies for LRP/LR (1:100) and hTERT [(1:100) (Table 1)]. Prior to the hour-long incubation with the secondary antibody, coverslips were washed three times. Secondary antibodies included a fluorescent FITC-coupled and APC-coupled secondary antibody at a 1:100 dilution in 0.5% BSA (For specific antibodies used refer to Table 1). This allowed florescent detection of the specific proteins of interest (Miller and Shakes, 1995). Thereafter, coverslips were washed three times and incubated for 10 minutes in Hoesht stain for nuclear staining. Finally, cover slips were washed and mounted onto clean microscope slides using Gelmount (Sigma-Aldrich). The slides were viewed with the Zeiss LSM 780 confocal microscope at 450× and 630× magnification, respectively.

FLAG® Co-Immunoprecipitation Assay (Pull Down Assay):

To determine if LRP/LR and hTERT shared an interaction, a modified procedure using the FLAG® Immunoprecipitation Kit (Sigma-Aldrich) was used. This particular assay was used, as the Anti-FLAG M2 beads used specifically binds the FLAG peptide, which was present on LRP::FLAG produced in HEK293 transfected cells. Firstly, cell lysates were incubated in Eppendorf tubes containing the Anti-FLAG M2 beads, overnight at 4° C. Additionally, a negative control (lysis buffer only) and a positive control comprised of the BAP FLAG fusion protein were also run. Thereafter, beads were washed three times with a 1× wash buffer provided in the kit. This was to remove any unbound protein from the beads. Washes and unbound protein samples from both transfected and non-transfected were collected as they contained unbound protein from the beads. Post washing, beads were boiled in sample buffer provided in the kit, to remove the beads and separate any bound proteins. All collected protein fractions were then resolved by western blotting. All respective primary and secondary antibodies used as well as their protein targets and concentrations are outlined in Table 1.

β-Galactosidase Assays:

The senescent marker β-galactosidase was chosen, as it is one of the most widely used senescent markers in ageing studies. Furthermore, its levels only increase in senescent or nutrient-starved cells, allowing for efficient/simpler detection. Two assays were utilised to assess the levels and activity of β-galactosidase, namely: the Senescence β-Galactosidase Staining kit (Cell Signalling) and the β-Galactosidase Enzyme Assay System with Reporter Lysis Buffer (Promega). The Senescence β-Galactosidase Staining kit stains senescent cells blue that have senescence-associated β-galactosidase activity at pH 6. Briefly, cells were cultured in six well plates and supplemented with fresh media. Cells were cultured until a 50% confluency was reached cells. Cells washed in 1×PBS and fixed to the plate by a 1× fixative solution provided in the kit for 15 minutes at room temperature. Thereafter, cells were washed twice and incubated with the made up staining solution of X-gal (reagents provided in kit) overnight at 37° C. Cells were then observed by light microscopy and images taken. These were used to compare qualitatively the quantity of blue stained senescent cells between transfected and non-transfected HEK293 and MRC 5 cells. The procedure was performed in triplicates for both transfected and non-transfected HEK293 and MRC 5 cells.

An altered form of the reporter lysis assay was used, as the assay is normally used to detect the activity of a plasmid reporter gene β-galactosidase activity. However, the kit does require normalisation against endogenous β-galactosidase activity, due to its detection. Therefore only endogenous levels of β-galactosidase activity were tested for. Briefly, cell lysates were prepared by incubating pelleted cells in a lysis buffer provided in the kit. Thereafter, a BCA assay was performed to ensure equal concentrations of protein was used. Lysates were incubated in 96 plates with Assay buffer and allowed to react for three hours. A negative control was also run consisting of lysis buffer and assay buffer only. Afterwards sodium carbonate was added to stop the reaction and the plate was read at 420 nm in an ELISA reader. The procedure was run in a set of triplicates with three biological repeats for both transfected and non-transfected HEK293 and MRC 5 cells.

Detection of Telomerase Activity:

The telomerase activity of the cells was detected with the use of the TRAPEZE Merck Telomerase Detection kit (Merck Millipore) and real time PCR (qPCR). The procedure measured the relative activity of telomerase in an enzymatically active cell sample. The assay was selected as the use of PCR amplification heightens sensitivity, allowing for easier detection of telomerase activity (Kim et al., 1994). The procedure involved harvesting fresh cell pellets washed in PBS. These pelleted cells were re-suspended and lysed in 200 μl of CHAPS lysis buffer and incubated for 30 minutes on ice. Thereafter, the supernatant containing the extracted protein was collected by centrifugation at 12000 g for 20 minutes at 4° C. The collected supernatant was then transferred to a fresh Eppendorf tube and quantified by Nanodrop at 280 nm. This ensured that equal concentrations of 500 ng/μl were utilised for all samples. The relative telomerase activity was then quantified through qPCR. All data was extrapolated from a standard curve generated by a serial dilution (1:10) of TSR8 from 20 amoles to 0.2 amoles. The procedure was run with a positive control consisting of cell extract known to have telomerase activity. In addition, four forms of negative controls were also included. The negative controls consisted of a no template control with just water and reaction mix, another of just CHAPs lysis buffer in the mix. The third negative control consisted of protein samples of the different cell lines that had been heat treated at 85° C. for 10 minutes in order to deactivate telomerase. The final negative control contained unaltered protein lysate of the samples, however it was incubated with TSK; a telomerase inhibitor. All samples were mixed with a reaction master mix containing the necessary dNTPs, $MgCl_2$, buffer and the Taq polymerase. The qPCR reaction was then performed in the Roche Lightcycler 480. The first step (pre-incubation) at 37° C. was used to promote the elongating action of telomerase to add telomeric repeats for 30 minutes. Thereafter, the temperature was brought up to 95° C. for a period of 2 minutes to denature the double stranded DNA and activate the Taq polymerase. The cycling parameters used to amplify the extended telomeres included 45 cycles of the following steps: Denaturation step at 94° C. for 15 seconds, followed by an annealing step for 60 seconds at 59° C. Lastly extension was allowed to occur at 45° C. for 20 seconds where the Lightcycler 480 performed the reads for quantification. The reads generated were then used to quantify the relative activity of telomerase.

Assessment of Telomere Length:

The relative telomere length was assessed by qPCR as per Cawthon (2002). This method was utilised to assess changes in relative telomere length, accompanying telomerase upregulation. The procedure involved extracting DNA from harvested cell pellets using the Gene Jet DNA extraction kit and following the manufacturer's instructions. Briefly, this involved incubating harvested cell pellets in a mixture of TE buffer, lysis solution and proteinase K for 10 minutes. Thereafter, RNase was added and allowed to incubate for an additional 10 minutes. Following this, lysate was mixed with 50× ethanol and transferred to a purification column. Lysates were then washed twice and DNA was eluted with an elution buffer. DNA samples were amplified by gradient PCR for the hTERT mini-satellite (MNS16A) and reference gene β-globin. This was to ensure that samples were amplifiable prior to qPCR.

After ensuring DNA samples were amplifiable; qPCR of the reference gene 36B4 was carried out. This was to normalize the data obtained for telomere length to the reference gene in order to correct sample-to-sample variations, and ensure accuracy in the quantification data obtained. Once the reference gene had been analysed qPCR was performed for telomere length. The procedure consisted of the construction of a standard curve using DNA of a known concentration and performing serial dilutions (1:10) from 35 ng/µl to 0.035 ng/µl. The reaction was run with a set of positive and negative controls, where the negative control was a no template control (No DNA sample was loaded). The positive control was DNA samples that were previously confirmed to amplify. The experimental samples were loaded in six-couplets with the reaction performed in the Roche Lightcycler 480 (Germany) under the following cycling parameters: an initial denaturation step at 95° C. for 10 minutes followed by 45 amplification cycles. These cycles included: Denaturation at 95° C. for 10 seconds followed by an annealing step at 58° C. for 10 seconds with the final step being extension (where signal was detected and read) at 72° C. for 60 seconds. The amplification readings for the experimental samples were then normalized to the standard curve and analysed.

TABLE 2

List of primers utilised for all telomere length PCR related procedures

| Primer name | 5'-3' sequence | Amplified Region | References |
|---|---|---|---|
| β-globin | ACACAACTGTGTTCACTAGC (Forward) <br> CAACTTCATCCACGTTCACC (Reverse) | β-globin | Saiki et al., 1998 |
| MNS16A | AGGATTCTGATCTCTGAAGGGTG (Forward) <br> TCTGCCTGAGGAAGGACGTATG (Reverse) | MNS16A satellite | Wang et al., 2003 |
| Telomere length | TCCCGACTATCCCTATCCCTATCCCTATCCCTATCCC TA (Forward) <br> GGTTTTTTGAGGGTGAGGGTGAGGGTGAGGGTGAG GGT (Reverse) | End of telomere | Cawthon et al., 2002 |
| 36B4 | CAGCAAGTGGGAAGGTGTAATCC (Forward) <br> CCCATTCTATCATCAACGGGTACAA (Reverse) | 36B4 | Cawthon et al., 2002 |

Statistical Evaluations:

All statistical evaluations of the data were carried out using Microsoft Excel 2014 (Microsoft Corporation), and Graph Prism Version 5 (Graphpad Software, Inc). These evaluations were carried out to ensure that the results collected were significantly relevant. All experiments were performed in triplicates so that standard deviation could be calculated. The two-tailed Student's t-test was performed at a 95% confidence interval; where values $p>0.05$ considered significant.

Results (Example 1)

Figure 1B:
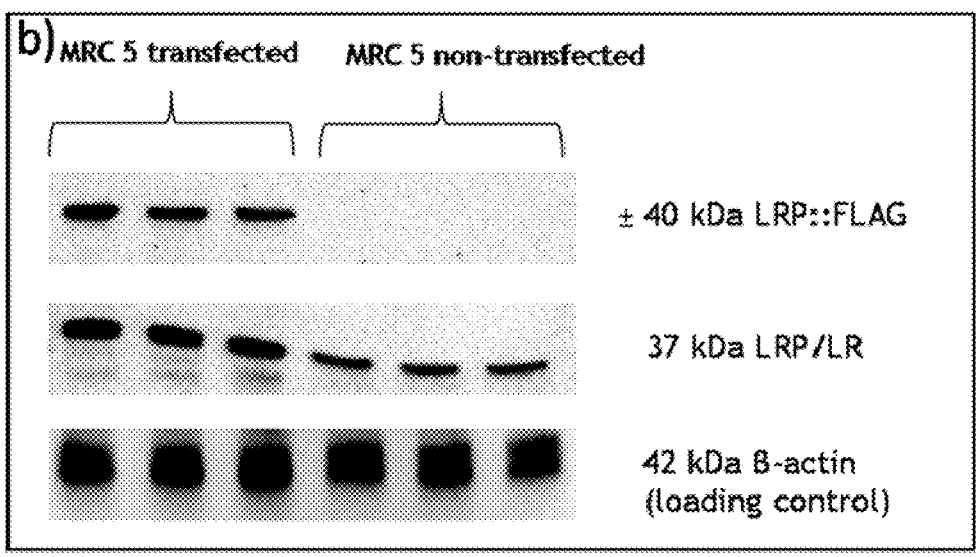
FIG. 1B shows overexpression of LRP::FLAG in MRC 5 cells transfected with the pCIneo-LRP-FLAG plasmid.

Human Embryonic Kidney Cells and Human Lung Fibroblasts Transfected to Overexpress LRP::FLAG:

In order to assess whether LRP/LR could potentially play a role in cellular senescence (and the ageing process of cells) and affect hTERT/telomerase levels, HEK293 and MRC 5 cells were stably transfected with a pCIneo LRP::FLAG plasmid. This was done in order to induce an overexpression of LRP::FLAG and increase total LRP/LR within the cells. Western blotting was then incorporated to confirm a stable transfection of the cells. It was illustrated in FIGS. 1A and 1B that LRP/LR and β-actin were detected for both non-transfected and transfected HEK293 and MRC 5 cell lines, respectively. Additionally the presence of the LRP::FLAG protein was only detected in the transfected HEK293 and MRC 5 cell lines, and indicated a successful transfection and overexpression of LRP::FLAG (illustrated in lanes 4-6 in FIGS. 1A and 1B). FIGS. 1A and 1B show overexpression of LRP::FLAG in HEK293 and MRC 5 cells transfected with the pCIneo-LRP-FLAG plasmid.

Figure 2A:
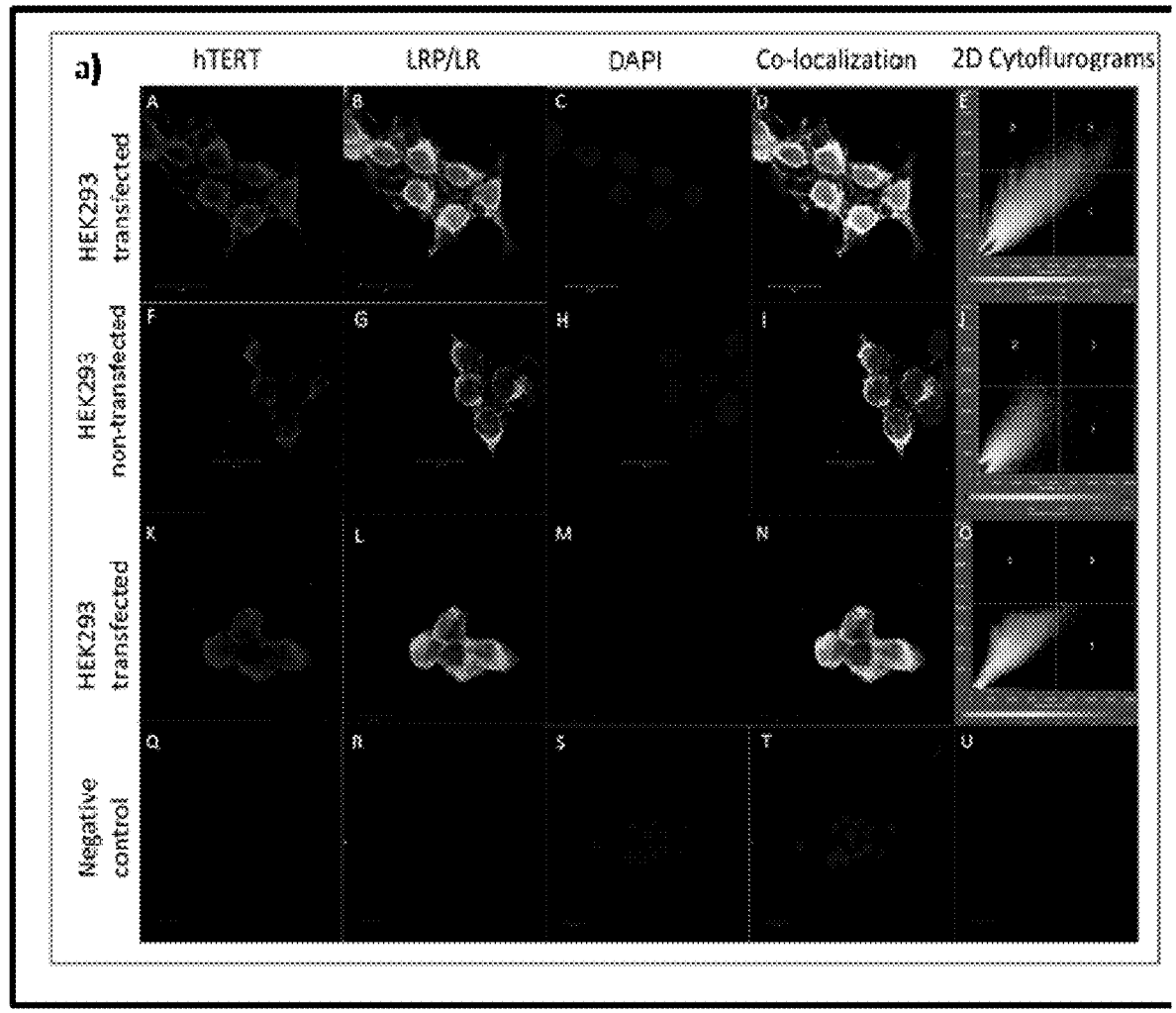
FIG. 2A shows immunofluorescence confirming co-localization of hTERT, LRP/LR and LRP::FLAG in HEK293 cells.
Figure 2B:
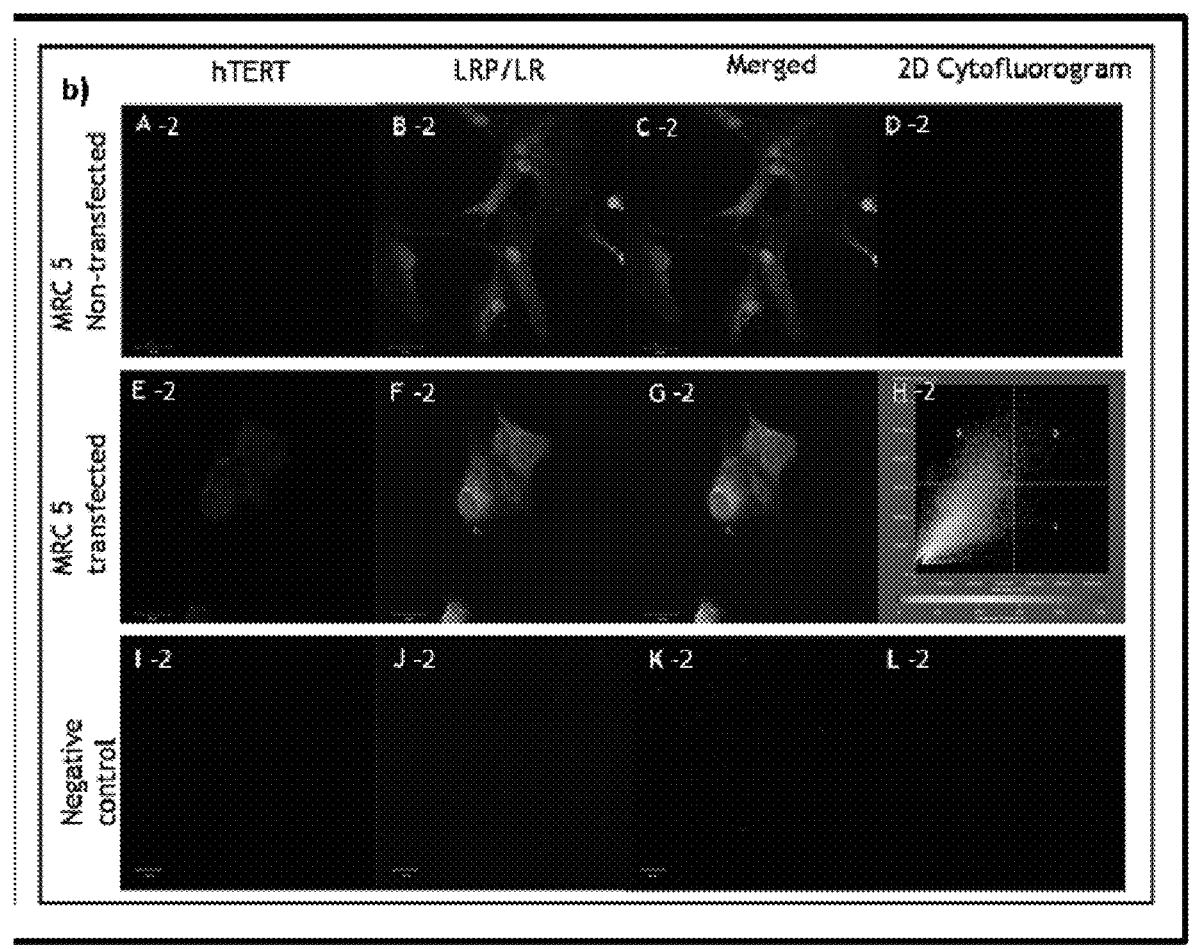
FIG. 2B shows immunofluorescence confirming co-localization of hTERT, LRP/LR and LRP::FLAG in MRC 5 cells.

LRP::FLAG was detected with anti-FLAG primary and LRP/LR was detected with anti-LRP/LR IgG1-iS18. Both primary antibodies were then targeted by an appropriate secondary antibody coupled with HRP. The loading control β-actin was detected with an anti-β-actin-peroxidase conjugate antibody. Analysis revealed that LRP::FLAG was found to only be expressed in HEK293 and MRC 5 transfected cell samples, with no LRP::FLAG detection in the non-transfected cell samples.

hTERT Co-Localises with LRP/LR and LRP::FLAG and in Fact Share an Interaction:

Immunofluorescence and confocal microscopy were employed to confirm the co-localization shared between hTERT and LRP/LR intracellularly. FIG. 2A shows immunofluorescence confirming co-localization of hTERT, LRP/LR and LRP::FLAG in HEK293 cells, and FIG. 2B shows immunofluorescence confirming co-localization of hTERT, LRP/LR and LRP::FLAG in MRC 5 cells.

FIGS. 2A and B show LRP co-localizes with hTERT in HEK293 cells and MRC 5 cells overexpressing LRP:: FLAG, respectively. Localization and co-localization patterns intracellularly of hTERT to LRP/LR and LRP::FLAG in transfected as well as non-transfected HEK293 cells is shown. hTERT was detected with an anti-hTERT and secondary coupled APC antibodies (see panels A, F, K, A-2, E-2). LRP/LR was detected with anti-LRP/LR IgG1-iS18 and secondary FITC coupled antibodies (se panels B, G, B-2, F-2). LRP::FLAG was detected with anti-FLAG and FITC coupled secondary antibodies (see panel L); Dapi nuclear staining (see panels C, H, S).

Merger between LRP/LR and LRP::FLAG (see panels D, I, C-2, G-2) and LRP::FLAG and hTERT (see panel N) illustrates co-localization caused by the spatial overlap between the proteins. 2D Cytoflurograms confirmed that the overlap observed was co-localization between the proteins (see panels E, J, O, H-2). Secondary antibody controls confirmed that no auto-fluorescence or non-specific binding (Q-U, 1-2-L-2). Images were taken at 630× magnification. All scale bars are 20 μm.

The co-localization panels in FIG. 2A, represent a combination of the red (first column on the left hand side corresponding to panels A, F, K, and Q) (hTERT) and green (second column from left hand side corresponding to panels B, G, L and R) (LRP/LR and LRP::FLAG), where areas of yellow (see panels D, I and N) fluorescence indicated an overlap and possible interaction of the two proteins. The intracellular co-localization of LRP/LR and hTERT was pronounced for both non-transfected and transfected HEK293 cells. Additionally, it was found that LRP::FLAG and hTERT co-localized in HEK293 transfected cells (panels K-N). The co-localization images and 2D-Cytoflurograms (Panels E and J) further highlighted that a greater degree of co-localization occurred in cells overexpressing LRP::FLAG. Additionally, this co-localization was further assessed by Z-stack imaging (FIG. 7), which involved taking a series of images at different depths within the cell. These images confirmed that co-localization was present throughout the cell. However, majority of the co-localization between hTERT and LRP/LR was detected in the centre of the cell within the perinuclear compartments.

Figure 3:
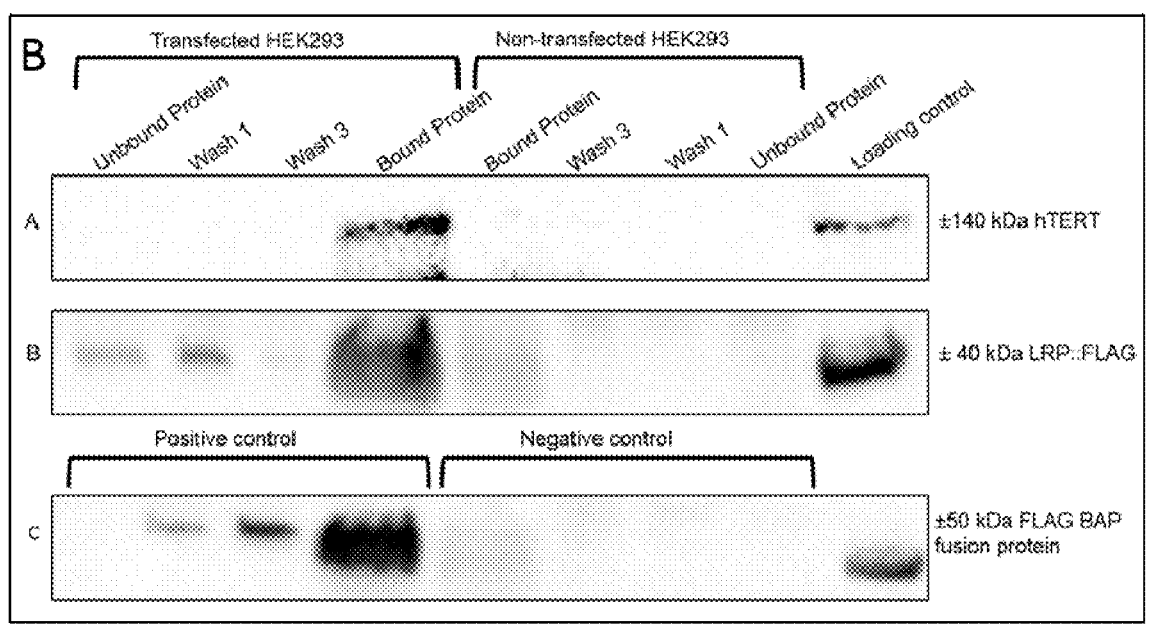
FIG. 3 shows LRP::LR and hTERT interaction confirmed by FLAG® co-immunoprecipitation in HEK293 cells.

The co-localization between hTERT and LRP/LR of HEK293 cell lines was further assessed by FLAG® Co-Immunoprecipitation (FIG. 3). This was to confirm if the co-localization observed, was an interaction between the two proteins. The assay was run with the BAP fusion protein as a positive control, which was detected in the Bound protein fraction. Similarly, the presence of both LRP::FLAG and hTERT bound to the FLAG®M2 beads was detected, in the Bound Protein column (panel A and B) for transfected HEK293 cells. In contrast, non-transfected HEK293 protein lysates failed to bind to the FLAG®-M2 beads. This was due to the absence of the LRP::FLAG protein in these cells and were thus, not detected. Thus confirming an interaction between hTERT and LRP::FLAG/LRP/LR.

FIG. 3 shows LRP::LR and hTERT interaction confirmed by FLAG® Co-immunoprecipitation. Immunoprecipitation assays were used to detect LRP::FLAG as well as proteins it associated with, that were bound to anti-M2 flag beads. To ensure the validity of the western blots, crude HEK293 lysate was used as a loading control. For protein detection LRP::FLAG and BAP fusion protein were targeted with an anti-FLAG primary antibody. In addition, hTERT was detected anti-hTERT primary antibody. All primary antibodies were detected with an appropriate secondary coupled with the HRP enzyme. The BAP fusion protein (50 kDa) used as a positive control and corresponding negative control in Panel C verified the efficacy of the procedure. Detection of LRP::FLAG at ±40 kDa (Panel B) and hTERT at ±140 kDa (Panel A) in the Bound protein fraction for HEK293 transfected cells indicated an immunoprecipitation of the two. This in turn illustrated an interaction shared between LRP/LR and hTERT. However, non-transfected HEK293 cells detected no signal for either protein due to the absence of LRP::FLAG.

Figures 4A, 4B:
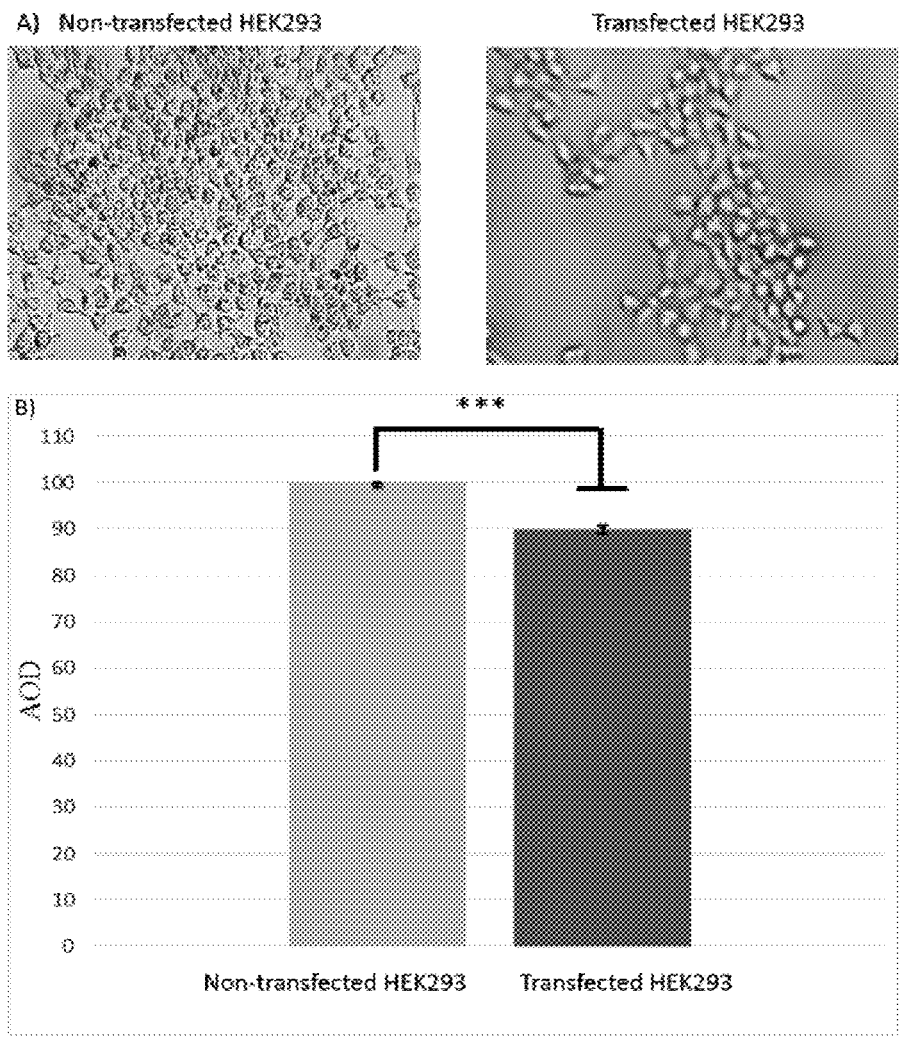
FIG. 4A shows LRP::FLAG overexpression induces a significant reduction in β-galactosidase activity in HEK293 transfected cells.
FIG. 4B shows a graph confirming that LRP::FLAG overexpression induces a significant reduction in β-galactosidase activity in HEK293 transfected cells.

LRP::FLAG overexpression significantly decreases β-galactosidase levels and H2AX foci:

The senescent marker β-galactosidase was analysed in HEK293 cells transfected with the pCIneo-LRP::FLAG and non-transfected cells, to assess the effect of LRP::FLAG overexpression on ageing markers. Two separate assays were incorporated to assess β-galactosidase activity, which displayed similar results. The first assay indicated that the non-transfected HEK293 cells contained a larger quantity of senescent (blue) cells compared to the transfected HEK23 cells (FIG. 4A). This data was further confirmed by the reporter lysis β-galactosidase assay, which measured quantitatively the enzyme activity of β-galactosidase. It was found that HEK293 cells overexpressing the LRP::FLAG had a significant 10% reduction in β-galactosidase activity, when compared to the non-transfected cell line (FIG. 4B).

FIGS. 4A and 4B show LRP::FLAG overexpression induces a significant reduction in β-galactosidase activity in HEK293 transfected cells. Panel A indicates qualitatively the number of cells expressing SA-β-galactosidase in transfected and non-transfected HEK293 cells. Cells stained blue are indicative of aged or senescent cells. Panel B indicates the amount of β-galactosidase activity in cells qualitatively. Transfected cells were found to have 10% less activity compared to non-transfected cells. Data was found to be significant where ***$p<0.001$.

FIG. 4 shows that LRP::FLAG overexpression significantly decreases the levels of tested senescent markers: β-galactosidase and H2AX foci.

FIGS. 4 A and B show percentage change in enzymatic activity of β-galactosidase following LRP::FLAG overexpression in HEK293 cell lines when compared to the non-transfected lines. A 10% reduction in enzymatic activity is observed in transfected HEK293 cell lines (n=3; P=4.22E-05).

Figure 4C:
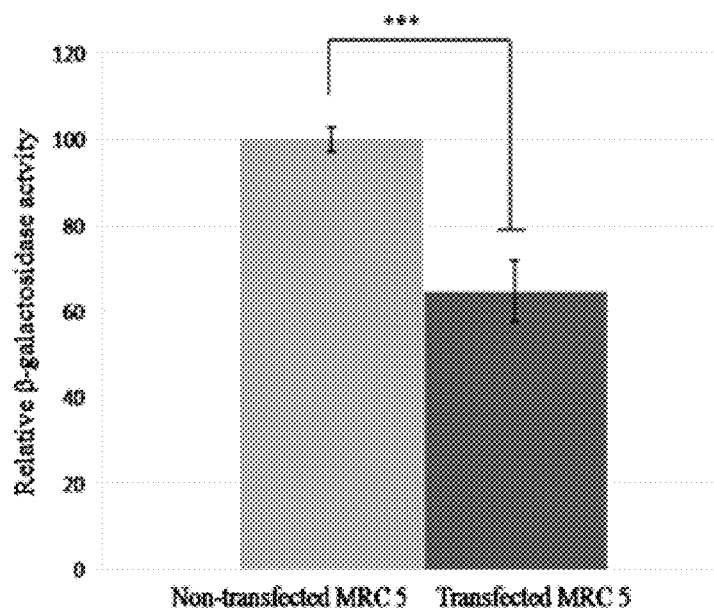
FIG. 4C shows a graph confirming that LRP::FLAG overexpression induces a significant reduction in β-galactosidase activity in MRC 5 transfected cells.
Figures 4D, 4E:
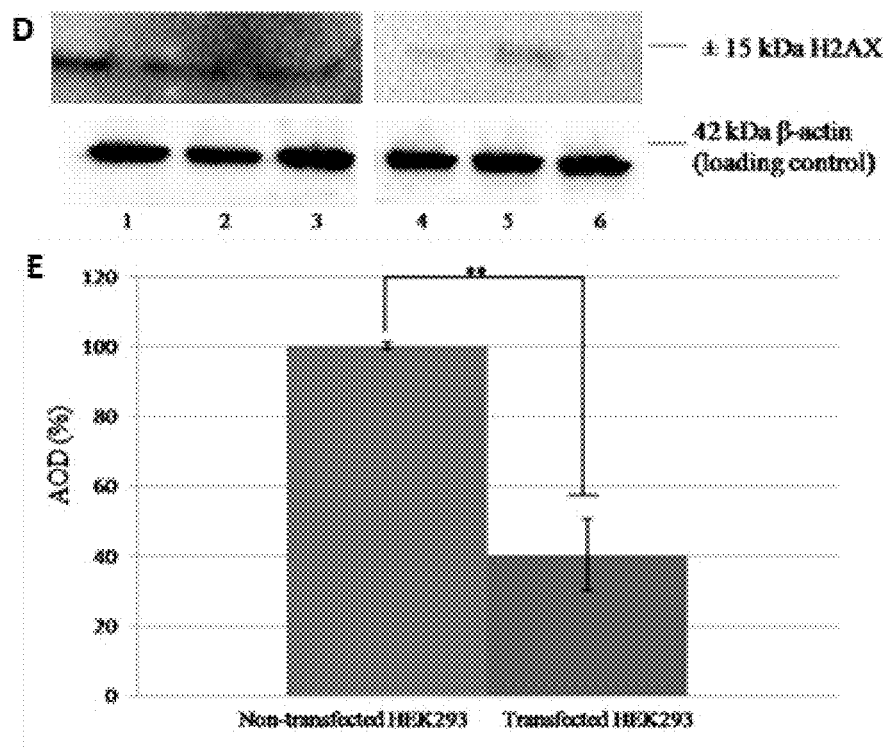
FIG. 4D shows LRP::FLAG overexpression induces a significant reduction in H2AX levels in HEK293 transfected cells.
FIG. 4E shows a graph confirming that LRP::FLAG overexpression induces a significant reduction of 60.78% (n=3; p=0.0017) in H2AX levels in HEK293 transfected cells.
Figures 4F, 4G:
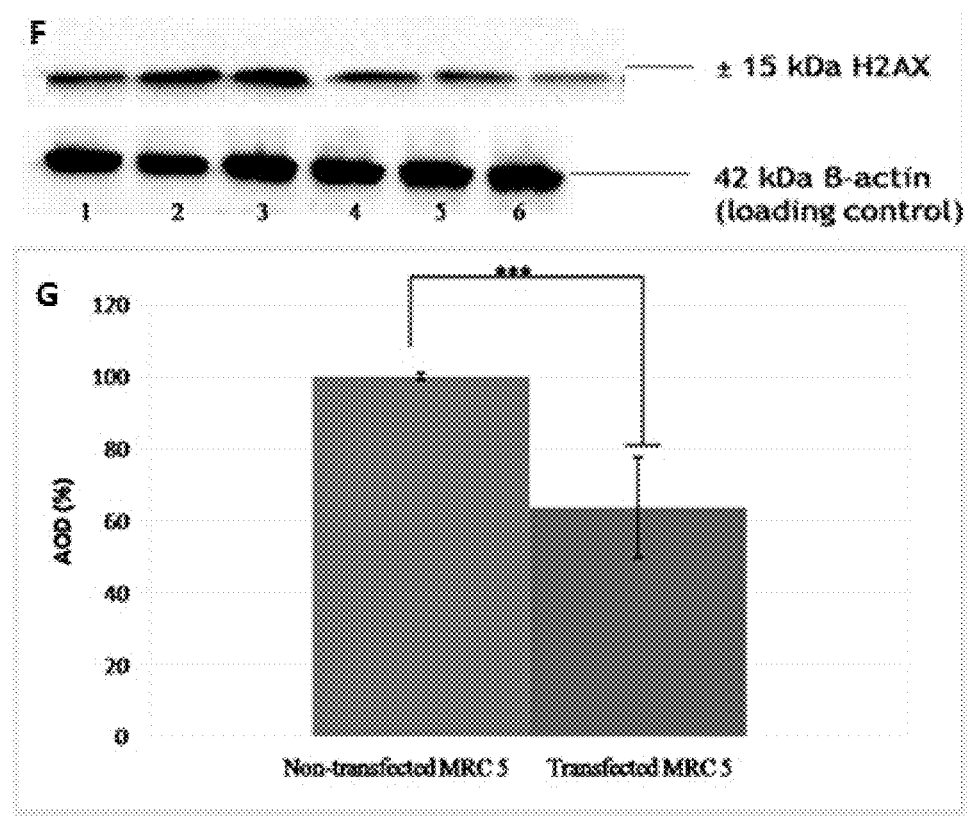
FIG. 4F shows LRP::FLAG overexpression induces a significant reduction in H2AX levels in MRC 5 transfected cells.
FIG. 4G shows a graph confirming that LRP::FLAG overexpression induces a significant reduction of 40% (n=3; p=0.009) in H2AX levels in MRC 5 transfected cells.

FIG. 4C shows percentage change in enzymatic activity of β-galactosidase following LRP::FLAG overexpression in MRC 5 cell lines when compared to the non-transfected lines A 40% reduction in enzymatic activity is observed in transfected MRC 5 cell lines (n=3; P=0.0008).

FIGS. 4D and 4E, and FIGS. 4F and 4G, show densitometric analysis of H2AX levels expressed as a percentage change with non-transfected (lanes 1-3) compared to transfected lines (lanes 4-6) for HEK293 cells and MRC 5 cells, respectively. Sample size n=3 biological repeats per cell line. Data as a mean±sd. *$p<0.05$, $p<0.01$, *$p<0.001$ by paired t-test.

H2AX foci are histones that are specifically phosphorylated at pSer139 that serve to mark sites of DNA damage and doubled stranded break which accumulate with increased cellular age due to the loss of telomeric ends (Pospelova et al 2009; Tomas-Loba et al 2008). Interestingly, densitometric analysis revealed a prominent decrease in the levels of H2AX in both cell lines (HEK293 and MRC 5) overexpressing LRP::FLAG. HEK 293 lines overexpressing LRP::FLAG exhibited a 60.78% (n=3; P=0.0017) reduction in H2AX levels, and MRC 5 lines overexpressing LRP::FLAG exhibited a 40% (n=3; p=0.009) reduction in H2AX levels.

Figures 5A, 5B:
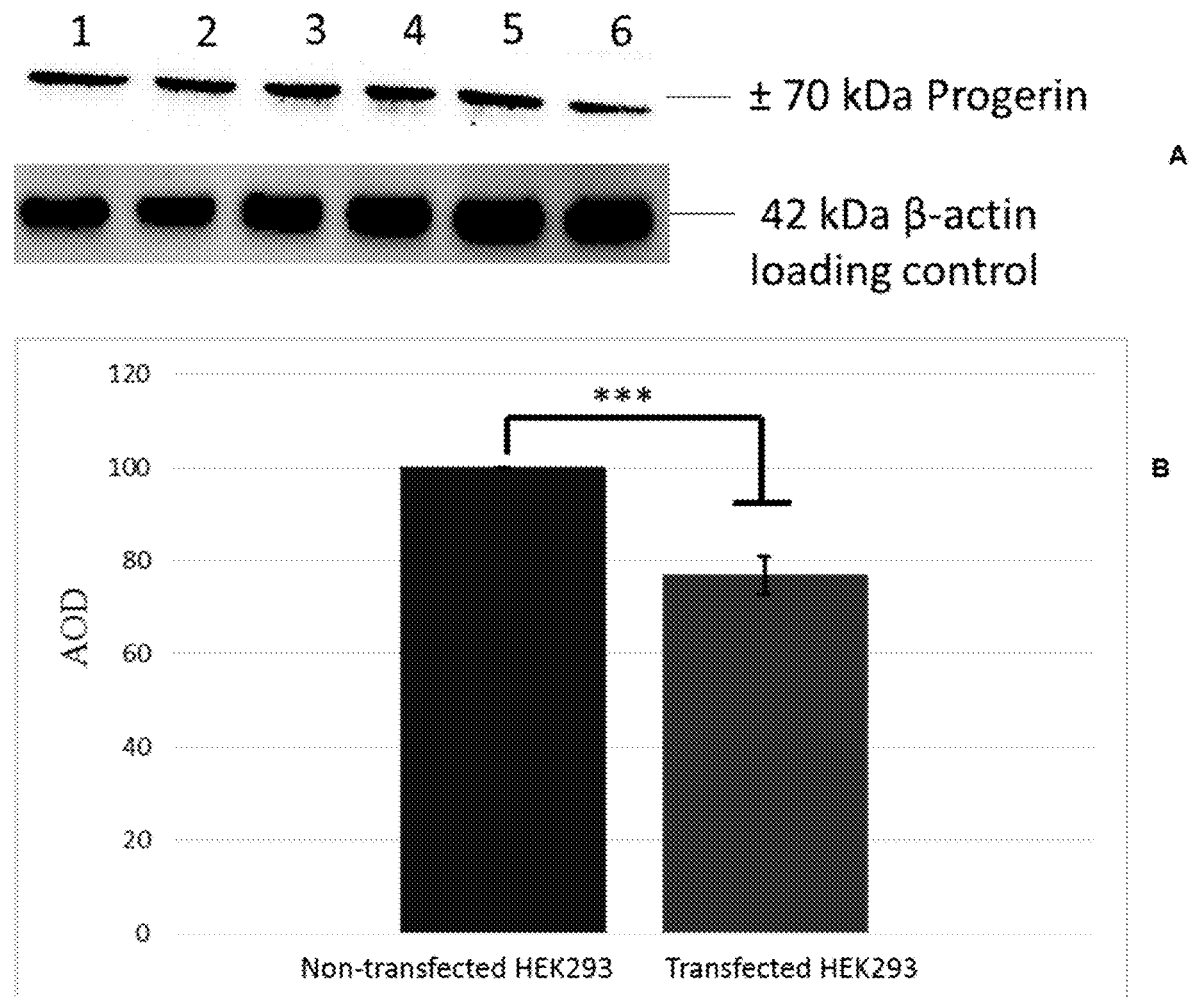
FIG. 5A shows reduction in progerin levels mediated by LRP::FLAG overexpression in transfected and non-transfected HEK293 cells.
FIG. 5B shows a graph confirming that there is a reduction in progerin levels mediated by LRP::FLAG overexpression in transfected and non-transfected HEK293 cells.

LRP::FLAG Overexpression Causes a Significant Reduction in the Total Levels of the Senescent Marker Progerin The expression of progerin or increase of it, is commonly associated with increased cellular ageing. Due to this reason, progerin was used as a senescent marker. Western blotting was utilised to assess the effects of LRP::FLAG overexpression on the protein levels of the senescent marker progerin and compared to the loading control β-actin (FIG. 5A). Total progerin levels were then quantified by densitometry (FIG. 5B). Analysis revealed that in HEK293 cells overexpressing LRP::FLAG, a significant reduction of 23% was observed in total progerin levels, when compared to non-transfected HEK293 cells (n=3; P=0.00085).

FIGS. 5A and 5B show reduction in progerin levels mediated by LRP::FLAG overexpression in transfected and non-transfected HEK293 cells. The expression levels of progerin were assessed following transfection. Progerin was detected with an anti-progerin primary antibody and, appropriate secondary antibody coupled to HRP. The expression levels of progerin were determined for non-transfected (lane 1-3) and transfected HEK293 (lane 4-6) cells. Densitometric analysis performed on the western blots revealed a significant (***$p<0.001$) reduction of 23.56% in progerin levels within HEK293 transfected cells. This was in respect to the non-transfected HEK293 cells set to 100%.

LRP::FLAG Overexpression Significantly Increases hTERT Expression and Telomerase Activity, Resulting in a Subsequent Increase in Telomere Length:

One of the key factors regulating cellular senescence (cellular ageing) is telomere attrition due to insufficient maintenance by telomerase. Interestingly, significant levels of hTERT have been detected with no corresponding increase in telomere length (Liu and Yung, 1998; Wick et al., 1999).

Western blotting was conducted (see FIG. 8) to determine if an overexpression of LRP::FLAG would subsequently affect levels of hTERT and whether or not increased levels of hTERT would have any effect on telomerase activity and/or telomerase length. Western Blots quantified by densitometric analysis revealed a significant difference between transfected and non-transfected HEK293 cells and MRC 5 cells. HEK293 cells and MRC 5 cells overexpressing LRP::FLAG had close to a twofold (176.4%) increase and a 339.26% increase in hTERT expression, respectively.

FIG. 8 shows LRP::FLAG overexpression significantly elevates hTERT levels and telomerase activity for a striking telomere elongation in both HEK293 and MRC 5 cells.

Figures 8A, 8B:
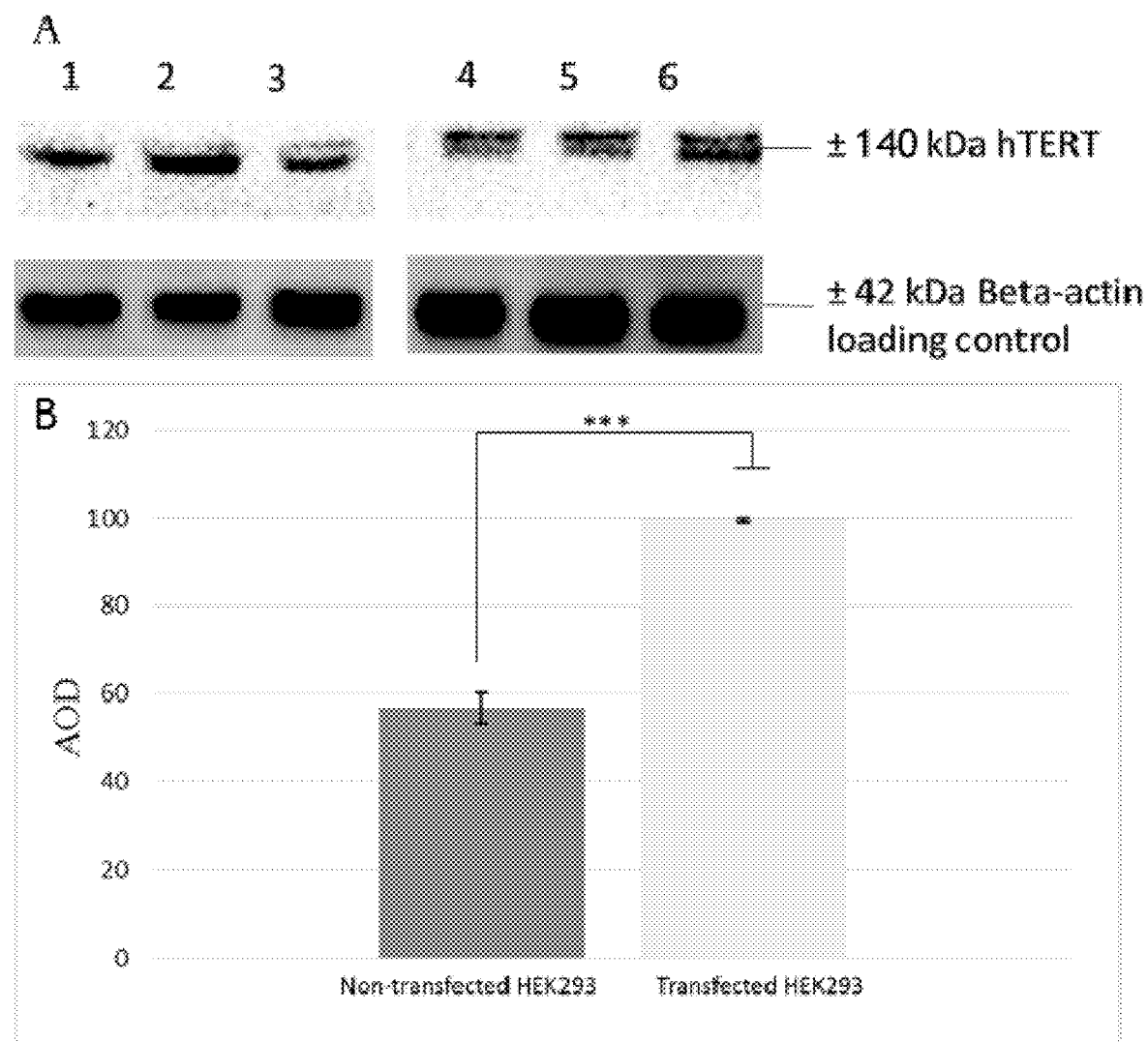
FIG. 8A shows LRP::FLAG overexpression induces overexpression of hTERT levels in HEK293 transfected cells.
FIG. 8B shows a graph of the Western blotting confirming LRP::FLAG overexpression elevates hTERT levels in HEK293 transfected cells.
Figures 8C, 8D:
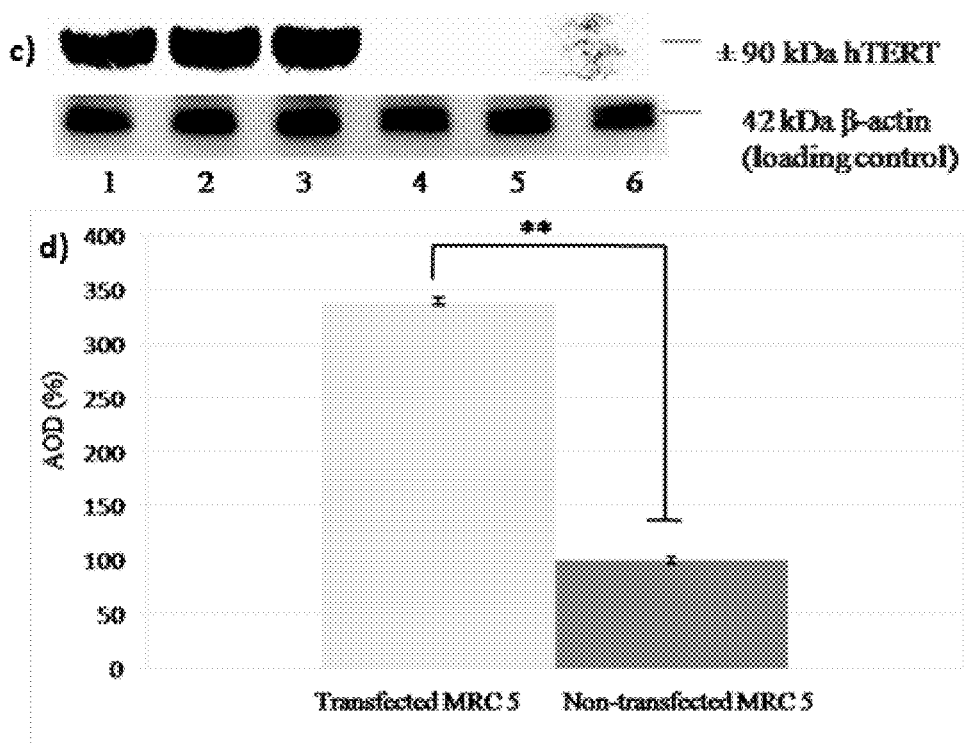
FIG. 8C shows LRP::FLAG overexpression induces overexpression of hTERT levels in MRC 5 transfected cells.
FIG. 8D shows a graph of the Western blotting confirming LRP::FLAG overexpression elevates hTERT levels in MRC 5 transfected cells.

FIGS. 8A and 8B show Western blot of hTERT with transfected (lane 1-3) and non-transfected (lane 4-6) for HEK293. FIGS. 8C and 8D show Western blot of hTERT with transfected (lane 1-3) and non-transfected (lane 4-6) for MRC 5.

Densitometric analysis expressed as a relative percentage in change respective to the non-transfected samples.

Figure 8E:
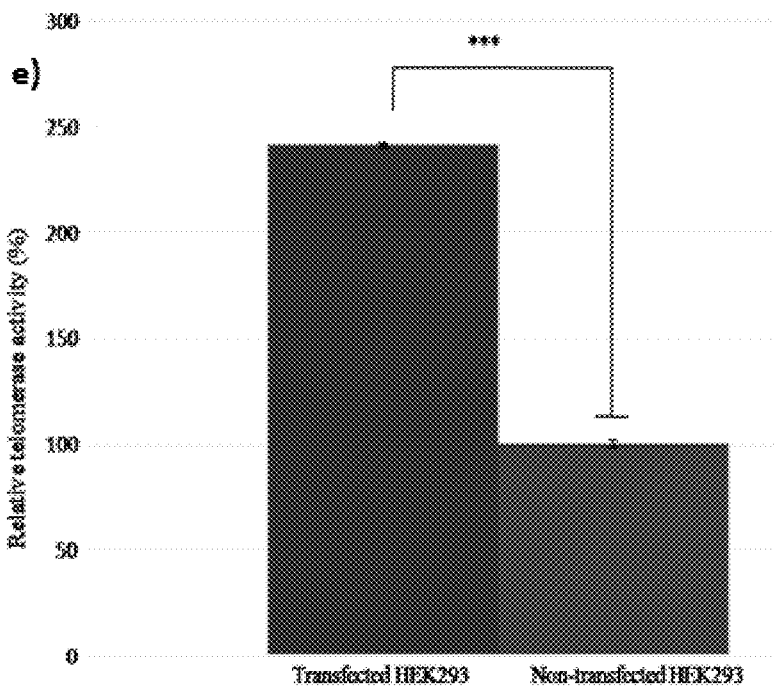
FIG. 8E shows relative telomerase activity in transfected and non-transfected HEK293 cells as a percentage in activity when compared to the non-transfected cell lines.

FIG. 8E shows relative telomerase activity in transfected and non-transfected HEK293 cells as a percentage increase in activity when compared to the non-transfected cell line.

Figure 8F:
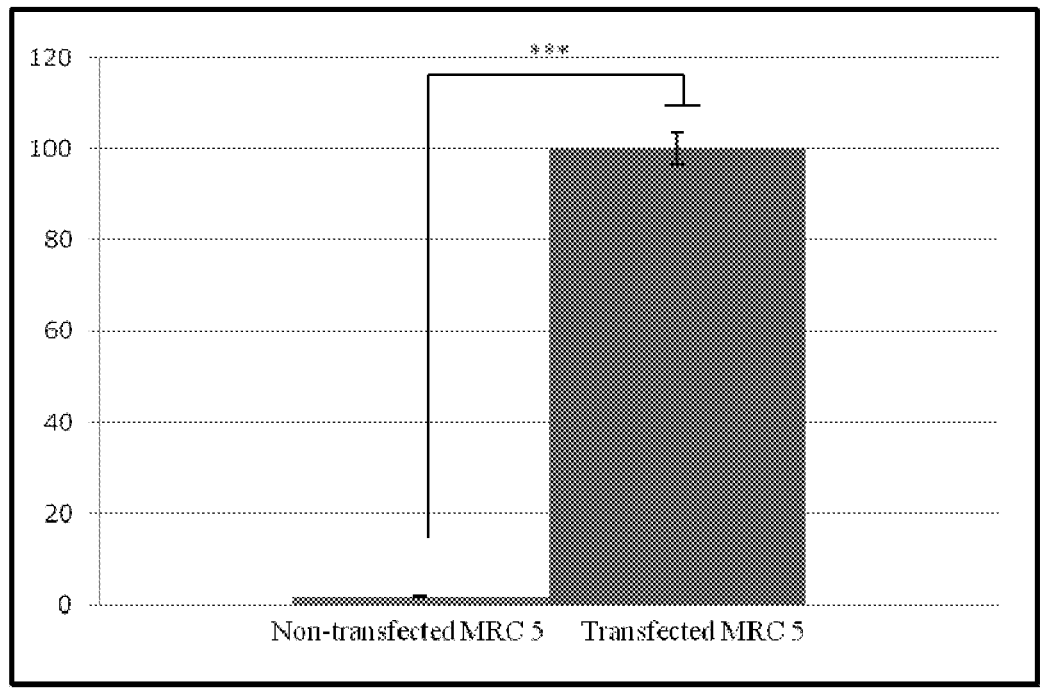
FIG. 8F shows relative telomerase activity in transfected and non-transfected MRC 5 cells as a percentage in activity when compared to the non-transfected cell lines.

FIG. 8F shows relative telomerase activity and real time PCR in transfected and non-transfected MRC 5 cells. Analysis involved comparing the transfected to non-transfected cells, as the normal illustrated little to no activity. The relative activity of telomerase revealed a significant 98% elevation in activity in transfected MRC 5 cells, when compared to the non-transfected MRC cell line.

Figure 8G:
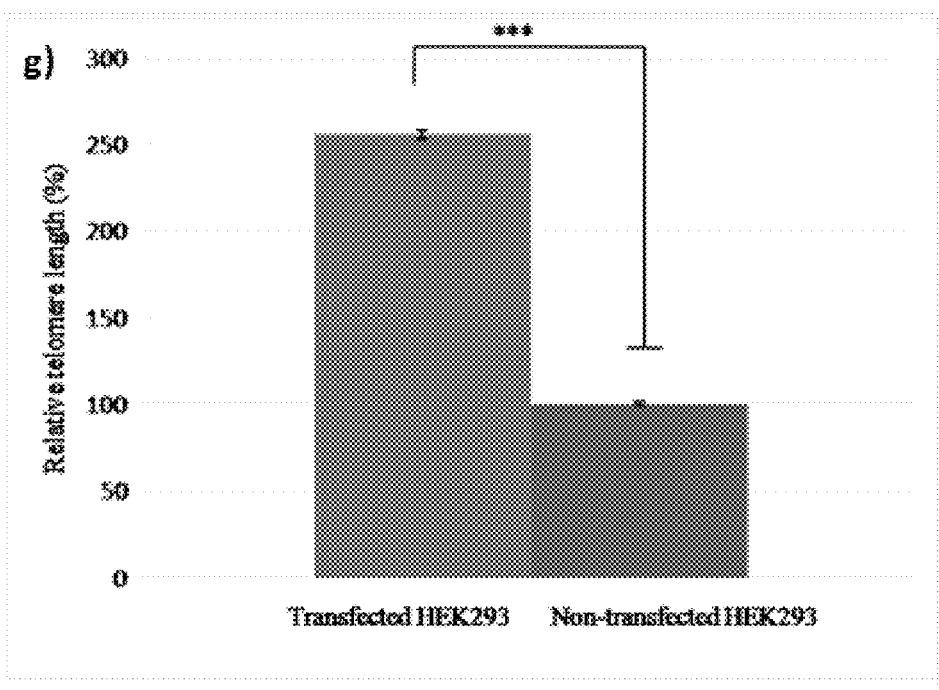
FIG. 8G shows relative telomere length in transfected HEK293 cell lines as a percentage change in overall telomere length when compared to the non-transfected cell lines.
Figure 8H:
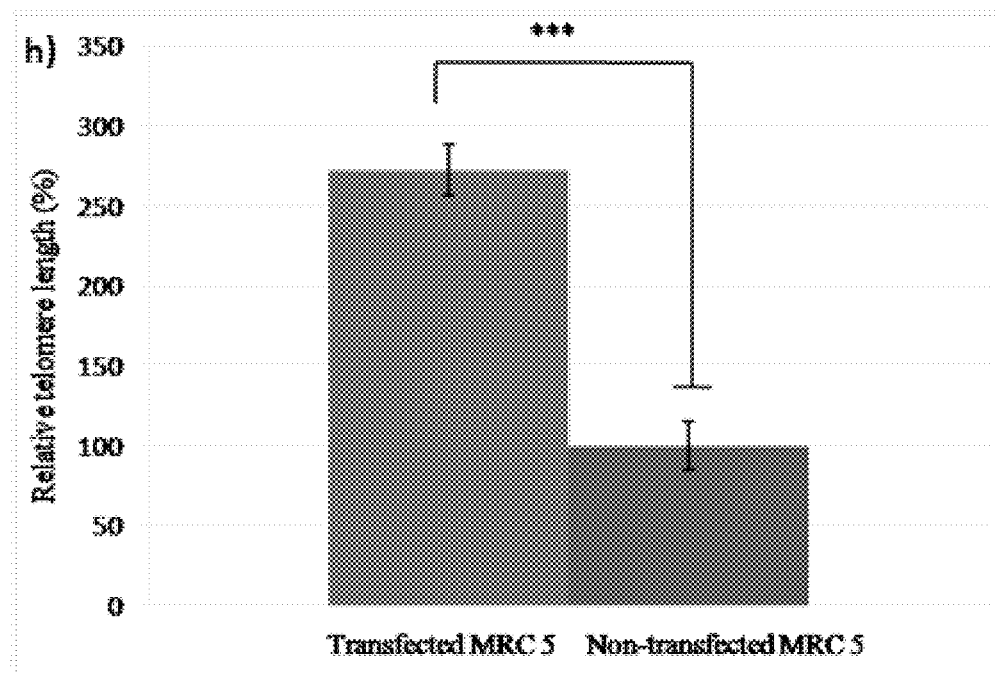
FIG. 8H shows relative telomere length in transfected MRC 5 cell lines as a percentage change in overall telomere length when compared to the non-transfected cell lines.

FIGS. 8G and 8H show relative telomere length in transfected HEK293 and MRC 5 lines as a percentage change in overall telomere length versus the non-transfected HEK293 and MRC 5 cells, respectively. Sample size n=3 biological repeats per cell line. Data as a mean±sd. *$p<0.05$, $p<0.01$, *$p<0.001$ by paired t-test.

LRP102-295::FLAG fragment overexpression induces a significant increase in telomerase activity for MRC 5 transfected cells. This is evidenced in FIG. 8I. Relative telomerase activity was assessed using the TRAPEZE telomerase kit (Merk Millipore) and real time PCR. Analysis involved comparing the transfected to non-transfected cells, as the normal illustrated little to no activity. The relative activity of telomerase revealed a significant 83.4% elevation in activity in MRC 5 cells transfected with the LRP102-295::FLAG fragment, when compared to the non-transfected MRC cell line.

Figure 6:
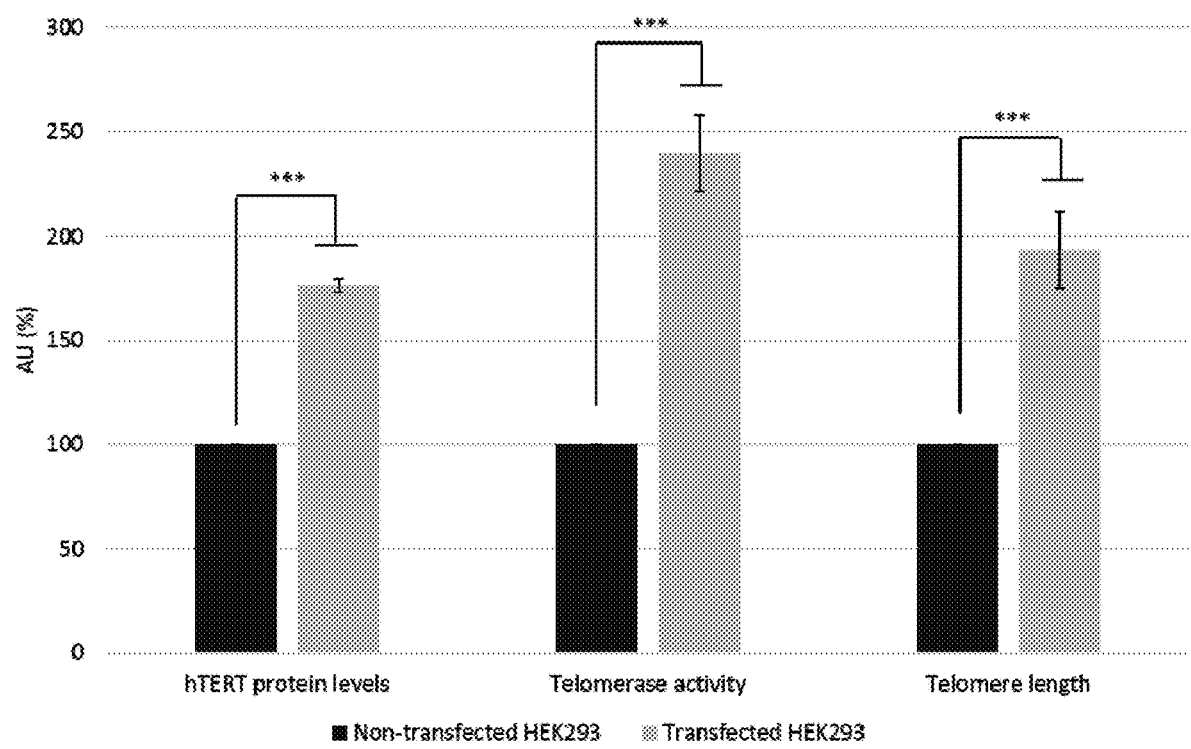
FIG. 6 shows LRP::FLAG overexpression significantly increases hTERT expression and telomerase activity to induce a significant elongation of the telomeres in transfected HEK293 cells.

To assess, whether the elevated levels of hTERT accompanying LRP::FLAG overexpression, subsequently affected telomerase activity real time PCR was performed. The levels of telomerase activity were found to be significantly different in HEK293 transfected cells (FIG. 6). Consequently, LRP::FLAG overexpression induced a twofold (239.74%) increase in telomerase activity, with respect to the non-transfected HEK293 cells.

In order to determine if the increased telomerase activity in transfected HEK293 cells provided an elongation and maintenance effect to the telomere ends, qPCR was performed. Prior to telomere length assessment DNA was extracted, and gradient PCRs were performed for the hTERT minisatellite and GAPDH (reference gene). It was found, that the DNA was amplifiable (see FIG. 9). Following gradient amplification, qPCR of the reference gene 36B4 was performed (see FIG. 10). Analysis revealed no significant difference between transfected and non-transfected HEK293 samples. Thereafter, qPCR was performed to determine relative telomere length. Upon normalising the telomere length data to the reference gene, a significant difference was illustrated in telomere length for HEK293 cells overexpressing LRP::FLAG (FIG. 6). Where, transfected HEK293 cells had more or less a two fold increase (193.56%) in overall telomere length, when compared to the non-transfected HEK293 cells (set at 100%).

FIG. 6 shows LRP::FLAG overexpression significantly increases hTERT expression and telomerase activity to induce a significant elongation of the telomeres in transfected HEK293 cells. The graph of FIG. 6 illustrates changes in telomere/telomerase factors induced by LRP::FLAG overexpression. Densitometric analysis of the hTERT western blots that transfected HEK293 cells produced 193.56% more hTERT, compared to non-transfected HEK293 cells (set at 100%). Relative telomerase activity was assessed using the TRAPEZE telomerase kit (Merk Millipore) and real time PCR. Thereafter, telomere length was assessed by qPCR and normalised to the reference gene 36B4. Analysis revealed a significant increase of 193.56% in relative telomere in transfected HEK293 cells when compared to non-transfected HEK293 cells All data was found to be significant where ***$p<0.001$.

Additional Information Regarding Example 1

Figure 7:
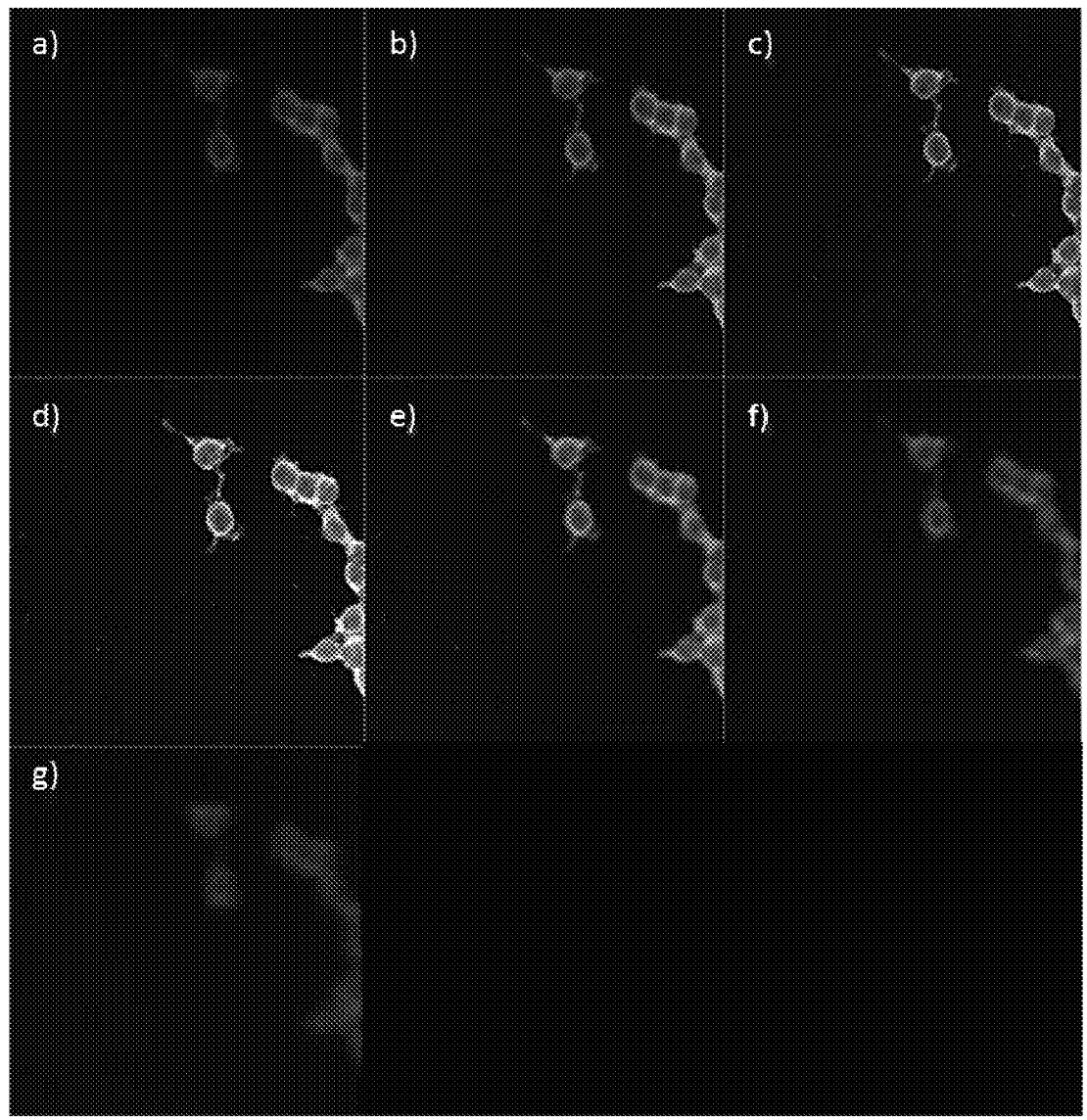
FIG. 7 shows Z-stack imaging confirming that co-localization between LRP/LR and hTERT occurs predominantly within the perinuclear compartments of HEK293 cells. The images taken at different depths within the cell, highlight that co-localization of the two proteins is present on the cell surface (a, b, f, g). Additionally, the co-localization present increases as images were taken further intracellularly (c, d, e). Furthermore, the greatest intensity of yellow florescence occurred within the median image (d) depicting the perinuclear compartments of the cells.

FIG. 7 shows Z-stack imaging confirming that co-localization between LRP/LR and hTERT occurs predominantly within the perinuclear compartments of HEK293 cells. Determination of the co-localization patterns for hTERT and LRP/LR throughout the HEK293. The images taken at different depths within the cell, highlight that co-localization of the two proteins is present on the cell surface (see panels a, b, f and g). Additionally, the co-localization present increases as images were taken further intracellularly (see panels c, d and e). Furthermore, the greatest intensity of yellow florescence occurred within the median image (d) depicting the perinuclear compartments of the cells.

FIG. 8A show Western blotting confirms LRP::FLAG overexpression elevates hTERT levels. Western blotting of hTERT where non-transfected HEK293 were run in lane 1-3 and transfected HEK293 samples were run in lane 4-6. Densitometric analysis illustrated that hTERT expression levels increased significantly by 1% in cells overexpressing LRP::FLAG.

Figure 9:
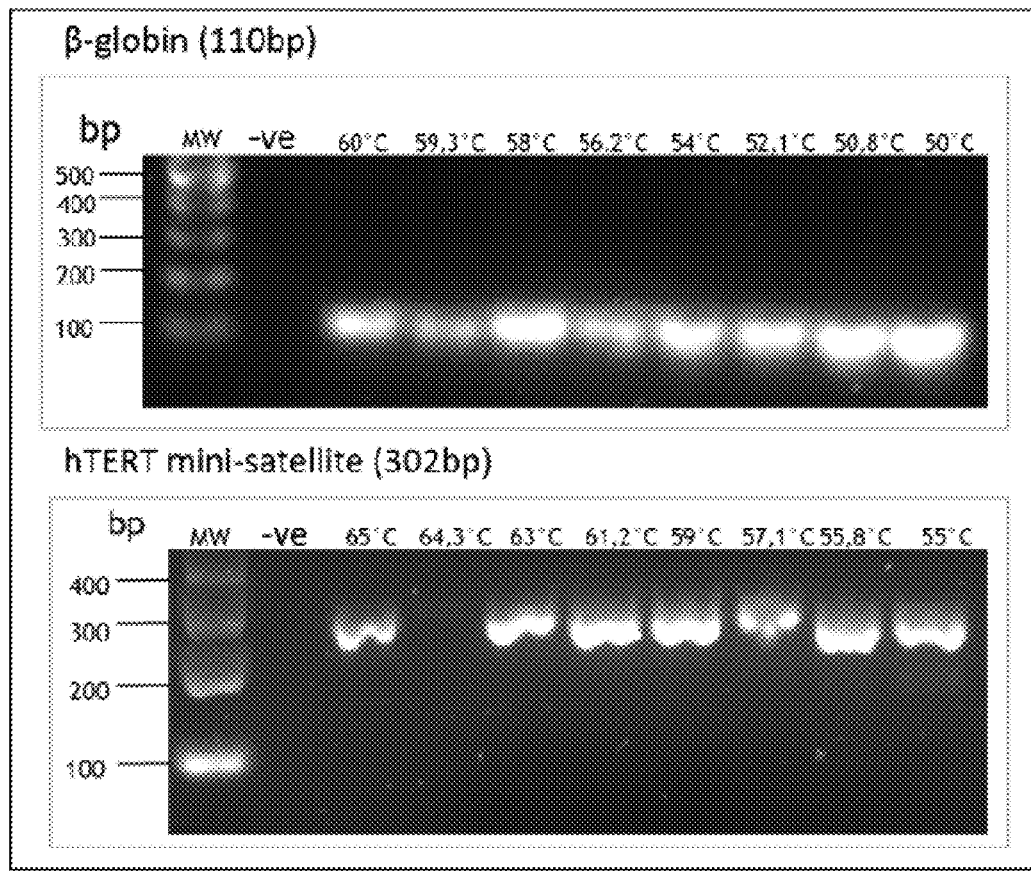
FIG. 9 shows gradient PCR for β-globin and hTERT confirming that transfected and non-transfected HEK293 DNA samples were amplifiable.

FIG. 9 shows gradient PCR for β-globin and hTERT confirming that transfected and non-transfected HEK293 DNA samples were amplifiable. Agarose gels displaying the resolved gradient PCR products for β-globin and the hTERT mini-satellite (MNS16A). The detection of bands in both gels indicated a successful PCR amplification and confirming the DNA was amplifiable. Additionally, gradient PCR was performed to determine the optimal annealing temperature of the primers, where 58° C. and 55, 8° C. were chosen for β-globin and the hTERT mini-satellite, respectively.

Figure 10:
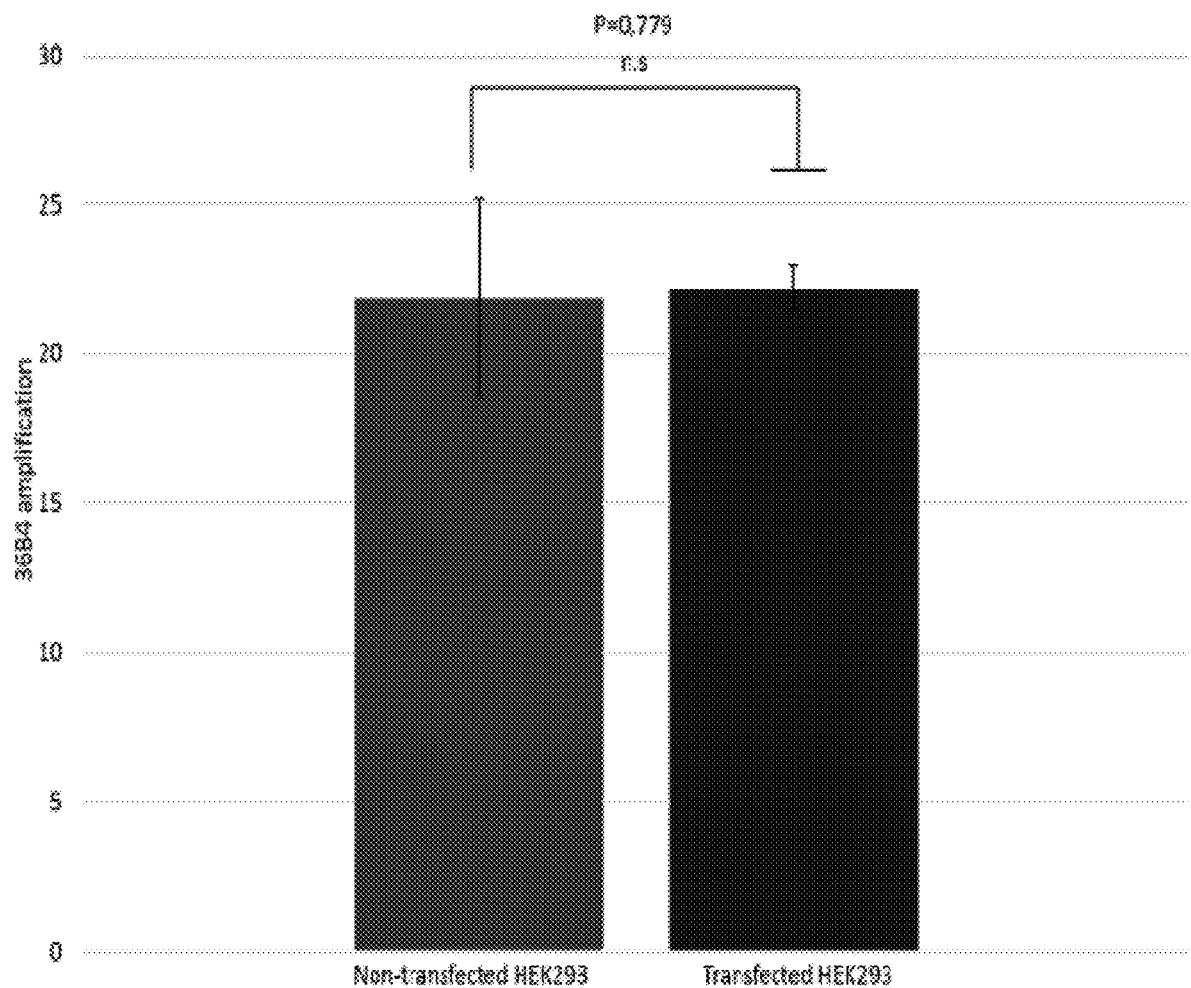
FIG. 10 shows qPCR amplification of the reference gene 36B4 confirming no difference transfected and non-transfected HEK293 amplification.
Figure 11A:
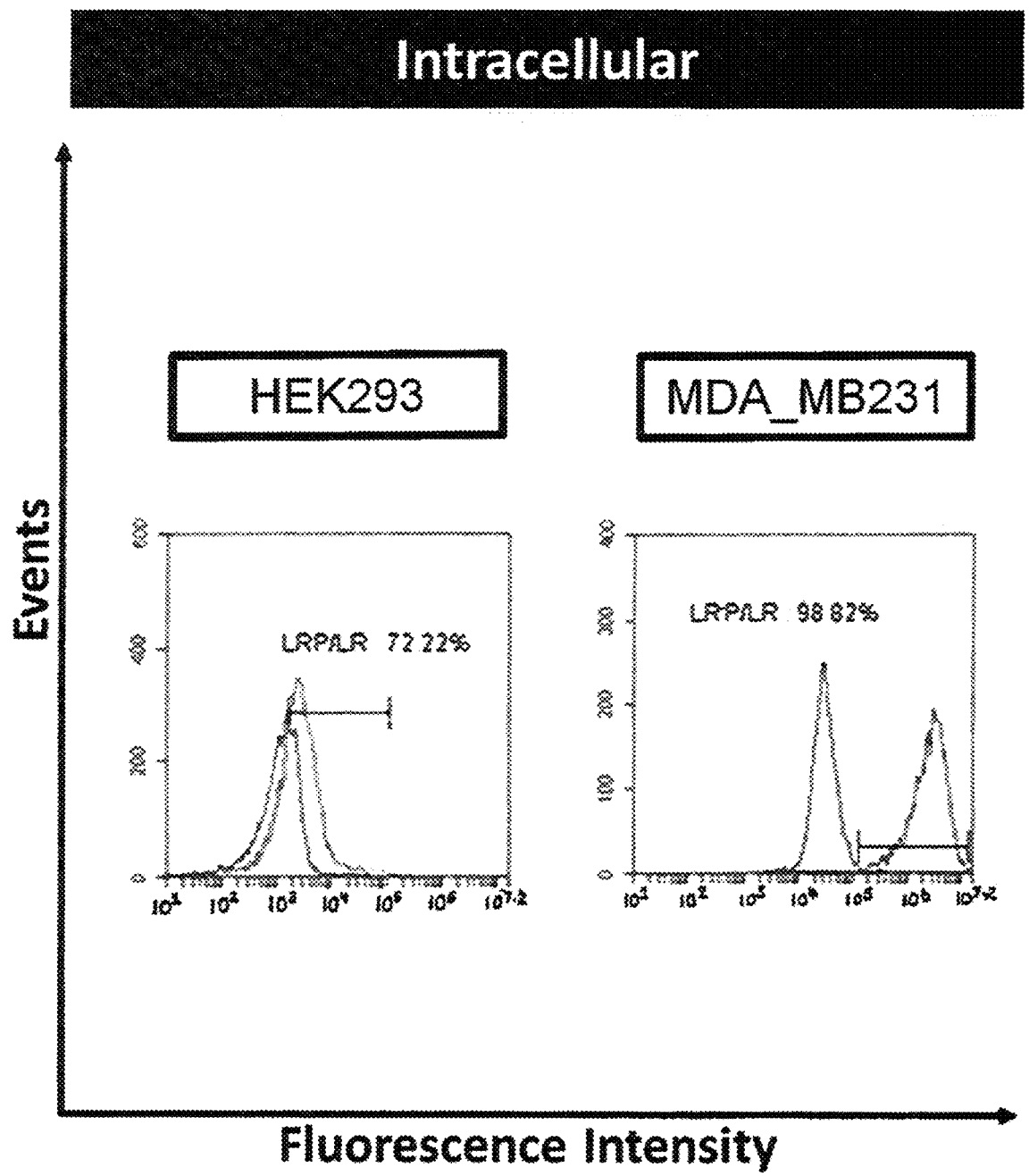
FIG. 11A shows flow cytometric detection of intracellular and cell surface levels of LRP/LR and hTERT on HEK293 and MDA_MB231 cells. Particularly 11A shows intracellular levels of LRP/LR in permeabilised HEK293 and MDA_MB231 cells were determined primarily by incubating the cells with IgG1-iS18 followed by incubation with anti-human-FITC coupled secondary antibodies (Sigma-Aldrich)
Figure 11B:
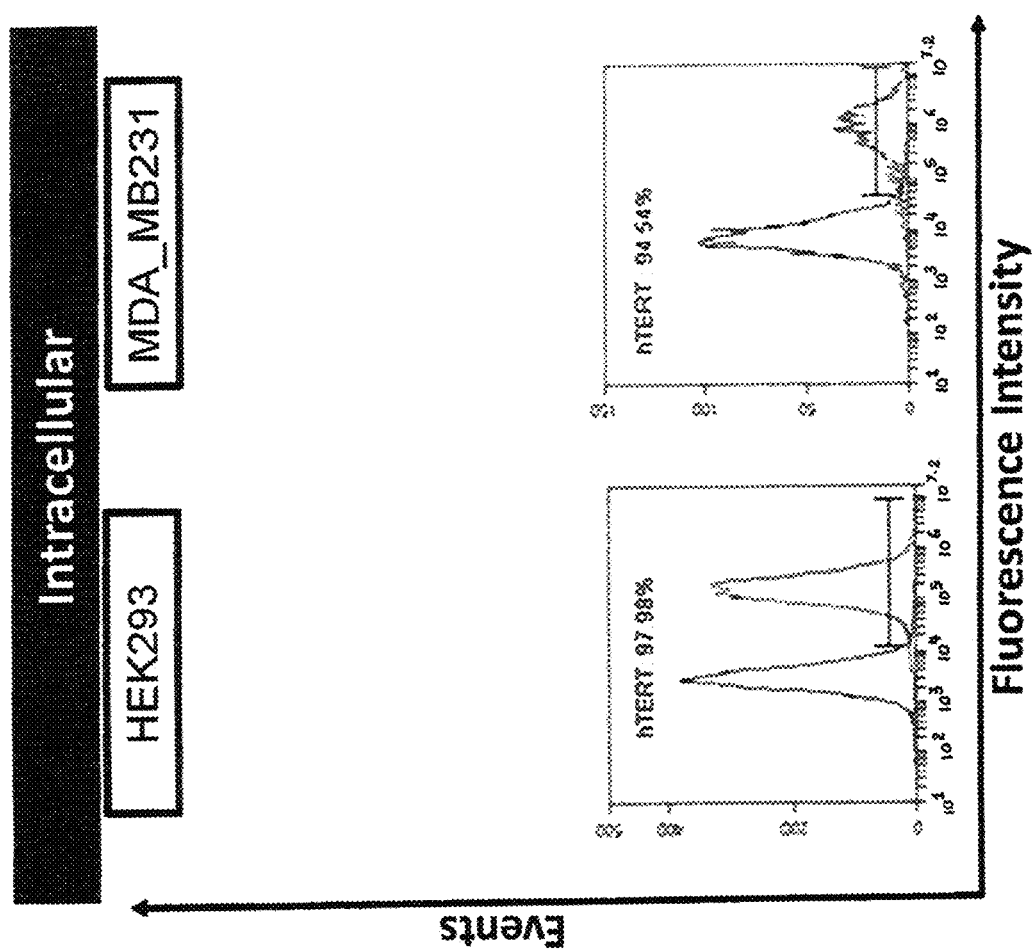
FIG. 11B shows flow cytometric detection of intracellular and cell surface levels of LRP/LR and hTERT on HEK293 and MDA_MB231 cells. Particularly 11B shows intracellular levels of hTERT in permeabilised HEK293 and MDA_MB231 cells were determined primarily by incubating the cells with anti-Telomerase reverse transcriptase antibody followed by incubation with goat anti-mouse IgG-APC coupled secondary antibodies (Sigma-Aldrich)
Figure 11C:
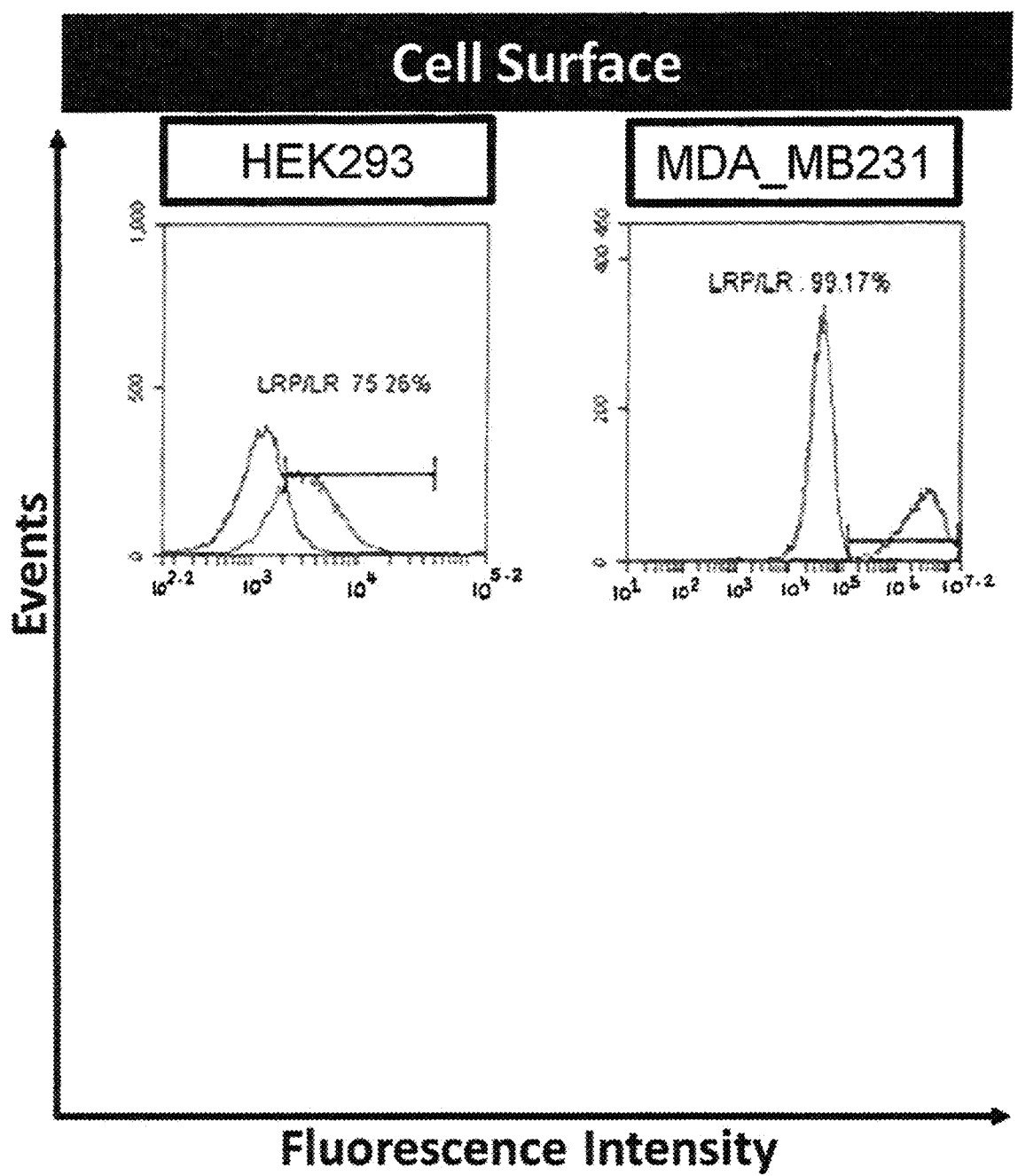
FIG. 11C shows flow cytometric detection of intracellular and cell surface levels of LRP/LR and hTERT on HEK293 and MDA_MB231 cells. Particularly, 11C shows cell surface levels of LRP/LR in non-permeabilised HEK293 and MDA_MB231 cells were determined primarily by incubating the cells with IgG1-iS18 followed by incubation with anti-human-FITC coupled secondary antibodies (Sigma-Aldrich)
Figure 11D:
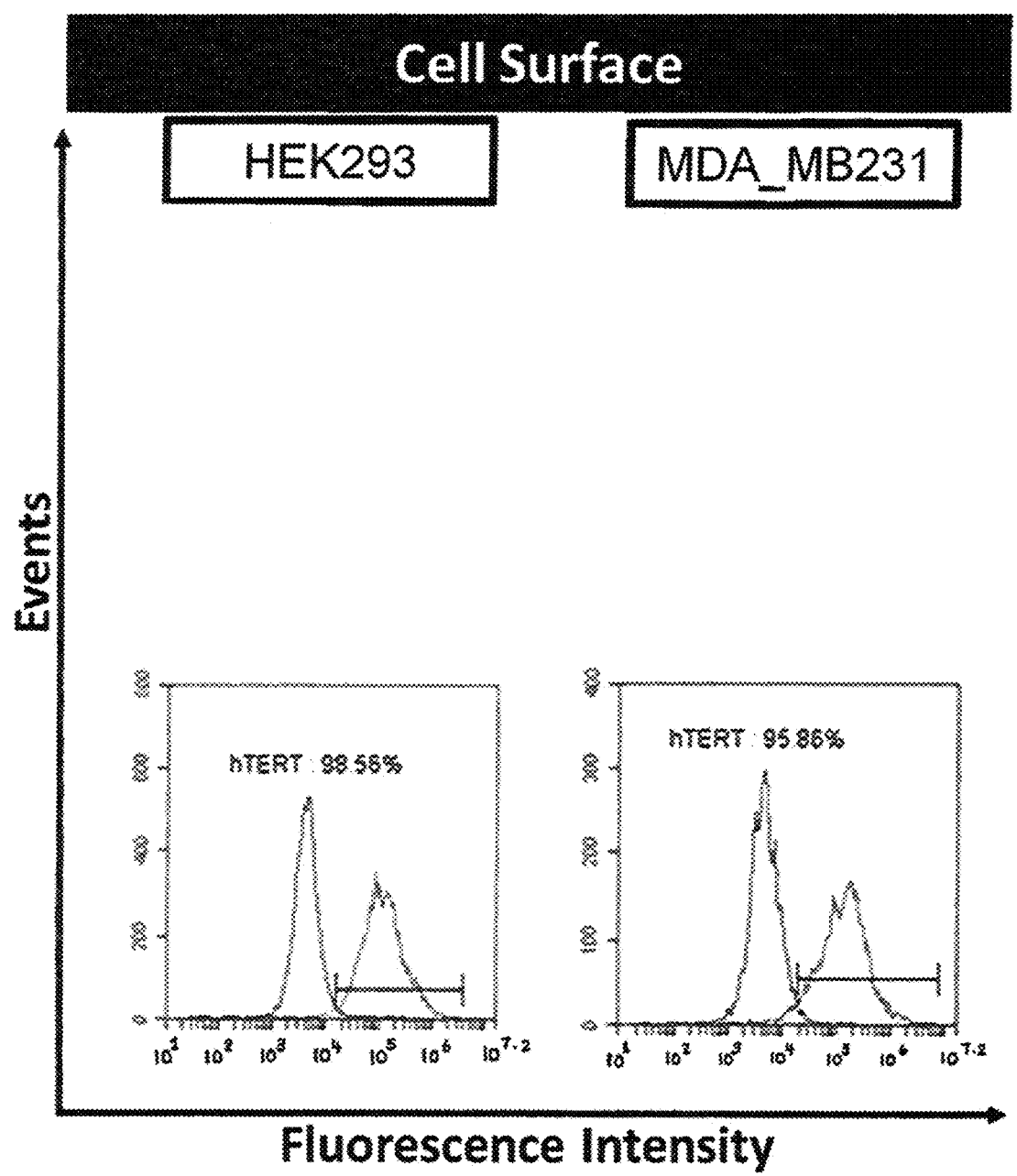
FIG. 11D shows flow cytometric detection of intracellular and cell surface levels of LRP/LR and hTERT on HEK293 and MDA_MB231 cells. Particularly, 11D shows cell surface levels of hTERT in non-permeabilised HEK293 and MDA_MB231 cells were determined primarily by incubating the cells with anti-telomerase reverse transcriptase antibody followed by incubation with Goat anti-mouse IgG-APC coupled secondary antibodies (Sigma-Aldrich)

FIG. 10 shows qPCR amplification of the reference gene 36B4 confirming no difference transfected and non-transfected HEK293 amplification. qPCR of the reference gene was performed to ensure that amplification levels between transfected and non-transfected HEK293 samples were equivalent. Data analysis confirmed that there was no significant difference between the samples (p=0.779).

The peptide/protein sequence of the LRP fragment 102-295 corresponds to the sequence listing as set forth in SEQ ID NO: 5.

Telomerase activity is a central component in impeding telomere dependent ageing, therefore the striking elevation observed in activity following overexpression of LRP::FLAG or its corresponding fragment (LRP 102-295::FLAG) confirms what was seen in HEK293 cells.

Interestingly, there was a strong elevation in telomerase activity even though the MRC 5 displayed negligible activity as seen in previous studies further confirming that LRP/LR and TERT or telomerase interact.

Additionally, these results compliment the high levels of TERT detected upon overexpression of LRP::FLAG and highlights that the extensive difference in telomere length is due to increased maintenance and telomere elongation. Indeed, these results collectively suggest that LRP/LR or fragment thereof is sufficient to increase telomerase dynamics and decrease senescent markers in cell lines with or without prior telomerase activity to impede the process of cellular senescence or cellular ageing.

Discussion (Example 1)

HEK293 and MRC 5 cells were induced to overexpress LRP::FLAG. This overexpression elevated total LRP/LR levels, which was confirmed through western blotting. The co-localization was confirmed in both non-transfected and transfected HEK293 and MRC 5 cell lines by confocal microscopy. In relation, Z-stack imaging confirmed that co-localization of the two proteins occurred predominantly in the perinuclear compartments of cells for HEK293 cell lines. In addition, it was illustrated that LRP::FLAG localized predominantly in the perinuclear compartments and nuclei of cells. Moreover, LRP::FLAG was confirmed to co-localize with hTERT and thereby showing shared an interaction. Interestingly, cells that were transfected with the pCIneo-LRP::FLAG also appeared to exhibit a greater degree of protein expression for hTERT, further suggesting an interaction between the two. This also resulted in a corresponding increase in co-localization indicated in the 2D-Cytofluorograms. In this way, elevated levels of LRP/LR were further confirmed.

The confirmed co-localization observed shows interaction between the two proteins. FLAG® Co-immunoprecipitation assays, confirmed this interaction. In this regard, the presence of both LRP::FLAG and hTERT bound to the beads strongly indicated a shared interaction between the two.

Following the confirmed interaction between LRP/LR and hTERT, the effect that LRP::FLAG overexpression exerted on cellular senescence (cellar ageing) was conducted. These effects were assessed by the senescent markers SA-β-galactosidase, H2AX foci and progerin. More specifically β-galactosidase, an enzyme produced in mammalian cells regardless of age, aids in cleaving of β-linked terminal galactosyl residues of substrates (Kurz et al., 2000).

In contrast, as cells age and reach senescence an increased production of β-galactosidase is observed, active at pH 6. Moreover, studies have shown that increased production of the enzyme is due to an increase in lysosomal mass, a common occurrence in senescent cells (Kurz et al., 2000). The results obtained in both assays indicated that overexpression of LRP::FLAG induced a physiological change in the cells. This change was sufficient to cause a significant reduction in β-galactosidase produced. Additionally, the reduction of this senescent marker suggested, that the cellular process of ageing was impeded in HEK293 cells and MRC 5 cells overexpressing LRP::FLAG. Moreover, these findings were further substantiated by the fact that two different experimental assays on different biological samples were conducted.

In order to verify the findings obtained from the β-galactosidase assays, total levels of the senescence marker progerin was assessed by western blotting. These results were in direct correlation with β-galactosidase, where a substantial decrease in total progerin levels was observed. In support, it was previously confirmed that progerin production is directly correlated to telomere erosion/dysfunction and increased cellular age (Cao et al., 2011). Therefore, decreases in its levels can be associated to an impediment in the ageing process. These findings, together with β-galactosidase strongly suggest that, overexpression of LRP::FLAG in non-tumorigenic cell lines, is sufficient to induce a physiological change. This change appears to allow the state and processing of young cells to be retained, by either slowing down or impeding the ageing process.

Furthermore, H2AX levels for HEK293 and MRC 5 cell lines overexpressing LRP::FLAG were also analyzed. The significant decrease in H2AX in both HEK293 and MRC 5 cell lines overexpressing LRP::FLAG provide an effective means at eliminating DNA damage, especially DNA damage associated with dysfunctional telomeres characteristic in cellular ageing of cells.

H2AX foci:

DNA damage that accumulates throughout a cell's replicative life span is a major factor influencing cell cycle arrest and senescence onset. This damage arises due to a loss of protection as telomeres erode exposing genomic DNA to an increased amount of genotoxic stresses that generate double stranded breaks. In an attempt to repair DNA the DNA damage response (DDR) pathway is activated and the cell cycle is impeded (Pospelova et al., 2009). In this regard, if the damage is too severe to repair, cell cycle arrest is maintained and senescence or apoptosis is induced. This said, sites of DNA damage/double stranded breaks are marked by phosphorylated histones known as γ-H2AX foci, which are responsible for initiating the DDR and cell cycle arrest (Pospelova et al., 2009). Therefore, as cells age they accumulate these damage sites causing a corresponding increase in γ-H2AX which can serve as markers for aging. Incidentally, the accumulation of these foci serves as an efficient mode to track cellular senescence in conjunction to measuring telomere length (Pospelova et al., 2009). Interestingly, western blot analysis of H2AX revealed a striking reduction of the protein in both HEK293 and MRC 5 cells overexpressing LRP::FLAG. The significant reduction of this protein offers to possible explanations: the first being that the overexpression of LRP::FLAG or fragment thereof effectively boosts the DNA repair process to ensure that only a minimal amount of damage is present in the cells at any given time. Alternatively, the overexpression of this protein may in fact provide an additional protective effect to prevent the accumulation of DNA damage. This would not only impede the onset of senescence but would also improve overall cell fitness.

Cellular Ageing/Senescence:

We have shown that LRP::FLAG overexpression (or a fragment thereof i.e. LRP102-295::FLAG) significantly elevates telomerase activity while decreasing senescent markers, indicating the cellular process of senescence is impeded. In turn, the impediment of senescence would effectively prevent cellular degeneration and as a result tissue degeneration as well. On a whole organism scale this could potentially aid in preventing organ atrophy by allowing cells an extended proliferation to replace old and damaged tissue and to allow the preservation of organ fitness. Additionally, the extended cellular proliferation that the overexpression of LRP::FLAG and subsequent elevation of telomerase activity would aid in impeding muscle degeneration, loss of bone mass, skin atrophy, hair loss/graying of hair as well as a loss of immune system efficacy. This would occur as extension of the telomeres following overexpression of LRP::FLAG would allow for longer lived healthier cells with elevated proliferative potentials.

Age-Related Diseases:

Many age related diseases such as for example osteoporosis, type II diabetes, atherosclerosis and cardiovascular disease, are caused by loss of cellular proliferation and many of the disease affected tissue areas contain cells with critically shortened telomeres. Therefore, as LRP::FLAG (or a fragment thereof) has been shown to increase telomerase activity and elongate telomeres it could potentially be utilised in the treatment of age-related diseases to restore proliferative potential to the cells.

Accelerated Ageing Disorders:

The overexpression of LRP::FLAG (or a fragment thereof) and its restorative effect to keep cells fit and proliferating could potentially be used as a potential treatment for accelerated ageing disorders. One such disorder includes: Hutchinson-Gilford progeria—A genetic disorder caused by alternative splicing of the lamin gene causing the accumulation of the protein progeria, which ultimately disrupts nuclear morphology to cause enhanced DNA and cell damage. The protein progerin itself is also expressed during normal healthy ageing due to alternative splicing patterns and has been directly linked to telomere erosion (Cao et al., 2011). The damage caused by this protein further accelerates the loss of the telomeric ends of chromosomes and exhausts cell's proliferative capacity. The disorder is characterized by a rapid ageing of the body and organs, atherosclerosis, osteoporosis, amyotrophy (wasting of muscle), skin atrophy, loss of subcutaneous tissue and fat, and hair loss. This said, the reduction of this protein as well as the other observed markers (progerin, H2AX and β-galactosidase) upon LRP::FLAG overexpression could potentially offer a palliative treatment to restore telomere length and extend proliferative potential of the cells. This would slow down the progression of the disease and alleviate some of the symptoms associated with the disease.

Concluding Remarks:

Telomere biology is the core regulatory mechanism for the ageing process in humans. Thus, it is one of the key aspects to assess when studying senescence and ageing. It was found that in HEK293 cells and MRC 5 cells overexpressing the LRP::FLAG that hTERT levels were subsequently increased. The elevated levels of hTERT resulted in a corresponding increase in telomerase activity, which was also confirmed. Consequently, it has been shown that an introduction or increased expression of the hTERT sub-unit is sufficient to reduce levels of senescent markers and inhibit the ageing process in cells (de Jesus et al., 2012; Tomas-Loba et al., 2008; Bodnar et al, 1998). This suggests that not only does LRP/LR share an interaction/association with hTERT, but may in fact play a role in promoting the production of endogenous hTERT. In relation, this increased expression of hTERT may convey increased mitochondrial protection against free radicals, to further promote cell viability by reducing the amount of cellular damage that occurs (Sharma et al., 2012).

To confirm that the increased telomerase activity observed in HEK293 cells and MRC 5 cells overexpressing LRP::FLAG was indeed maintaining the length of telomeres, qPCR was performed. It was confirmed that telomere length was indeed maintained. In fact, overall length was found to have increased in transfected cells. This indicated that the elevated telomerase was sufficient to prevent an accumulation of short telomeres and thereby induce an anti-ageing effect (de Jesus et al., 2012). The induction or elevation of hTERT in normal human cells induces telomerase activity to elongate telomeres (Bodnar et al., 1998; Tomas-Loba et al., 2008). This elongation allows cells to revert the ageing process, and essentially immortalize themselves. The elevated levels of hTERT resulted in an increase in telomere length, which is not conventionally expected (Liu and Yung, 1998; Wick et al., 1999). Increasing and/or maintaining telomere length is important to impede cellular senescence (cellular ageing). In support, the reduction of senescent markers further substantiates that the telomere replenishment occurring is in fact impeding senescence (de Jesus et al., 2012). Thus enabling cells to revert to a younger state and maintain it, to effectively inhibit the cellular ageing process.

In conclusion, co-localization of hTERT with LRP/LR and LRP::FLAG is confirmed and occurs predominantly in the perinuclear compartments of HEK293 and MRC 5 cells overexpressing LRP::FLAG. Additionally, this co-localization was found to be a novel interaction between LRP/LR and hTERT. Moreover, overexpression of LRP::FLAG caused a significant reduction in senescent markers SA-β-galactosidase, progerin and/or H2AX foci. Furthermore, the overexpression of LRP::FLAG causes a strong elevation in hTERT levels, telomerase activity and telomere length in HEK293 cells and MRC 5 cells overexpressing LRP::FLAG. These findings suggest a novel function of LRP/LR and telomerase in the process of cellular ageing. Therapeutic use of LRP/LR or a fragment thereof may include use in the treatment and/or prevention of ageing or the impediment of cellular senescence and may include use wherein diseases and/or medical conditions relate to the irregular and/or abnormal and/or increased and/or early onset of cellular senescence in a human or animal including, but not limited to, the following group: dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease.

Non-therapeutic use LRP/LR or a fragment thereof may include use in the prevention and/or treatment and/or impeding of muscle degeneration, loss of bone mass, skin atrophy, hair loss, graying of hair and/or a loss of immune system efficacy.

Co-localization between LRP/LR and hTERT shows an interaction between the two proteins. The Applicant was surprised at this finding of co-localization between the two proteins. The Applicant is unaware of any suggestion and/or motivation in the prior that would suggest that given the plethora of proteins inside a cellular environment that these two specific proteins, namely LRP/LR and hTERT, would share an interaction. Further still, the Applicant is unaware of any suggestion and/or motivation in the prior art that overexpression or upregulation of LRP/LR would cause any one or more of (i) increased levels of hTERT, (ii) increased telomere activity, and (iii) increased telomere length, all three of which treats and/or prevents and/or delays the onset of cellular ageing. Moreover, expression of LRP/LR, shown in Example 1 as LRP/LR::FLAG, caused a significant reduction in senescent markers SA-β-galactosidase, 2HAX foci and progerin, known to be associated with ageing. Consequently, the claimed invention is considered by the Applicant to be both novel and inventive.

Figure 8I:
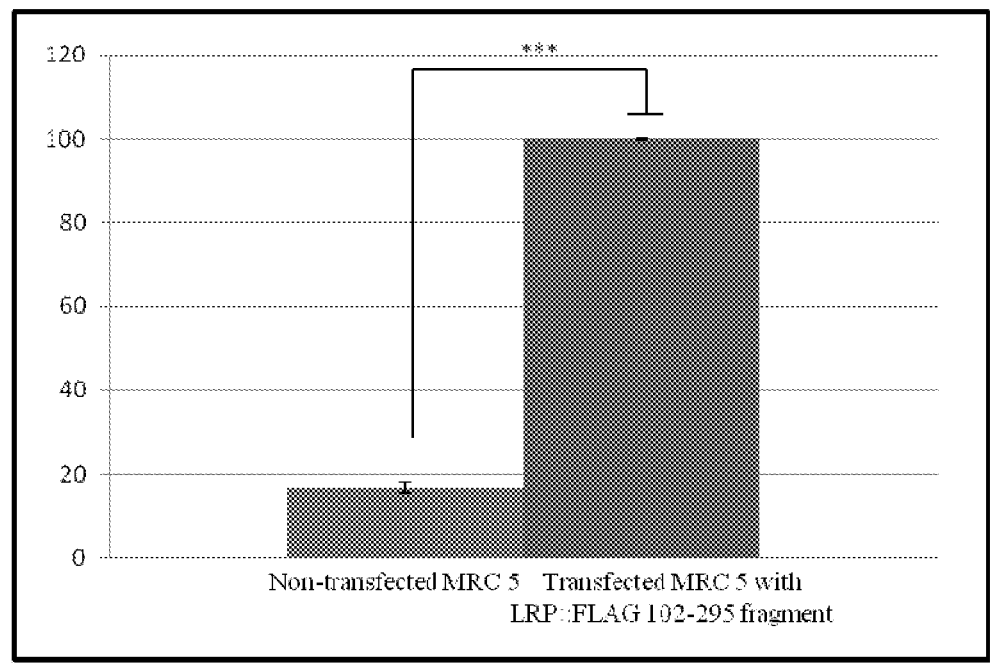
FIG. 8I shows a fragment of LRP (i.e. LRP102-295::FLAG) overexpression in MRC 5 cells induces a significant (83.4%) increase in telomerase activity for MRC 5 transfected cell lines.

LRP102-295::FLAG fragment overexpression induces a significant increase in telomerase activity for MRC 5 transfected cells as seen in FIG. 8I. The peptide/protein sequence of the LRP fragment 102-295 corresponds to the sequence listing as set forth in SEQ ID NO: 5.

LRP/LR is predominantly located on the cell surface (Gauczynski et al., 2001; Jovanovic et al., 2015). Consequently, it is very surprising that there would be any interaction with hTERT predominantly found in the nucleus. Although it has been reported that LRP/LR may be found to a lesser extent intracellularly in the cytosolic and nuclear regions, the shear plethora of proteins, peptide and the like inside the nuclear regions, and that fact that LRP/LR is much less prevalent in the nuclear regions would dissuade any person skilled in the art to investigate (i) increased levels of hTERT, (ii) increased telomere activity, and (iii) increased telomere length through providing a cell with increased LRP/LR. In the above cellular regions, LRP/LR performs numerous physiological and biochemical functions to promote cell viability. In addition, this protein allows the binding and interaction of a broad range of extracellular components and proteins (Gauczynski et al., 2001a). A few of the extracellular components that LRP/LR binds include: carbohydrates, elastin, prions on the cell surface and laminin-1 to which it shares a high affinity (Mercurio, 1995).

LRP/LR is a transmembrane protein and the fragment LRP 102-295 that corresponds to the SEQ ID NO: 5 is an extracellular portion of the transmembrane protein extending into the extracellular matrix of the cell. It is therefore wholly surprising and unexpected that MRC 5 cells overexpressing LRP 102-295::FLAG would result in an increase in telomerase activity as illustrated in FIG. 8I. As stated above, the skilled person would be dissuaded from investigating (i) increased levels of hTERT, (ii) increased telomere activity, and (iii) increased telomere length through providing a cell with increased LRP/LR. Moreover, the skilled person would be further dissuaded from investigating the aforementioned using a fragment of LRP/LR (namely LRP 102-295::FLAG) which corresponds to an extracellular portion of LRP/LR since the hTERT (impacting on telomerase activity) is found in the nucleus.

Since LRP/LR performs numerous physiological and biochemical functions any use thereof in the treatment of disease in a human or animal or as a pharmaceutical composition would need to undergo detailed animal and/or clinical trials. However, use of a fragment of LRP/LR (such as LRP 102::FLAG) in the treatment of disease in a human or animal or in the non-therapeutic treatment of ageing or as a pharmaceutical composition would significantly reduce the amount and extent of animal and/or clinical trials since the possible physiological and biochemical functions and/or interactions would be lessened. This unexpectedly and surprisingly provides that the fragment of LRP/LR (LRP 102-

295) is ideally placed for use in the impediment of cellular senescence and/or the therapeutic treatment of diseases such as but not limited to: dyskeratosis congenital, cancer, idiopathic pulmonary fibrosis, Hoyeraal-Hreiderasson syndrome, Hutchinson-Gilford progeria, aplastic anemia and age-related diseases including for example osteoporosis, type II diabetes, atherosclerosis and cardiovascular disease.

The fragment of LRP/LR (LRP 102-295) is also ideally placed for use in the impediment of cellular senescence in the non-therapeutic use LRP/LR or a fragment thereof which may include use in the prevention and/or treatment and/or impeding of muscle degeneration, loss of bone mass, skin atrophy, hair loss, graying of hair and/or a loss of immune system efficacy.

REFERENCES (EXAMPLE 1)

Allsopp, R. C., & Harley, C. B. (1995). Evidence for a critical telomere length in senescent human fibroblasts. Exp. Cell. Res. 219(1), 130-136.

Bodnar, A. G., Ouellette, M., Frolkis, M., Holt, S. E., Chiu, C., Morin, G. B., Harley, C. B., Shay, J. W., Lichtsteiner, S., and Wright, W. E. (1998). Extension of Life-Span by Introduction of Telomerase into Normal Human Cells. Science. 279, 349-352.

Cao, K., Blair, C. D., Faddah, D. a., Kieckhaefer, J. E., Olive, M., Erdos, M. R., Nabel, E. G., and Collins, F. S. (2011). Progerin and telomere dysfunction collaborate to trigger cellular senescence in normal human fibroblasts. J. Clin. Invest. 121, 2833-2844.

Capper, R., Britt-Compton, B., Tankimanova, M., Rowson, J., Letsolo, B. T., Man, S., Haughton, M., and Baird, D. M. (2007). The nature of telomere fusion and a definition of the critical telomere length in human cells. Genes Dev. 21, 2495-2508.

Cawthon, R. M. (2002). Telomere measurement by quantitative PCR. Nucleic Acids Res. 30, 1-6.

Chetty, C., Khumalo, T., Da, B., Dias, C., Reusch, U., Knackmuss, S., Little, M., and Weiss, S. F. T. (2014). Anti-LRP/LR Specific Antibody IgG1-iS18 Impedes Adhesion and Invasion of Liver Cancer Cells. PLoS One. 9, 1-10.

Chin, L., Artandi, S. E., Shen, Q., Tam, A., Lee, S. L., Gottlieb, G. J., Greider, C. W., and DePinho, R. a. (1999). P53 Deficiency Rescues the Adverse Effects of Telomere Loss and Cooperates With Telomere Dysfunction To Accelerate Carcinogenesis. Cell. 97, 527-538.

Cong, Y., & Shay, J. W. (2008). Actions of human telomerase beyond telomeres. Cell research, 18(7), 725-732.

Da Costa Dias, B., Jovanovic, K., Gonsalves, D., Moodley, K., Reusch, U., Knackmuss, S., Weinberg, M. S., Little, M., and Weiss, S. F. T. (2014). The 37 kDa/67 kDa Laminin Receptor acts as a receptor for A b 42 internalization. Sci. Rep. 4, 1-11.

de Jesus, B. B., Vera, E., Schneeberger, K., Tejera, A. M., Ayuso, E., Bosch, F., & Blasco, M. A. (2012). Telomerase gene therapy in adult and old mice delays aging and increases longevity without increasing cancer. EMBO molecular medicine. 4(8), 691-704.

de Lange, T. (2005). Shelterin: The protein complex that shapes and safeguards human telomeres. Genes Dev. 19, 2100-2110.

Dimri, G. P., Lee, X., Basile, G., Acosta, M., Scott, G., Roskelley, C., Medrano, E. E., Linskens, M., Rubelj, I., and Pereira-Smith, O. (1995). A biomarker that identifies senescent human cells in culture and in aging skin in vivo. Proc. Natl. Acad. Sci. U.S.A. 92, 9363-9367.

Gauczynski, B. Y. S., Hundt, C., Leucht, C., and Weiss, S. (2001a). Interaction of prion proteins with cell surface receptors, molecular chaperones, and other molecules. Adv. Protein Biochem. 57, 229-272.

Gauczynski, S., Nikles, D., El-gogo, S., Papy-garcia, D., Alban, S., Barritault, D., Lasme, C. I., and Weiss, S. (2006). The 37-kDa/67-kDa Laminin Receptor Acts as a Receptor for Infectious Prions and Is Inhibited by Polysulfated Glycanes. JID. 194, 702-709.

Griffith, J. D., Comeau, L., Rosenfield, S., Stansel, R. M., Bianchi, A., Moss, H., Hill, C., and Carolina, N. (1999). Mammalian Telomeres End in a Large Duplex Loop. Cell. 97, 503-514.

Harley, C. B., and Villeponteau, B. (1995). Telomeres and telomerase in aging and cancer. Curr. Opin. Genet. Dev. 5, 249-255.

Harley, C. B., Futcher, A. B., and Greider, C. W. (1990). Telomeres shorten during ageing of human fibroblasts. Nat. 345, 458-460.

Hayflick, L. (1965). The limited in vitro lifetime of human diploid cell strains. Exp. Cell Res. 636, 614-636.

Hiyama, E., Gollahon, L., Kataoka, T., Yokoyama, T., Gazdar, A. F., Hiyama, K., Piatyszek, M. A., and Shay, J. W. (1996). Telomerase Activity in Human Breast Tumors. J. Natl. Cancer Inst. 88, 116-122.

Jovanovic, K., Loos, B., Da Costa Dias, B., Penny, C., and Weiss, S. F. T. (2014). High Resolution Imaging Study of Interactions between the 37 kDa/67 kDa Laminin Receptor and APP, Beta-Secretase and Gamma-Secretase in Alzheimer's Disease. PLoS One. 9, 1-10.

Jovanovic, K., Chetty, C. J., Khumalo, T., Da Costa Dias, B., Ferreira, E., Malindisa, S. T., Caveney, R., Letsolo, B. T., and Weiss, S. F. (2015). Novel patented therapeutic approaches targeting the 37/67 kDa laminin receptor for treatment of cancer and Alzheimer's disease. Expert Opin. Ther. Pat. 1-16.

Khumalo, T., Ferreira, E., Jovanovic, K., Veale, R. B., & Weiss, S. F. (2015). Knockdown of LRP/LR Induces Apoptosis in Breast and Oesophageal Cancer Cells. PLoS one. 10(10), e0139584.

Kim, N. W., Piatyszek, M. A., Prowse, K. R., Harley, C. B., West, M. D., Ho, P. L. C., Coviello, G. M., Wright, W. E., Weinrich, S. L., and Shay, J. W. (1994). Specific Association of Human Telomerase Activity with Immortal Cells and Cancer. Science. 266, 2011-2015.

Lin, T. T., Letsolo, B. T., Jones, R. E., Rowson, J., Pratt, G., Fegan, C., Pepper, C., and Baird, D. M. (2010). Telomere dysfunction and fusion during the progression of a human malignancy. Blood. 44, 1899-1908.

Liu, W. H. and Yung, B. Y. M. (1998). Oncogene. 17. 3055-3064.

López-Otin, C., Blasco, M. A., Partridge, L., Serrano, M., & Kroemer, G. (2013) The Hallmarks of Aging. Cell. 153 (6), 1194-1217.

Mattern, K. a, Swiggers, S. J. J., Nigg, a L., Löwenberg, B., Houtsmuller, a B., and Zijlmans, J. M. J. M. (2004). Dynamics of protein binding to telomeres in living cells: implications for telomere structure and function. Mol. Cell. Biol. 24, 5587-5594.

Mercurio, A. M. (1995). Laminin receptors: Achieving specificity through cooperation. Trends Cell Biol. 5, 419-423.

Miller, D. M., and Shakes, D. C. (1995). Immunofluorescence microscopy. Methods Cell Biol. 48, 365-394.

Naidoo, K., Malindisa, S. T., Otgaar, T. C., Bernert, M., Da Costa Dias, B., Ferreira, E., Reusch, U., Knackmuss, S., Little, M., Weiss, S. F. T. and Letsolo, B. T. Knock-down of the 37 kDa/67 kDa laminin receptor LRP/LR impedes telomerase activity. PLoS One. in press—not yet published as at 5 Nov. 2015.

Nakamura, T. M., and Cech, T. R. (1998). Reversing Time: Origin of Telomerase. Cell. 92, 587-590.

Pospelova, T. V., Demidenko, Z. N., Bukreeva, E. I., Pospelov, V. A., Gudkov, A. V. and Blagosklonny, M. V., (2009). Pseudo-DNA damage response in senescent cells. Cell cycle, 8(24), 4112-4118.

Sharma, N. K., Reyes, A., Green, P., Caron, M. J., Bonini, M. G., Gordon, D. M., et al. (2012) Human telomerase acts as a hTR-independent reverse transcriptase in mitochondria. Nucleic Acids Res. 40, 712-725.

Shay, J. W., Pereira-Smith, O. M., & Wright, W. E. (1991). A role for both RB and p53 in the regulation of human cellular senescence. Exp. Cell. Res. 196(1), 33-39.

Shay, J. W., & Wright, W. E. (2007). Hallmarks of telomeres in ageing research. The Journal of pathology. 211(2), 114-123.

Schluth-Bolard, C., Ottaviani, A., Bah, A., Boussouar, A., Gilson, E., Magdinier, F. (2010) Dynamics and plasticity of chromosome ends: consequences in human pathologies. Atlas Genet Cytogenet Oncol Haematol. 14(5), 501-524.

Tomas-Loba, A., Flores, I., Ferna, P. J., Cayuela, L., Maraver, A., Serrano, M., Tejera, A., Borra, C., Matheu, A., Klatt, P., et al. (2008). Telomerase Reverse Transcriptase Delays Aging in Cancer-Resistant Mice. Cell. 135, 609-622.

Towbin, H., Staehelint, T., and Gordon, J. (1979). Electrophoretic transfer of proteins from polyacrylamide gels to nitrocellulose sheets: Procedure and some applications. Proc. Natl. Acad. Sci. U.S.A. 76, 4350-4354.

Townsley, D. M., Dumitriu, B., and Young, N. S. (2014). Bone marrow failure and the telomeropathies. Blood. 124(18), 2775-2783.

Vana, K., & Weiss, S. (2006). A trans-dominant negative 37 kDa/67 kDa laminin receptor mutant impairs PrP Sc propagation in scrapie-infected neuronal cells. J. Mol. Biol. 358(1), 57-66.

Wick, M., Zubov, D. and Hagen, G. (1999). Gene. 232(1). 97-106.

Example 2—Compounds for Use in the Treatment of Telomere Related Diseases and/or Telomere Related Medical Conditions, Specifically Cancer Experimental Procedure (Example 2)

Cell Culture:

Human embryonic kidney cells (HEK293) were cultured in Dulbecco's Modified Eagle Medium (DMEM) high glucose (Hyclone). MDA_MB231 breast cancer cells were cultured in DMEM/Ham's-F12 (1:1). All media was supplemented with 10% fetal calf serum (FCS) and 1% penicillin/streptomycin. The cells were cultured at 37° C. and 5% $CO_2$. Non-tumorigenic HEK293 cells were used as the positive control as they exhibit high telomerase activity whereas the tumorigenic MDA_MB231 cells were used as the experimental model as they are tumorigenic and metastatic.

Reagents and Antibodies:

IgG1-iS18 was recombinantly produced in a mammalian expression system as described by Zuber et al., (2008) [36]. Flow Cytometric Analysis of Cell Surface and Intracellular Levels:

Quantification of cell surface and intracellular levels of LRP/LR and hTERT was conducted using flow cytometry. Trypsin/EDTA was used to facilitate detachment of adherent cells which was followed by centrifugation at 1200 rpm for 10 minutes. Cells were subsequently fixed by re-suspending them for 10 minutes at 4° C. in 4% paraformaldehyde. Cells were then permeabilised by resuspension in methanol for 30 minutes to detect intracellular levels. Cells were again centrifuged in FACS buffer which allowed for the preparation of two cell suspensions, one to which anti-LRP/LR specific antibody IgG1-iS18 was added to detect LRP/LR and anti-telomerase reverse transcriptase was added to detect hTERT in another. The cell suspension containing only PBS but no antibody was used as the negative control. All suspensions were incubated at room temperature for 1 hour. Following three washing steps with 1×PBS, anti-human-FITC coupled secondary (Sigma Aldrich) was added to each cell suspension to detect LRP/LR and APC-coupled to detect hTERT, followed by another 1 hour incubation period. Furthermore, three post-incubation washes were performed and cell suspensions were analysed using the BD Accuri C6 flow cytometer. The experiments were performed in triplicate and repeated at least three times.

Confocal Microscopy:

In order to visualize the co-localization of LRP/LR and hTERT on the cell surface and intracellularly, confocal microscopy was employed. Cells were first seeded on coverslips and allowed to reach 70% confluency. Cells were fixed in 4% formaldehyde in PBS for approximately 15 minutes followed by several washes with PBS. Cells were permeabilised for intracellular visualization with Triton-X BSA solution for 15 minutes followed by several washes. Cells were blocked in 0.5% BSA in PBS for 5-10 minutes. After washing with 1×PBS, excess PBS was blotted off. The cover slips containing cells were placed on a glass slide (with cells facing upwards) and this was followed by addition of primary antibody IgG1-iS18 (1:100) diluted in 0.5% BSA and anti-Telomerase reverse transcriptase (1:100) diluted in 0.5% BSA and incubated at 4° C. overnight. At the end of incubation period, the coverslips were rinsed thrice in PBS/BSA and incubated with FITC-coupled and APC-coupled secondary antibodies (diluted in 0.5% BSA) for 1 hour in the dark. After which, the cells were again rinsed thrice as before. Thereafter, Hoechst 33342 diluted in PBS was administered for 5-10 minutes. Cells were finally washed once in PBS alone and mounted onto a clean slide using GelMount (Sigma-Aldrich). A period of 45 minutes was allocated to allow for setting to take place. Images were acquired at room temperature with 60× magnification using the Olympus IX71 Immunofluorescence Microscope and Olympus XM10 greyscale camera analysis. Research Image Processing Software was used to capture the images.

FLAG® Co-Immunoprecipitation Assay (Pull Down Assay):

To assess whether there is an interaction between LRP/LR and hTERT, HEK293 cells were transfected with pCIneo-moLRP::FLAG [37] using Lipofectamine 3000 and cultured to stably express the LRP::FLAG as per the manufacturer's instructions (Invitrogen). The cell lysate was produced from both non-transfected HEK293 cells (lacking the LRP::FLAG) as well as HEK293 cells transfected with pCIneo-moLRP::FLAG. A modified procedure using FLAG® Immunoprecipitation Kit (Sigma-Aldrich) was then used to selectively bind the FLAG peptide. This involved incubating cell lysates with the Anti-FLAG M2 beads in Eppendorf tubes at 4° C. overnight. Thereafter, three washes were performed with 1× wash buffer provided in the kit. The washes were then collected as they contained unbound protein. Proteins were then collected and analysed by western blotting. The murine anti-FLAG (Sigma F-3165) (1:4000) and rabbit anti-hTERT (Abcam ab 183105) (1:1000) primary antibodies were used to detect LRP::FLAG and hTERT, respectively. These were then detected using anti-rabbit IgG (Cell signalling 7074S) and anti-murine IgG (Sigma A4416) secondary antibodies coupled with an HRP enzyme.

Western Blotting and SDS-PAGE:

Western blotting was used to determine the protein levels of LRP post-transfection with siRNA-LAMR1 when compared to untreated controls, with β-actin used as the loading control. Briefly, cells were lysed, protein levels quantified and 5 µg of cell lysate was resolved on a polyacrylamide gel. The proteins were subsequently transferred to a polyvinylidene fluoride (PVDF) membrane for 45 minutes at 350 mV and a semi-dry transferring apparatus. The membrane was blocked in a 1:10 000 solution of the LRP-specific primary antibody IgG1-iS18 in 3% BSA in PBS-Tween at 4° C. overnight, with shaking. The membrane was subsequently washed in PBS-Tween, and further incubated in a 1:10 000 solution of anti-human HRP secondary antibody in 3% BSA in PBS-Tween for 1 hour at room temperature with shaking, and washed as before prior to being analysed.

siRNA-Mediated Down-Regulation of LRP:

HEK293 and MDA_MB231 cells were transfected for LRP knockdown with siRNA purchased from Dharmacon, Cat #J-013303-08, according to manufacturer's instructions using DharmaFECT® 1-transfection reagent. Control siRNA used—Cat #D-001810-04-20. Mission siRNA universal negative control (SIC001—Sigma Aldrich) was used according to manufacturer's instructions as a negative control for the experiment.

Detection of Telomerase Activity:

The Applicant utilized the TRAPeze RT® Telomerase detection Kit (Merck Millipore) to determine telomerase activity according to manufacturer's instructions with minor modifications. Briefly, cells were harvested and washed in PBS. The cells were then lysed with CHAPS lysis buffer. Protein and RNA were collected in the supernatant. Protein concentration was standardized to 500 ng/µl for all experimental and control reactions. All samples were then subjected to experimental analysis accompanied by two controls; heat treatment at 85° C. for 10 minutes and control reaction containing a PCR inhibitor as per the manufacturer's instruction. All reactions were performed in triplicate. The reactions were carried out in the LightCycler LC480 (Roche) under the following cycling conditions: 37° C. for 30 minutes, 95° C. for 2 minutes and 45 cycles of 95° C. for 15 seconds, 59° C. for 60 seconds and 45° C. for 10 seconds. Telomerase activity was estimated by extrapolation from the standard curve generated by 1:10 serial dilutions (40-0.4 amoles) of TSR8 control as per Merck Millipore instructions. The data was analysed in LightCycler® Software version 1.5.1.

Data Analysis and Statistics:

Statistical analysis was conducted in Graphpad Prism version 5.03. All statistical analyses were performed using a two-tailed Student's t-test with a 95% confidence interval. P-values of less than 0.05 were considered significant. The linear dependencies between two variables were expressed using Pearson's (r) correlation co-efficient.

Results (Example 2)

Human Embryonic Kidney and Metastatic Breast Cancer Cells Display LRP/LR and hTERT on the Cell Surface and Intracellularly:

Since the overexpression of LRP/LR and hTERT has been observed in numerous cancer cell lines, the levels of LRP/LR and hTERT on the cell surface and intracellularly on HEK293 and MDA_MB231 cells were examined by flow cytometry. HEK293 and MDA_MB231 cells displayed high levels of LRP/LR and hTERT on both the cell surface and intracellularly (FIG. 11A to 11E). Of the assessed HEK293 cell population, 72.22% and 97.98% of the cells expressed intracellular LRP/LR and hTERT, respectively. MDA_MB231 cells exhibited 98.82% and 94.54% of LRP/LR and hTERT intracellularly, respectively (FIG. 11). The levels of LRP/LR and hTERT on the cell surface were similarly determined. Flow cytometry revealed that 75.26% and 98.56% of HEK293 cells expressed LRP/LR and hTERT on the cell surface, respectively. MDA_MB231 cells expressed 99.17% and 95.86% of LRP/LR and hTERT on the cell surface, respectively (FIG. 11). The results confirmed that HEK293 and MDA_MB231 cells display high levels of LRP/LR. However, this is the first report noting the levels of hTERT both intracellularly and on the cell surface on these two cell lines.

Figure 12A:
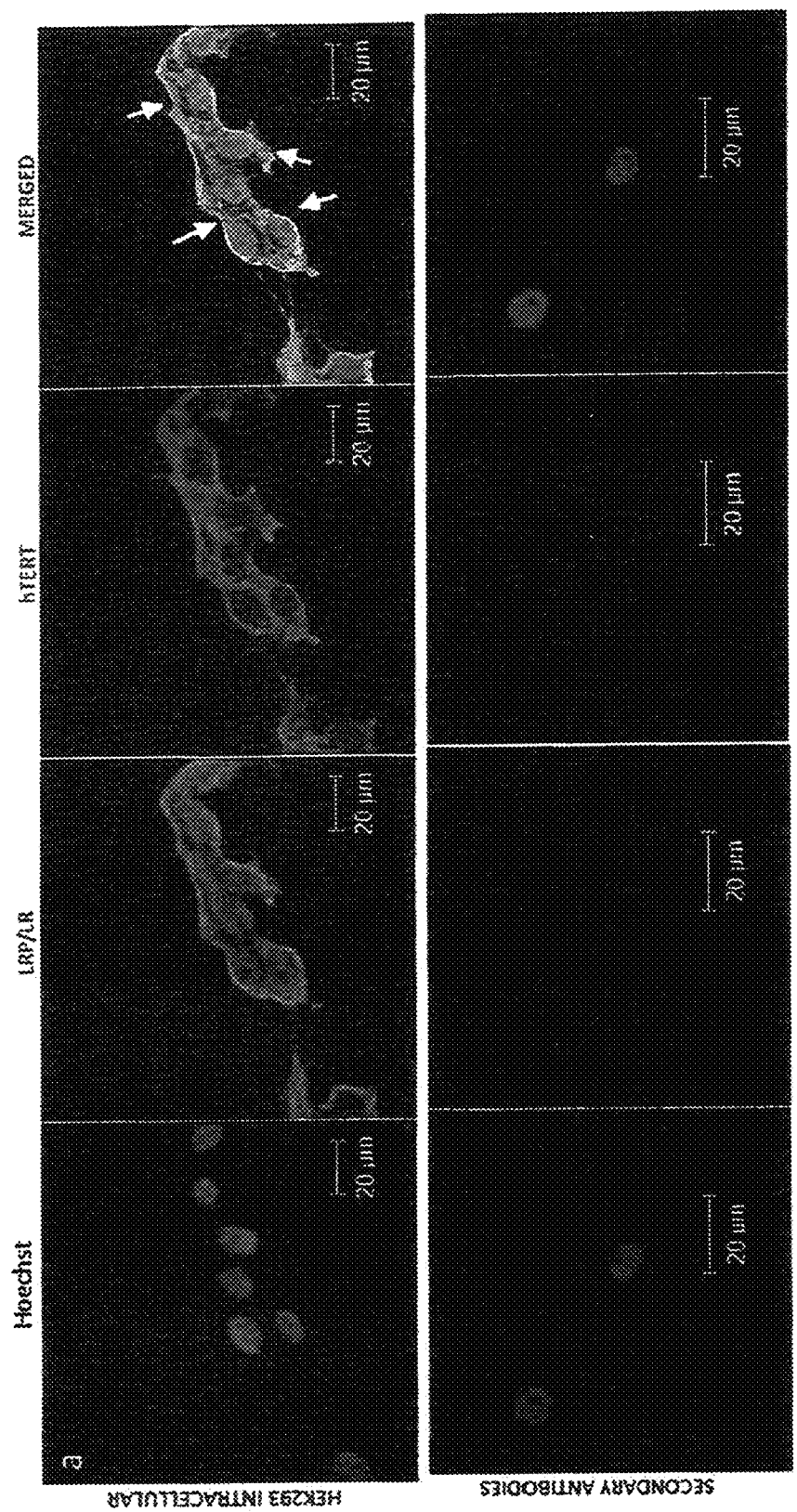
FIG. 12A shows confocal microscopy analysis of the interaction between LRP/LR and hTERT on MDA_MB231 and HEK293 cells. Particularly, 11A shows intracellular LRP/LR and hTERT on immunolabelled HEK293 cells.
Figure 12B:
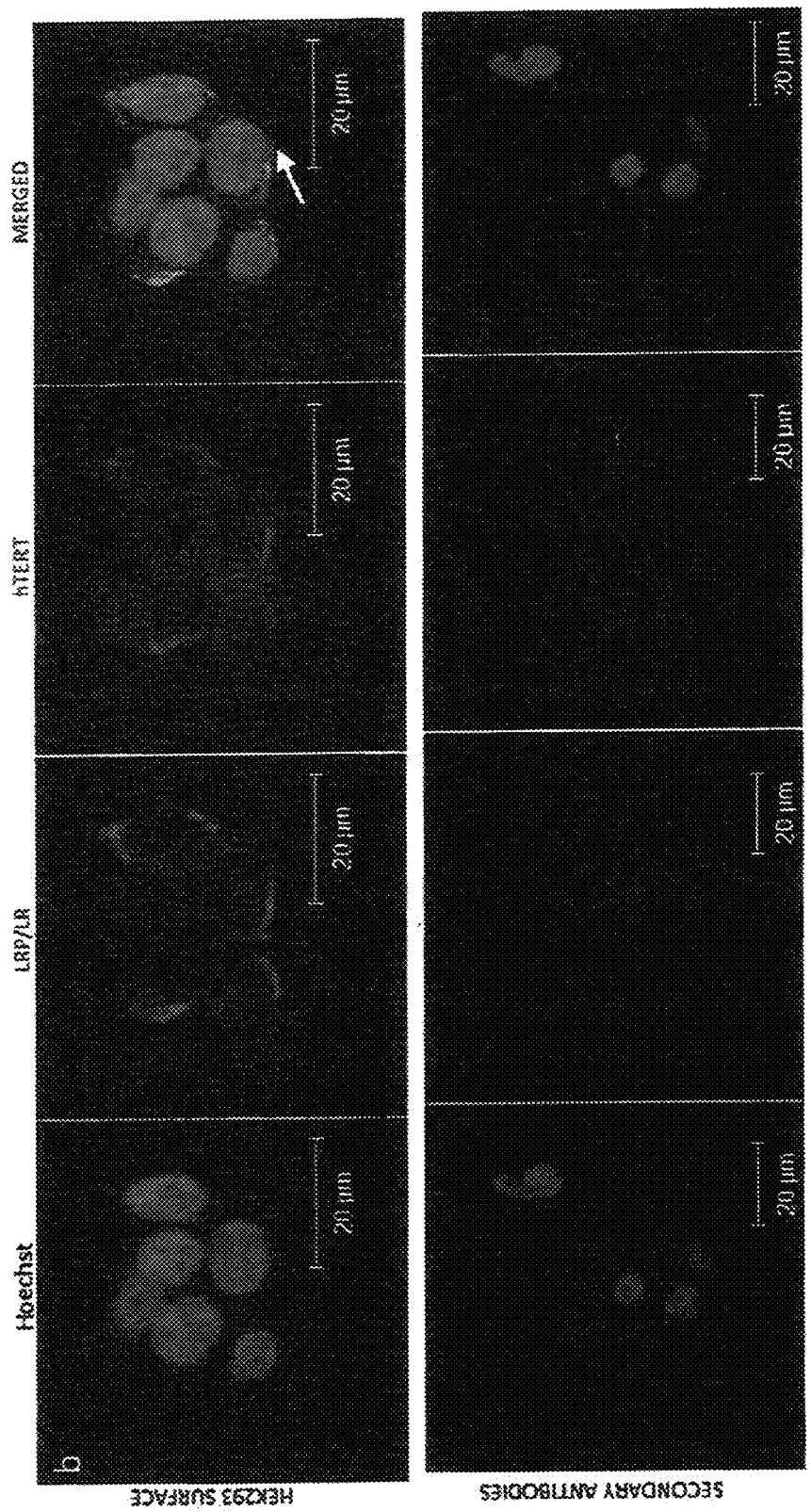
FIG. 12B shows confocal microscopy analysis of the interaction between LRP/LR and hTERT on MDA_MB231 and HEK293 cells. Particularly, 11B shows endogenous cell surface LRP/LR and hTERT on immunolabelled HEK293.
Figure 12C:
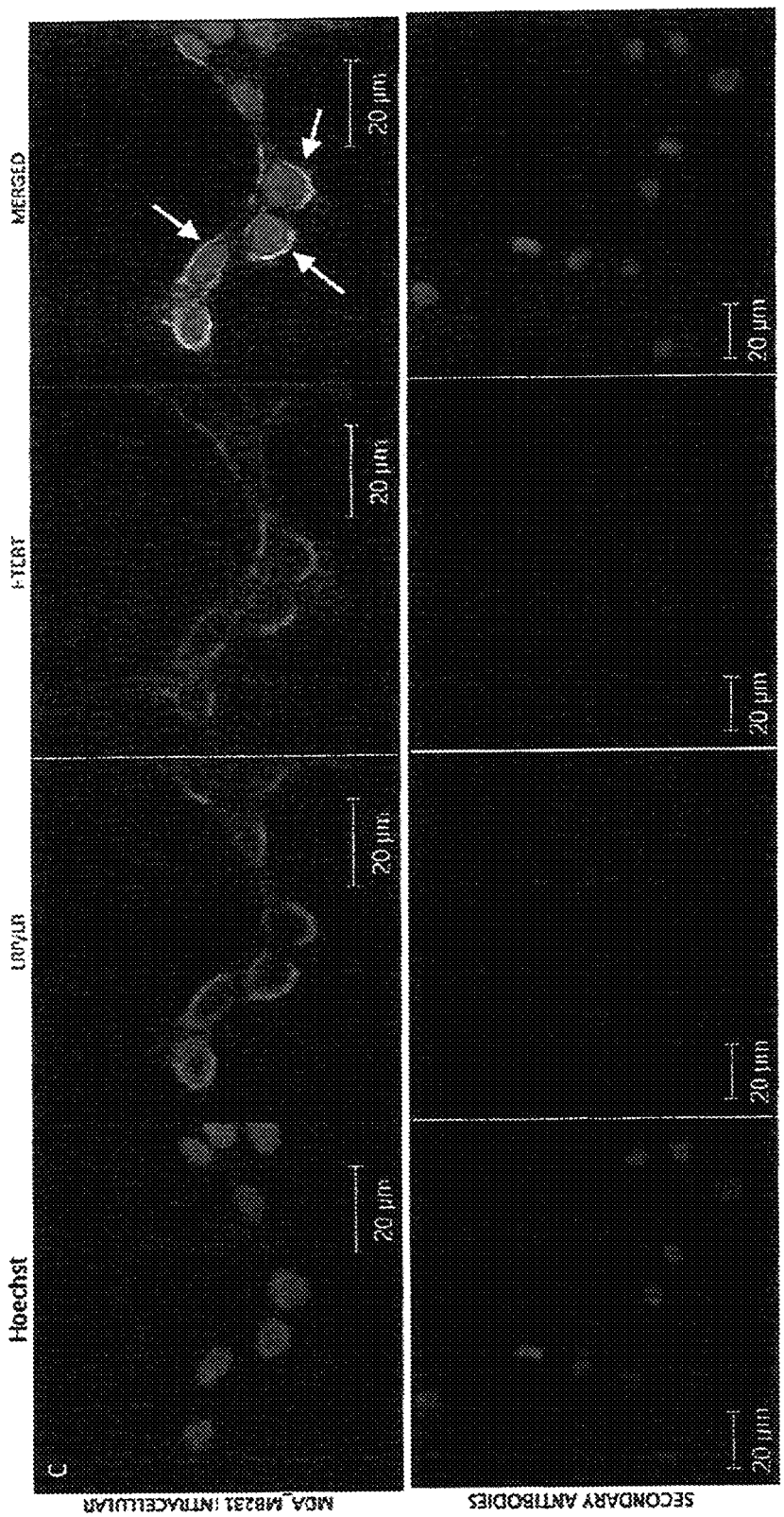
FIG. 12C shows confocal microscopy analysis of the interaction between LRP/LR and hTERT on MDA_MB231 and HEK293 cells. Particularly, 11C shows intracellular LRP/LR and hTERT on immunolabelled MDA_MB231 cells.
Figure 12D:
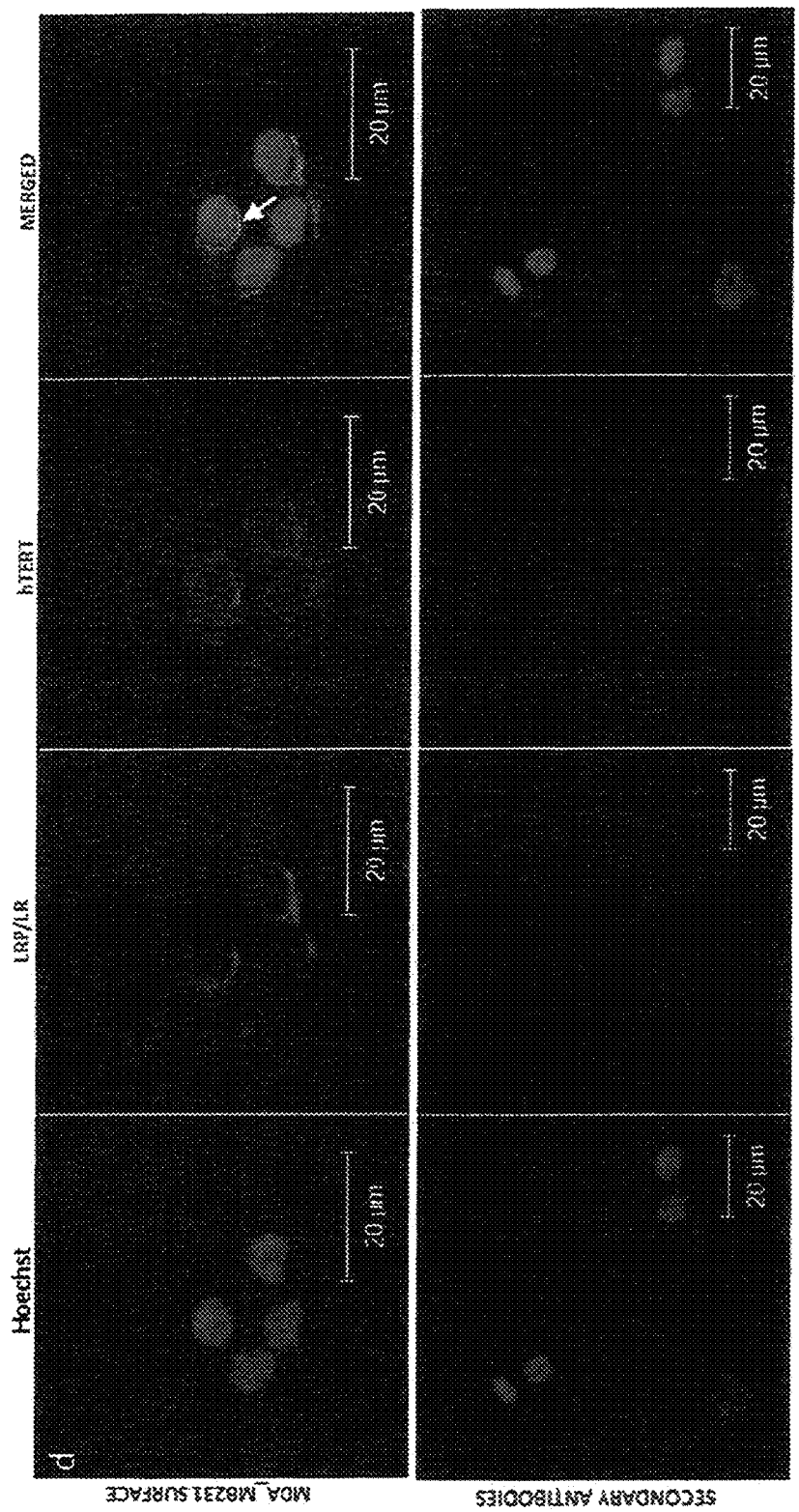
FIG. 12D shows confocal microscopy analysis of the interaction between LRP/LR and hTERT on MDA_MB231 and HEK293 cells. Particularly, 11D shows endogenous cell surface LRP/LR and hTERT on immunolabelled MDA_MB231.

LRP/LR Co-Localizes with hTERT on the Cell Surface and in the Perinuclear Compartments:

Confocal microscopy was employed to investigate whether LRP/LR and hTERT co-localize on the cell surface as well as intracellularly, as sharing a similar cellular localization may be indicative of a possible association between these proteins. Co-localization of LRP/LR and hTERT was detected on the cell surface of non-permeabilised HEK293 and MDA_MB231 cells (FIG. 12b,d) and pronounced in the perinuclear compartments of permeabilised HEK293 and MDA_MB231 cells (FIG. 12a,c). These results demonstrate that LRP/LR and hTERT co-localize in perinuclear compartments and the cell surface but undetectable/no co-localization in the nucleus of the HEK293 and MDA_MB231 cells, respectively.

Figure 13:
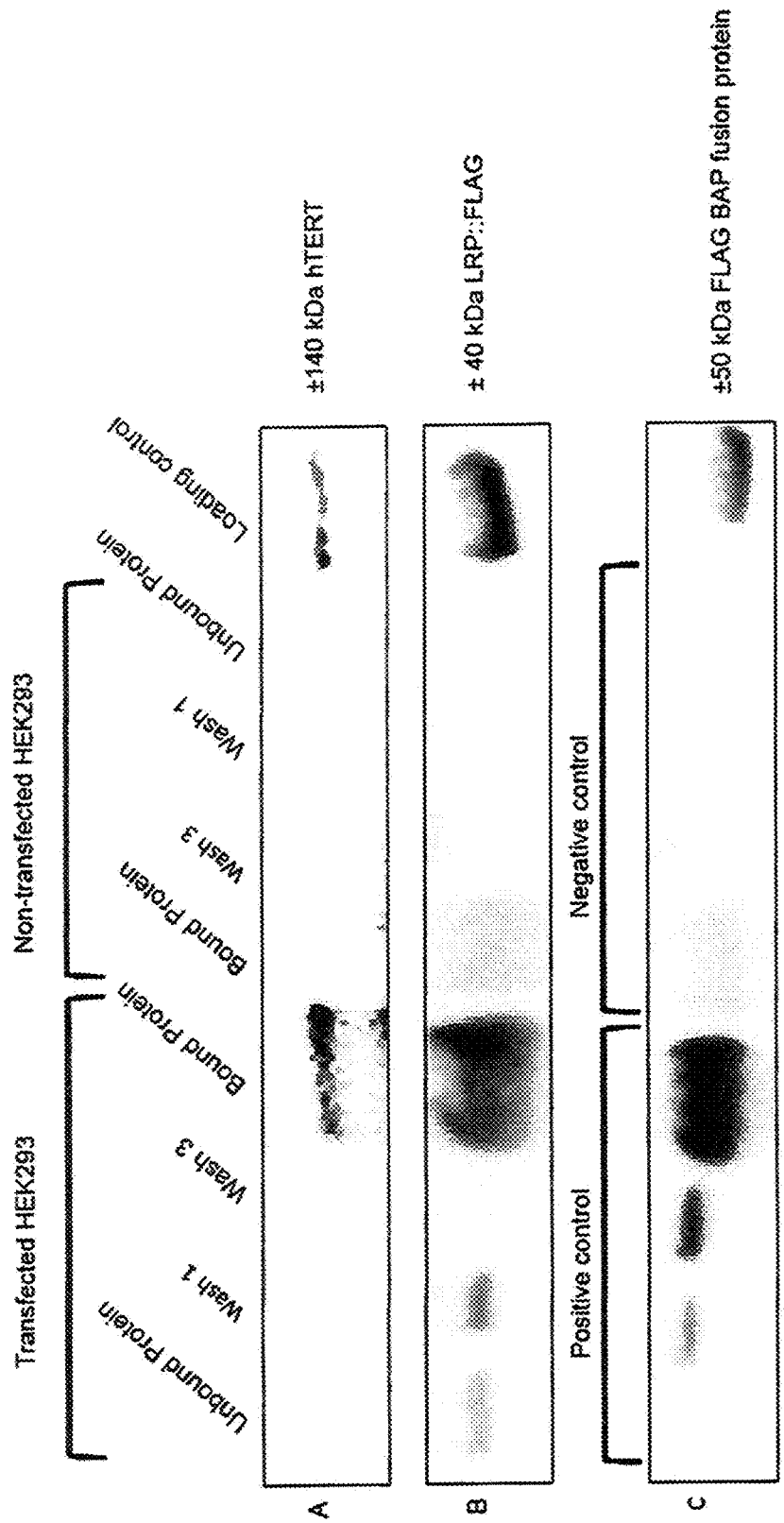
FIG. 13 shows FLAG® immunoprecipitation assays confirming an interaction between LRP/LR and hTERT.

FLAG® co-immunoprecipitation assay of LRP/LR and hTERT confirms interaction:

To assess whether the observed co-localization of the two proteins indicated interaction/association with each other, FLAG® co-immunoprecipitation/pull down assays were performed (FIG. 13). The presence of the LRP::FLAG and hTERT proteins was detected by corresponding antibodies. h-TERT (panel A, bound protein) and LRP::FLAG (panel B, bound protein) both bound to FLAG®M2-beads, in pCIneo-moLRP::FLAG transfected cells, whereas both proteins failed to bind to FLAG®-M2 beads in non-transfected cells (bound protein panel A and B, non-transfected cells). This strongly indicates an interaction/association between hTERT and LRP::FLAG.

siRNA-Mediated Knockdown of LRP/LR Expression in HEK293 and MDA_MB231 Cells:

To assess whether LRP/LR influences telomerase activity, LRP/LR was down-regulated by employing RNA interference technology using small interfering RNAs (siRNAs). The level of LRP/LR expression in HEK293 and MDA_MB231 cells after transfection with siRNA-LAMR1 was determined using western blotting and was quantified by densitometry (FIG. 14). The level of LRP was reduced by 90.48% and 92.59% in HEK293 and MDA_MB231 cells respectively, compared to the non-transfected controls.

siRNA-Mediated Knock-Down of LRP/LR in HEK293 and MDA_MB231 Cells Significantly Impedes Telomerase Activity:

The telomerase activity in response to the siRNA-mediated down regulation of LRP expression in HEK293 and MDA_MB231 cells was assessed using a TRAPeze RT® telomerase detection kit (Merck Millipore). HEK293 and MDA_MB231 cells were transfected with siRNA-LAMR1 and siRNA-TFRC/DICER1 (positive control). The level of telomerase activity in HEK293 and MDA_MB231 cells was significantly reduced (FIG. 15) after the knock-down of LRP/LR.

Discussion (Example 2)

The tumorigenic breast cancer (MDA_MB231) and human embryonic kidneys (HEK293) cells displayed LRP/LR and hTERT on their cell surface and intracellularly. Flow cytometric analysis revealed that MDA_MB231 cells display higher intracellular levels of LRP/LR and hTERT in comparison to the HEK293 cells. Similarly, the cell surface levels of LRP/LR were higher in the tumorigenic cell line. However, there was no significant difference in the cell surface levels of hTERT between the two cell lines. This is most likely due to the fact that MDA_MB231 cells are tumorigenic and need more LRP/LR and hTERT to maintain their tumorigenic character.

The considerably high levels of hTERT on the cell surface may be explained by the presence of an associated peptide known as MHC class 1 which is derived from hTERT and is expressed on the cell surface [40]. This peptide may be recognized by hTERT antibodies. These findings demonstrate that LRP/LR and hTERT are found on both the cell surface and intracellularly of both, HEK293 and MDA_MB231 cells.

Confocal microscopy was employed to investigate whether LRP/LR and hTERT co-localize which raises the potential that these proteins may form an association/interaction (FIG. 12). The co-localization observed between LRP/LR and hTERT on both HEK293 and MDA_MB231 cells indicates that a spatial overlap occurs between the fluorescent immuno-labelled proteins. Although the close cellular proximity of these proteins on the cell surface of both cell lines has been detected, it does still suggest an association between LRP/LR and hTERT. Confocal microscopy was further utilized to examine whether LRP/LR co-localized with hTERT in sub-cellular locations other than the cell surface. From FIG. 12, it is evident that LRP/LR also shows a high degree of co-localization with hTERT within the perinuclear compartment. LRP/LR and hTERT are known to be present in the cytosol, nucleus and perinuclear compartments. From our results, the intracellular distribution of hTERT and LRP/LR is seen to be fairly widespread throughout the perinuclear compartments. This suggests that LRP/LR could be interacting with hTERT within the perinuclear compartments and on the cell surface.

FLAG®-Co-immunoprecipitation/pull down assays confirmed that LRP/LR and hTERT interact with each other. This interaction can either be direct or indirect. An indirect interaction could be mediated by proteins present in the crude lysate of the HEK293 cells.

To investigate whether LRP/LR has an effect on telomerase activity, LRP/LR expression was significantly decreased in MDA_MB231 and HEK293 cells by employing RNAi methodology. siRNAs directed against LRP were transfected into the aforementioned cells and the degree of LRP down regulation was assessed by western blotting followed by densitometric analysis (FIG. 13). The level of LRP expression was significantly reduced by 90.48% and 92.59% in HEK293 and MDA_MB231 cells, respectively. The effect of the knockdown of LRP expression on telomerase activity was investigated by employing the TRAPeze RT® telomerase detection kit (Merck Millipore) and real-time PCR. LRP down regulation resulted in a significant reduction in telomerase activity in HEK293 and MDA_MB231 cells, respectively, suggesting a crucial role of LRP/LR in telomerase activity.

Similarly, it was observed that a significant reduction in telomerase activity after transfection with the siRNA-TFRC/DICER1 positive control. According to Baumer et al., 2010, TFRC and DICER1 enhance telomerase activity [41], which clarifies why the down-regulation of TFRC/DICER1 resulted in a significant decrease of telomerase activity.

Targeting LRP/LR via RNAi methodology may serve as a method to target telomerase activity and may thus be beneficial as a two-pronged approach to cancer treatment. i.e. targeting LRP/LR could also be used in synergy with other cancer drugs to significantly reduce cancer progression.

The fact that the knock-down of LRP resulted in a significant decrease of hTERT activity, suggests that LRP/LR itself increases telomerase activity.

In conclusion, it has been confirmed that HEK293 and MDA_MB231 cells display hTERT and LRP/LR on the cell surface and intracellularly. The LRP/LR-hTERT interaction, confirmed by FLAG® Co-immunoprecipitation, occurs in the perinuclear compartments and on the cell surface. siRNA mediated knockdown of LRP/LR significantly decreased telomerase activity in HEK293 and MDA_MB231 cells. These findings show for the first time a novel function of LRP/LR in contributing to hTERT activity. siRNAs targeting LRP/LR may act as a potential therapeutic tool for cancer treatment by (i) blocking metastasis, (ii) impeding tumor angiogenesis (iii) inducing apoptosis and as demonstrated in this study, by (iv) hampering telomerase activity.

Additional Information about the Figures Relating to Example 2

FIGS. 11 A to 11E shows flow cytometric detection of intracellular and cell surface levels of LRP/LR and hTERT on HEK293 and MDA_MB231 cells. A) shows Intracellular levels of LRP/LR in permeabilised HEK293 and MDA_MB231 cells were determined primarily by incubating the cells with IgG1-iS18 followed by incubation with anti-human-FITC coupled secondary antibodies (Sigma-Aldrich). B) shows intracellular levels of hTERT in permeabilised HEK293 and MDA_MB231 cells were determined primarily by incubating the cells with anti-Telomerase reverse transcriptase antibody followed by incubation with goat anti-mouse IgG-APC coupled secondary antibodies (Sigma-Aldrich). C) shows cell surface levels of LRP/LR in non-permeabilised HEK293 and MDA_MB231 cells were determined primarily by incubating the cells with IgG1-iS18 followed by incubation with anti-human-FITC coupled secondary antibodies (Sigma-Aldrich). D) shows cell surface levels of hTERT in non-permeabilised HEK293 and MDA_MB231 cells were determined primarily by incubating the cells with anti-telomerase reverse transcriptase antibody followed by incubation with Goat anti-mouse IgG-APC coupled secondary antibodies (Sigma-Aldrich). The blue curve represents the no primary antibody control (to account for non-specificity of the secondary antibodies), whilst the red curve represents cells that were treated with both primary and secondary antibodies. The percentage represents the proportion of cells within the population which expressed LRP/LR and hTERT intracellularly and on the cell surface. This was calculated using a linked marker from the point of intersection between the curves to the end of the red curve. E) shows the results from 11A to 11D tabulated for ease of reference.

FIGS. 12A to 12D show confocal microscopy analysis of the interaction between LRP/LR and hTERT on MDA_MB231 and HEK293 cells. A) shows intracellular LRP/LR and hTERT on immunolabelled HEK293 cells. (B) shows endogenous cell surface LRP/LR and hTERT on immunolabelled HEK293. (C) shows intracellular LRP/LR and hTERT on immunolabelled MDA_MB231 cells. (D) shows endogenous cell surface LRP/LR and hTERT on immunolabelled MDA_MB231. hTERT was detected using anti-telomerase reverse transcriptase and anti-goat to mouse-APC antibodies. LRP/LR was detected employing anti-IgG-iS18 and anti-human-FITC antibodies. Merged images verified the co-localization. The yellow staining indicates areas of co-localization. Secondary antibody controls are shown beneath each panel. Fluorescence was detected and images were acquired using the Olympus IX71 Immunofluorescence Microscope and Analysis Get It Research Software. Scale bars are 20 µm. White arrows point to areas of co-localization.

FIG. 13 shows FLAG® immunoprecipitation assays confirming an interaction between LRP/LR and hTERT. Pull down assays were used to detect LRP::FLAG as well as any associated proteins bound to the anti-M2 flag beads. A loading control of crude HEK293 lysate was incorporated to ensure the validity of the blots. Panel C indicates the positive and negative controls, where the Bound protein shows the detection of the BAP fusion protein (50 kDa) to the anti-FLAG beads. Panel B indicates that the LRP::FLAG protein was only present in the HEK293 transfected samples, where FLAG was detected on the anti-FLAG beads (Bound protein). Panel A illustrates the detection of a ±140 kDa band (Bound protein) showing a pull down of hTERT for the HEK293 transfected cell line, whereas no signal was detected for the non-transfected HEK293 cell line.

Figure 14A:
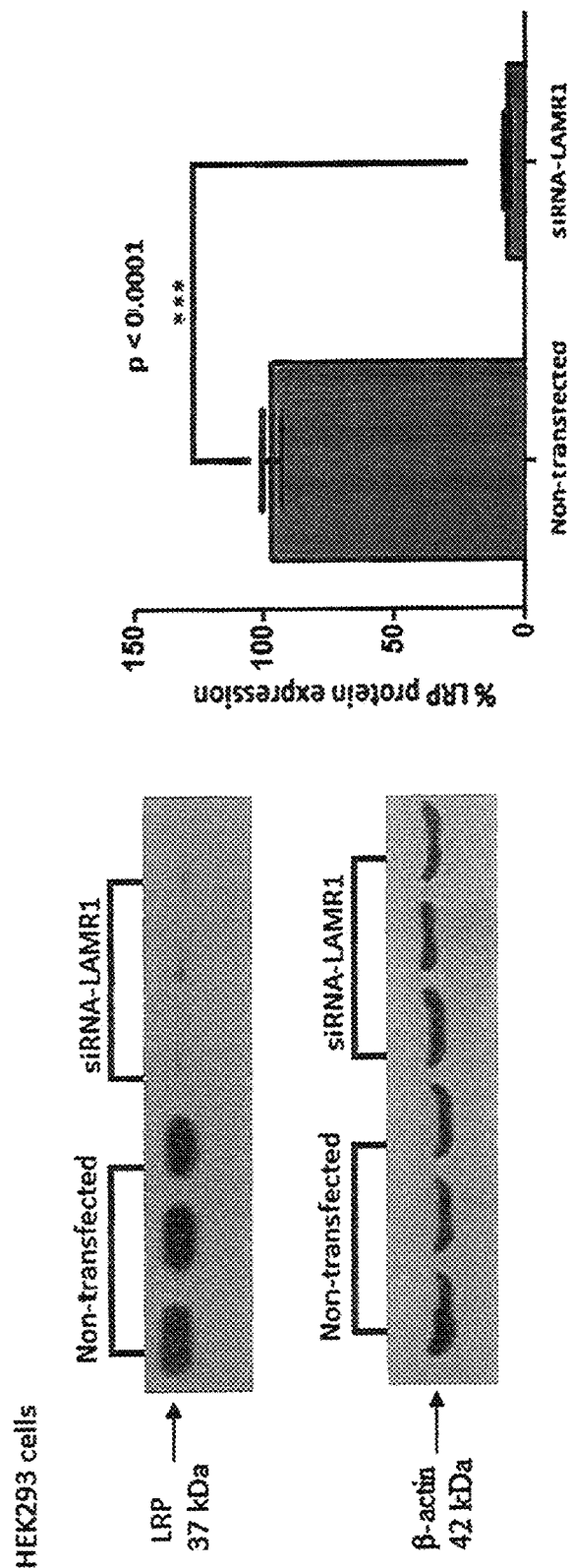
FIG. 14A shows siRNA-mediated knock-down of LRP/LR in HEK293. Densitometric analysis of western blot signals revealed a significant (*** p<0.001) 90.48% and 92.59% reduction in LRP protein expression in (A) shows HEK293, compared to control non-transfected cells (set at 100%)
Figure 14B:
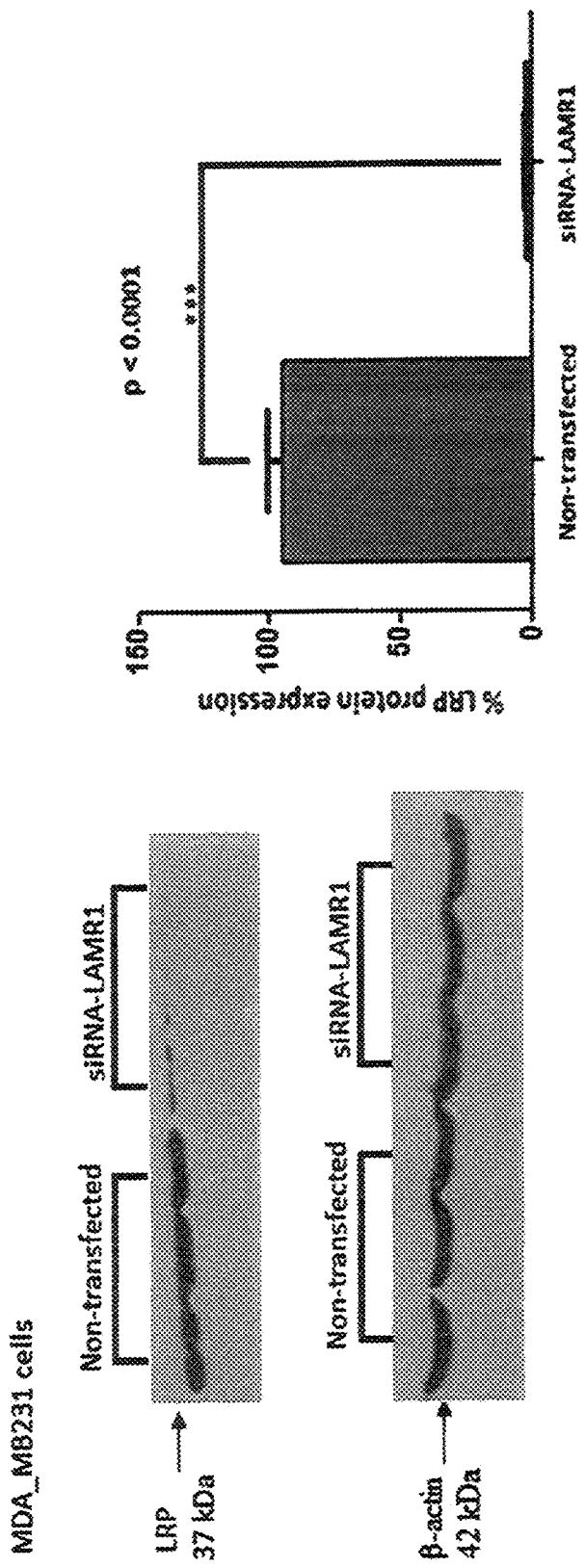
FIG. 14B shows siRNA-mediated knock-down of LRP/LR MDA_MB231 cells. Densitometric analysis of western blot signals revealed a significant (* p<0.001) 90.48% and 92.59% reduction in LRP protein expression in (B) shows MDA_MB231 cells, compared to control non-transfected cells (set at 100%)

FIGS. 14A and 14B shows siRNA-mediated knock-down of LRP/LR in HEK293 and MDA_MB231 cells. The expression level in HEK293 and MDA_MB231 cells was investigated 72 h post-transfection with siRNA-LAMR1. Densitometric analysis of western blot signals revealed a significant (*** $p<0.001$) 90.48% and 92.59% reduction in LRP protein expression in A) shows HEK293 and B) shows MDA_MB231 cells, respectively, compared to control non-transfected cells (set at 100%).

Figure 15A:
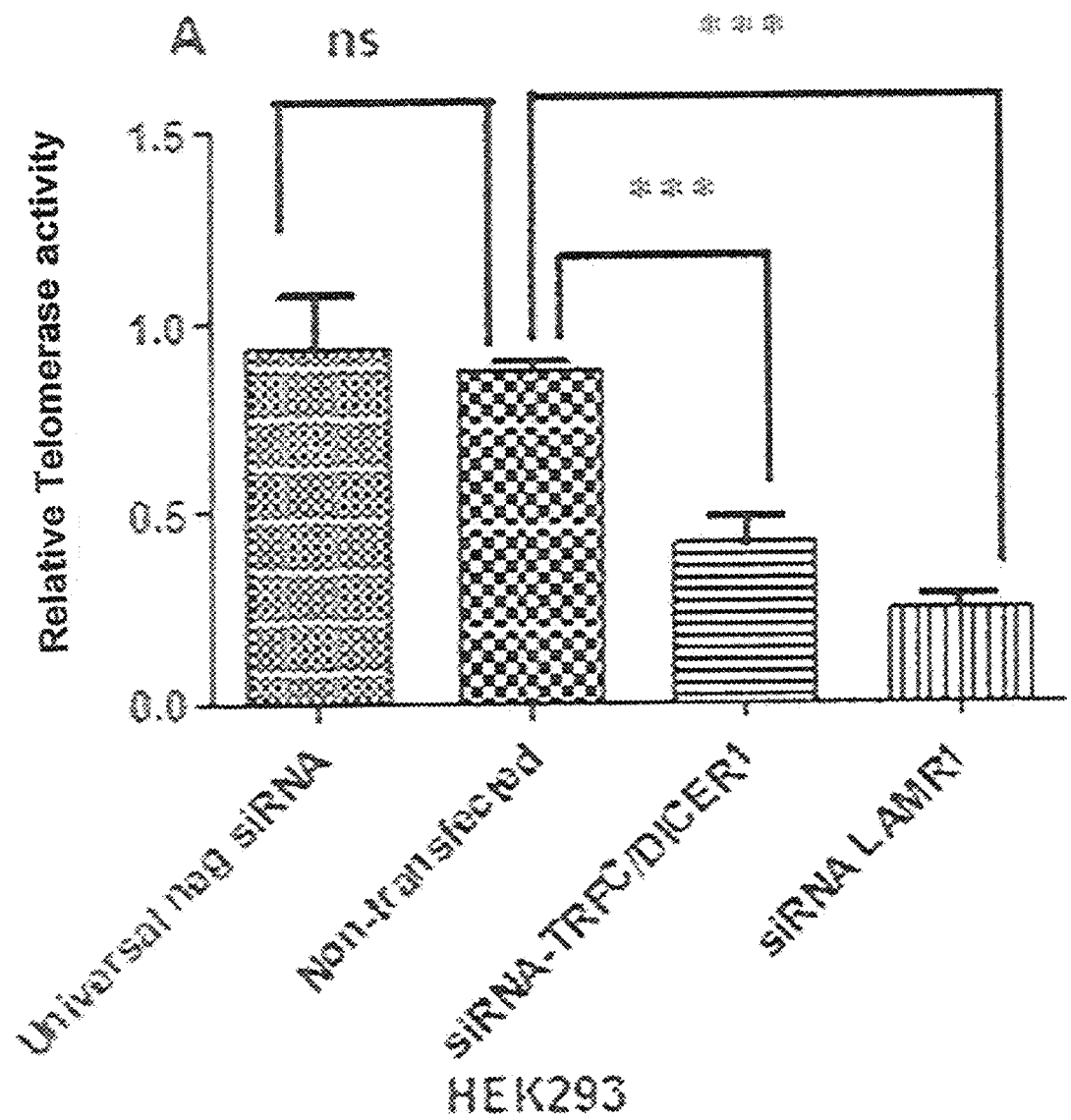
FIG. 15A TO 15C shows the effect of LRP/LR on telomerase activity in HEK293 and MDA_MB231 cells. Analysis of the concentrations revealed a significant (* p<0.001) reduction in telomerase activity once LRP was knockdown in (A) HEK293, (B) and (C) MDA_MB231 cells, respectively, compared to control non-transfected cells and negative control siRNA transfected cells. Non-significant (ns) at p>0.05.
Figure 15B:
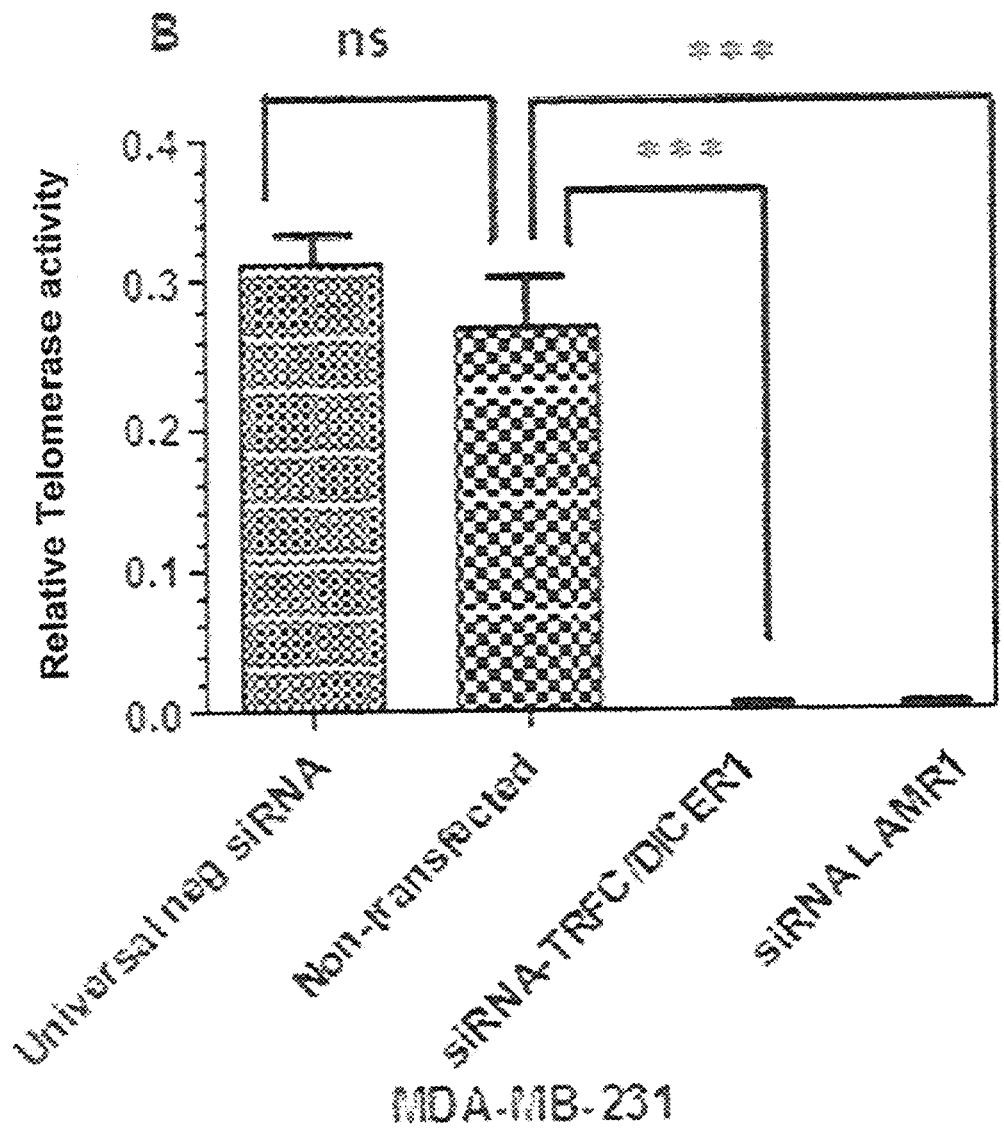
Figure 15C:
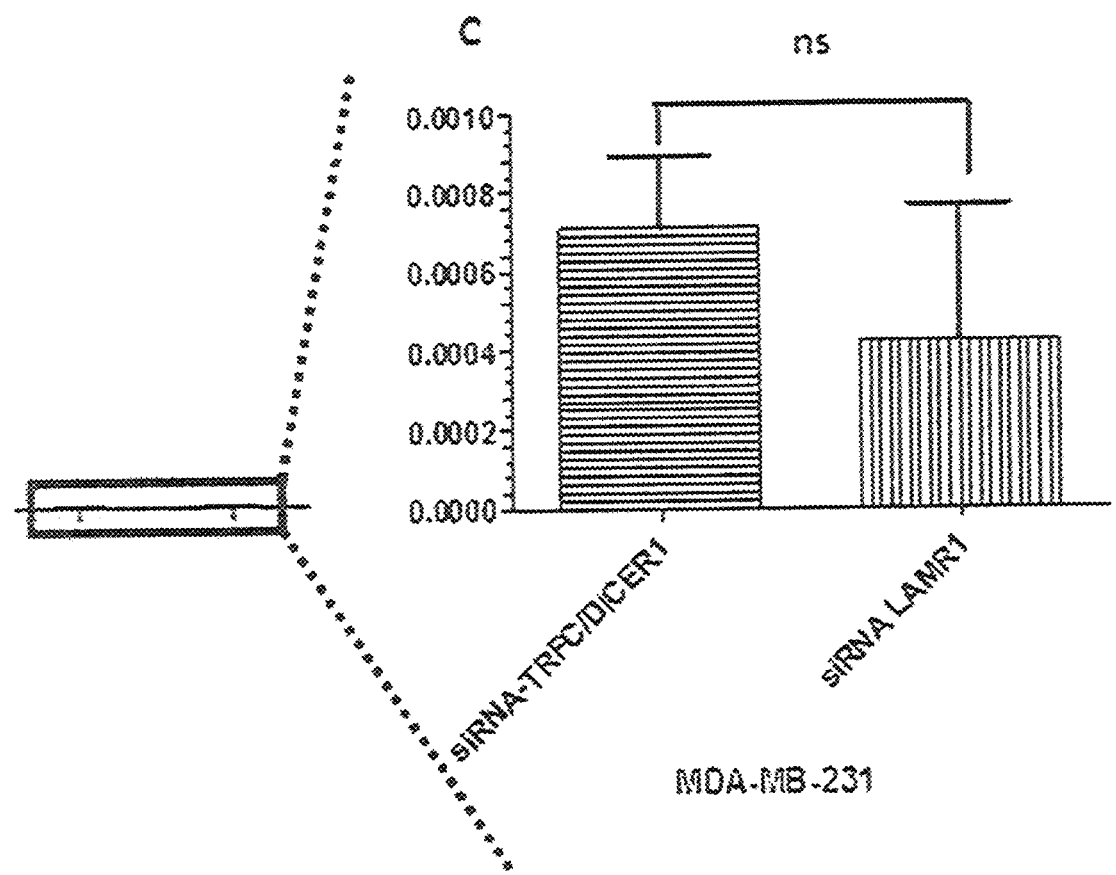

FIG. 15A to 15C shows the effect of LRP/LR on telomerase activity in HEK293 and MDA_MB231 cells. The expression level in HEK293 and MDA_MB231 cells was investigated using TRAPEZE Telomerase kit (Merck Millipore) and qPCR. Analysis of the concentrations revealed a significant (*** $p<0.001$) reduction in telomerase activity once LRP was knockdown in A) HEK293, B) and C) MDA_MB231 cells, respectively, compared to control non-transfected cells and negative control siRNA transfected cells. Non-significant (ns) at $p>0.05$.

REFERENCES

1. Omar A, Jovanovic K, Da Costa Dias B, Gonsalves D, Moodley K, Caveney R, et al. Patented biological approaches for the therapeutic modulation of the 37 kDa/67 kDa laminin receptor. Expert Opin Ther Pat. 2011; 21(1):35-53. Epub 2010/11/30. doi: 10.1517/13543776.2011.539203. PubMed PMID: 21110766.
2. Mbazima V, Da Costa Dias B, Omar A, Jovanovic K, Weiss S F. Interactions between PrP(c) and other ligands with the 37-kDa/67-kDa laminin receptor. Front Biosci (Schol Ed). 2010; 15:1150-63. Epub 2010/06/03. PubMed PMID: 20515747.
3. Chetty C, Khumalo T, Da Costa Dias B, Reusch U, Knackmuss S, Little M, et al. Anti-LRP/LR specific antibody IgG1-iS18 impedes adhesion and invasion of liver cancer cells. PLoS One. 2014; 9(5):e96268. Epub 2014/05/07. doi: 10.1371/journal.pone.0096268. PubMed PMID: 24798101; PubMed Central PMCID: PMC4010454.
4. Omar A, Reusch U, Knackmuss S, Little M, Weiss S F. Anti-LRP/LR-specific antibody IgG1-iS18 significantly reduces adhesion and invasion of metastatic lung, cervix, colon and prostate cancer cells. J Mol Biol. 2012; 419(1-2):102-9. Epub 2012/03/07. doi: 10.1016/j.jmb.2012.02.035. PubMed PMID: 22391421.
5. Khumalo T, Reusch U, Knackmuss S, Little M, Veale R B, Weiss S F. Adhesion and Invasion of Breast and Oesophageal Cancer Cells Are Impeded by Anti-LRP/LR-Specific Antibody IgG1-iS18. PLoS One. 2013; 8(6):e66297. Epub 2013/07/05. doi: 10.1371/journal.pone.0066297. PubMed PMID: 23823499; PubMed Central PMCID: PMC3688881.
6. Zuber C, Knackmuss S, Zemora G, Reusch U, Vlasova E, Diehl D, et al. Invasion of tumorigenic HT1080 cells is impeded by blocking or downregulating the 37-kDa/67-kDa laminin receptor. J Mol Biol. 2008; 378(3):530-9. Epub 2008/04/05. doi: 10.1016/j.jmb.2008.02.004. PubMed PMID: 18387633.
7. Khumalo T, Ferreira E, Jovanovic K, Veale R B, Weiss S F. Knockdown of LRP/LR Induces Apoptosis in Breast and Oesophageal Cancer Cells. PloS one. 2015; 10(10):e0139584. Epub 2015/10/02. doi: 10.1371/journal.pone.0139584. PubMed PMID: 26427016.
8. Rieger R, Edenhofer F, Lasmezas C I, Weiss S. The human 37-kDa laminin receptor precursor interacts with the prion protein in eukaryotic cells. Nat Med. 1997; 3(12):1383-8. Epub 1997/12/13. PubMed PMID: 9396609.
9. Gauczynski S, Peyrin J M, Haik S, Leucht C, Hundt C, Rieger R, et al. The 37-kDa/67-kDa laminin receptor acts as the cell-surface receptor for the cellular prion protein. Embo J. 2001; 20(21):5863-75. Epub 2001/11/02. doi: 10.1093/emboj/20.21.5863. PubMed PMID: 11689427; PubMed Central PMCID: PMC125290.
10. Hundt C, Peyrin J M, Haik S, Gauczynski S, Leucht C, Rieger R, et al. Identification of interaction domains of the prion protein with its 37-kDa/67-kDa laminin receptor. Embo J. 2001; 20(21):5876-86. Epub 2001/11/02. doi: 10.1093/emboj/20.21.5876. PubMed PMID: 11689428; PubMed Central PMCID: PMC125289.
11. Gauczynski S, Nikles D, El-Gogo S, Papy-Garcia D, Rey C, Alban S, et al. The 37-kDa/67-kDa laminin receptor acts as a receptor for infectious prions and is inhibited by polysulfated glycanes. J Infect Dis. 2006; 194(5):702-9. Epub 2006/08/10. doi: 10.1086/505914. PubMed PMID: 16897671.
12. Leucht C, Simoneau S, Rey C, Vana K, Rieger R, Lasmezas C I, et al. The 37 kDa/67 kDa laminin receptor is required for PrP(Sc) propagation in scrapie-infected neuronal cells. EMBO Rep. 2003; 4(3):290-5. Epub 2003/03/14. doi: 10.1038/sj.embor.embor768. PubMed PMID: 12634848; PubMed Central PMCID: PMC1315896.

13. Da Costa Dias B, Jovanovic K, Gonsalves D, Moodley K, Reusch U, Knackmuss S, et al. Anti-LRP/LR specific antibody IgG1-iS18 and knock-down of LRP/LR by shRNAs rescue cells from Abeta42 induced cytotoxicity. Sci Rep. 2013; 3:2702. Epub 2013/09/21. doi: 10.1038/srep02702. PubMed PMID: 24048171; PubMed Central PMCID: PMC3776967.

14. Da Costa Dias B, Jovanovic K, Gonsalves D, Moodley K, Reusch U, Knackmuss S, et al. The 37 kDa/67 kDa laminin receptor acts as a receptor for Abeta42 internalization. Sci Rep. 2014; 4:5556. Epub 2014/07/06. doi: 10.1038/srep05556. PubMed PMID: 24990253; PubMed Central PMCID: PMC4080222.

15. Jovanovic K, Loos B, Da Costa Dias B, Penny C, Weiss S F. High resolution imaging study of interactions between the 37 kDa/67 kDa laminin receptor and APP, beta-secretase and gamma-secretase in Alzheimer's disease. PLoS One. 2014; 9(6):e100373. Epub 2014/06/28. doi: 10.1371/journal.pone.0100373. PubMed PMID: 24972054; PubMed Central PMCID: PMC4074076.

16. Jovanovic K, Gonsalves D, Da Costa Dias B, Moodley K, Reusch U, Knackmuss S, et al. Anti-LRP/LR specific antibodies and shRNAs impede amyloid beta shedding in Alzheimer's disease. Sci Rep. 2013; 3:2699. Epub 2013/09/21. doi: 10.1038/srep02699. PubMed PMID: 24048412; PubMed Central PMCID: PMC3776966.

17. Pinnock E C, Jovanovic, K., Pinto, M. G., Ferreira, E., Da Costa Dias, B., Penny, C., Knackmuss, S., Reusch, U., Little, M., Schatzl., H. M. and Weiss, S. T. F. LRP/LR antibody mediated rescuing of Abeta induced cytotoxicity is dependent on PrPc in Alzheimer's Disease. J Alzheimer's Disease 2016.

18. Griffith J D, Comeau L, Rosenfield S, Stansel R M, Bianchi A, Moss H, et al Mammalian telomeres end in a large duplex loop. Cell. 1999; 97(4):503-14. Epub 1999/05/25. PubMed PMID: 10338214.

19. de Lange T. Shelterin: the protein complex that shapes and safeguards human telomeres. Genes Dev. 2005; 19(18):2100-10. Epub 2005/09/17. doi: 10.1101/gad.1346005. PubMed PMID: 16166375.

20. Letsolo B T, Rowson J, Baird D M. Fusion of short telomeres in human cells is characterized by extensive deletion and microhomology, and can result in complex rearrangements. Nucleic Acids Res. 2010; 38(6):1841-52. Epub 2009/12/23. doi: 10.1093/nar/gkp1183. PubMed PMID: 20026586; PubMed Central PMCID: PMC2847243.

21. Capper R, Britt-Compton B, Tankimanova M, Rowson J, Letsolo B, Man S, et al. The nature of telomere fusion and a definition of the critical telomere length in human cells. Genes Dev. 2007; 21(19):2495-508. Epub 2007/10/03. doi: 10.1101/gad.439107. PubMed PMID: 17908935; PubMed Central PMCID: PMC1993879.

22. Palm W, de Lange T. How shelterin protects mammalian telomeres. Annu Rev Genet. 2008; 42:301-34. Epub 2008/08/06. doi: 10.1146/annurev.genet.41.110306.130350. PubMed PMID: 18680434.

23. Harley C B, Futcher A B, Greider C W. Telomeres shorten during ageing of human fibroblasts. Nature. 1990; 345(6274):458-60. Epub 1990/05/31. doi: 10.1038/345458a0. PubMed PMID: 2342578.

24. Harley C B, Kim N W, Prowse K R, Weinrich S L, Hirsch K S, West M D, et al. Telomerase, cell immortality, and cancer. Cold Spring Harb Symp Quant Biol. 1994; 59:307-15. Epub 1994/01/01. PubMed PMID: 7587082.

25. Allsopp R C, Chang E, Kashefi-Aazam M, Rogaev E I, Piatyszek M A, Shay J W, et al. Telomere shortening is associated with cell division in vitro and in vivo. Exp Cell Res. 1995; 220(1):194-200. Epub 1995/09/01. doi: 10.1006/excr.1995.1306. PubMed PMID: 7664836.

26. Harley C B, Vaziri H, Counter C M, Allsopp R C. The telomere hypothesis of cellular aging. Exp Gerontol. 1992; 27(4):375-82. Epub 1992/07/01. PubMed PMID: 1459213.

27. Shay J W, Wright W E. Senescence and immortalization: role of telomeres and telomerase. Carcinogenesis. 2005; 26(5):867-74. Epub 2004/10/09. doi: 10.1093/carcin/bgh296. PubMed PMID: 15471900.

28. Wright W E, Shay J W. The two-stage mechanism controlling cellular senescence and immortalization. Exp Gerontol. 1992; 27(4):383-9. Epub 1992/07/01. PubMed PMID: 1333985.

29. Shay J W, Pereira-Smith O M, Wright W E. A role for both RB and p53 in the regulation of human cellular senescence. Exp Cell Res. 1991; 196(1):33-9. Epub 1991/09/01. PubMed PMID: 1652450.

30. Greider C W, Blackburn E H. Telomeres, telomerase and cancer. Sci Am. 1996; 274(2):92-7. Epub 1996/02/01. PubMed PMID: 8560215.

31. Holt S E, Wright W E, Shay J W. Regulation of telomerase activity in immortal cell lines. Mol Cell Biol. 1996; 16(6):2932-9. Epub 1996/06/01. PubMed PMID: 8649404; PubMed Central PMCID: PMC231287.

32. Bodnar A G, Ouellette M, Frolkis M, Holt S E, Chiu C P, Morin G B, et al. Extension of life-span by introduction of telomerase into normal human cells. Science. 1998; 279(5349):349-52. Epub 1998/02/07. PubMed PMID: 9454332.

33. Kim N W, Piatyszek M A, Prowse K R, Harley C B, West M D, Ho P L, et al. Specific association of human telomerase activity with immortal cells and cancer. Science. 1994; 266(5193):2011-5. Epub 1994/12/23. PubMed PMID: 7605428.

34. Tomas-Loba A, Flores I, Fernandez-Marcos P J, Cayuela M L, Maraver A, Tejera A, et al. Telomerase reverse transcriptase delays aging in cancer-resistant mice. Cell. 2008; 135(4):609-22. Epub 2008/11/18. doi: 10.1016/j.cell.2008.09.034. PubMed PMID: 19013273.

35. Bernardes de Jesus B, Vera E, Schneeberger K, Tejera A M, Ayuso E, Bosch F, et al. Telomerase gene therapy in adult and old mice delays aging and increases longevity without increasing cancer. EMBO Mol Med. 2012; 4(8): 691-704. Epub 2012/05/16. doi: 10.1002/emmm 201200245. PubMed PMID: 22585399; PubMed Central PMCID: PMC3494070.

36. Zuber C, Knackmuss S, Zemora G, Reusch U, Vlasova E, Diehl D, et al. Invasion of tumorigenic HT1080 cells is impeded by blocking or downregulating the 37-kDa/67-kDa laminin receptor. Journal of molecular biology. 2008; 378(3):530-9. Epub 2008/04/05. doi: 10.1016/j.jmb.2008.02.004. PubMed PMID: 18387633.

37. Vana K, Weiss S. A trans-dominant negative 37 kDa/67 kDa laminin receptor mutant impairs PrP(Sc) propagation in scrapie-infected neuronal cells. Journal of molecular biology. 2006; 358(1):57-66. Epub 2006/03/07. doi: 10.1016/j.jmb.2006.02.011. PubMed PMID: 16516231.

38. Moodley K, Weiss S F. Downregulation of the non-integrin laminin receptor reduces cellular viability by inducing apoptosis in lung and cervical cancer cells. PLoS One. 2013; 8(3):e57409. Epub 2013/03/09. doi: 10.1371/journal.pone.0057409. PubMed PMID: 23472084; PubMed Central PMCID: PMC3589420.

39. Khusal R, Da Costa Dias B, Moodley K, Penny C, Reusch U, Knackmuss S, et al. In vitro inhibition of angiogenesis by antibodies directed against the 37 kDa/67 kDa laminin receptor. PLoS One. 2013; 8(3):e58888. Epub 2013/04/05. doi: 10.1371/journal.pone.0058888. PubMed PMID: 23554951; PubMed Central PMCID: PMC3595224.

40. Pierre Langlade-Demoyen, Fransisco Garcia Pons, Olivier Adotevi, Sylvain Cardinaud, Neuveut C, inventorsPOLYNUCLEOTIDES ENCODING MHC CLASS I-RESTRICTED HTERT EPITOPES, ANALOGUES THEREOF OR POLYEPITOPES patent US 20140056932. 2010.

41. Baumer Y, Funk D, Schlosshauer B. Does telomerase reverse transcriptase induce functional de-differentiation of human endothelial cells? Cell Mol Life Sci. 2010; 67(14):2451-65. Epub 2010/03/31. doi: 10.1007/s00018-010-0349-z. PubMed PMID: 20352467.

42. Li X, Lewis M T, Huang J, Gutierrez C, Osborne C K, Wu M F, et al. Intrinsic resistance of tumorigenic breast cancer cells to chemotherapy. J Natl Cancer Inst. 2008; 100(9):672-9. Epub 2008/05/01. doi: 10.1093/jnci/djn123. PubMed PMID: 18445819.

43. Lu L, Zhang C, Zhu G, Irwin M, Risch H, Menato G, et al. Telomerase expression and telomere length in breast cancer and their associations with adjuvant treatment and disease outcome. Breast Cancer Res. 2011; 13(3):R56. Epub 2011/06/08. doi: 10.1186/bcr2893. PubMed PMID: 21645396; PubMed Central PMCID: PMC3218945.

The Applicant believes that the invention provides for at least new and inventive compounds, pharmaceutical compositions, and/or methods to treat and/or prevent telomere related diseases and/or telomere related medical conditions, particularly cancer and/or cellular ageing, and/or compounds for use in the treatment and/or prevention of telomere related diseases and/or telomere related medical conditions.

While the invention has been described in detail with respect to specific embodiments and/or examples thereof, it will be appreciated that those skilled in the art, upon attaining an understanding of the foregoing may readily conceive of alterations to, variations of and equivalents to these embodiments. Accordingly, the scope of the present invention should be assessed as that of the claims and any equivalents thereto, which claims are appended hereto.

The invention claimed is:

1. A method comprising: (a) transfecting a cell with a transfecting agent and (b) producing within the cell a 37 kDa/67 kDa laminin receptor precursor/high affinity laminin receptor (LRP/LR) comprising the amino acid sequence of SEQ ID NO: 1 or SEQ ID NO: 2; wherein the level of human telomerase reverse transcription, telomerase activity, and/or telomere length is increased; and wherein the level of a senescent marker is decreased.

2. The method of claim 1, wherein the cell is from an animal, or a plant.

3. The method of claim 1, wherein a senescent markers is selected from the group consisting of β-galactosidase, progerin, and H2AX foci.

4. The method of claim 1, wherein the cell is a HEK293 or MRC 5 cell.

5. The method of claim 1, wherein the transfecting agent is a pCIneo-LRP-FLAG plasmid.

6. The method of claim 5, wherein the pCIneo-LRP-FLAG plasmid comprises an amino acid sequence of SEQ ID NO: 3.

* * * * *